United States Patent
Chang et al.

(10) Patent No.: US 7,943,306 B2
(45) Date of Patent: May 17, 2011

(54) GENE EXPRESSION SIGNATURE FOR PREDICTION OF HUMAN CANCER PROGRESSION

(75) Inventors: Howard Yuan-Hao Chang, Burlingame, CA (US); Julie Sneddon, Palo Alto, CA (US); Patrick O. Brown, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 604 days.

(21) Appl. No.: 11/332,547

(22) Filed: Jan. 12, 2006

(65) Prior Publication Data

US 2006/0183141 A1    Aug. 17, 2006

Related U.S. Application Data

(60) Provisional application No. 60/643,610, filed on Jan. 12, 2005.

(51) Int. Cl.
*C07H 21/02* (2006.01)
*C12Q 1/68* (2006.01)

(52) U.S. Cl. .......................................... 435/6; 536/23.1

(58) Field of Classification Search ........................ None
See application file for complete search history.

(56) References Cited

OTHER PUBLICATIONS

Tockman et al (Cancer Res., 1992, 52:2711s-2718s).*
Akiri et al (Cancer Research, Apr. 1, 2003, 63:1657-1666).*
Chang et al (PLOS Biology, Feb. 2004, 2(2):0206-0214).*
Beren and Simons (Molecular Microbiology, 2001, 39(1):112-125).*
Sorlie et al (PNAS, Sep. 11, 2001, 98(19): 10869-10874).*
Tibshirani et al (PNAS, May 14, 2002, 99(10): 6567-6572).*
Kawamoto et al (Genome Research, Dec. 1999, 9(12):1305-1312).*
Bhattacharjee, A., et al., "Classification of human lung carcinomas by mRNA expression profiling reveals distinct adenocarcinoma subclasses," (2001) *PNAS*, 98(24):13790-13795.
Chang, H., et al., "Diversity, topographic differentiation, and positional memory in human fibroblasts," (2002) *PNAS*, 99(20):12877-12882.
Chang, H., et al., "Gene expression signature of fibroblast serum response predicts human cancer progression: similarities between tumors and wounds," (2004) *PLoS Biology*, 2(2):0206-0214.
Eisen, M., et al., "Cluster analysis and display of genome-wide expression patterns," (1998) *PNAS*, 95:14863-14868.
Perou, et al., "Molecular portraits of human breast tumors," (2000) *Nature*, 406:747-752.
Tusher, et al., "Significance analysis of microarrays applied to the ionizing radiation response," (2001) *PNAS*, 98(9):5116-5121.
Van 'T Veer, et al., "Gene expression profiling predicts clinical outcome of breast cancer," (2002) *Nature*, 415:530-536.
Vishwanath, R, et al., "The transcriptional program in the response to human fibroblasts to serum," (1999) *Science* 283:83-87.
Whitfield, M., et al., "Identification of genes periodically expressed in the human cell cycle and their expression in tumors," (2002) *Molecular Biology of the Cell*, 13:1977-2000.

* cited by examiner

*Primary Examiner* — Sean E Aeder
(74) *Attorney, Agent, or Firm* — Bozicevic, Field & Francis LLP; Pamela J. Sherwood

(57) ABSTRACT

Methods are provided for classification of cancers by the expression of a set of genes referred to as the core serum response (CSR), or a subset thereof. The expression pattern of the CSR in normal tissues correlates with that seen in quiescent fibroblasts cultured in the absence of serum, while cancer tissues can be classified as having a quiescent or induced CSR signature. Patients with the induced CSR signature have a higher probability of metastasis. Classification according to CSR signature allows optimization of treatment, and determination of whether on whether to proceed with a specific therapy, and how to optimize dose, choice of treatment, and the like.

11 Claims, 12 Drawing Sheets
(12 of 12 Drawing Sheet(s) Filed in Color)

GENE EXPRESSION SIGNATURE FOR PREDICTION OF HUMAN CANCER PROGRESSION

This invention was made with Government support under contract NIH CA77097 awarded by the National Institutes of Health. The Government has certain rights in this invention.

In recent years, microarray analysis of gene expression patterns has provided a way to improve the diagnosis and risk stratification of many cancers. Unsupervised analysis of global gene expression patterns has identified molecularly distinct subtypes of cancer, distinguished by extensive differences in gene expression, in diseases that were considered homogeneous based on classical diagnostic methods. Such molecular subtypes are often associated with different clinical outcomes. Global gene expression pattern can also be examined for features that correlate with clinical behavior to create prognostic signatures.

Cancer, like many diseases, is not the result of a single, well-defined cause, but rather can be viewed as several diseases, each caused by different aberrations in informational pathways, which ultimately result in apparently similar pathologic phenotypes. Identification of polynucleotides that are differentially expressed in cancerous, pre-cancerous, or low metastatic potential cells relative to normal cells of the same tissue type can provide the basis for diagnostic tools, facilitates drug discovery by providing for targets for candidate agents, and further serves to identify therapeutic targets for cancer therapies that are more tailored for the type of cancer to be treated.

Identification of differentially expressed gene products also furthers the understanding of the progression and nature of complex diseases such as cancer, and is key to identifying the genetic factors that are responsible for the phenotypes associated with development of, for example, the metastatic phenotype. Identification of gene products that are differentially expressed at various stages, and in various types of cancers, can both provide for early diagnostic tests, and further serve as therapeutic targets. Additionally, the product of a differentially expressed gene can be the basis for screening assays to identify chemotherapeutic agents that modulate its activity (e.g. its expression, biological activity, and the like).

By detailing the expression level of thousands of genes simultaneously in tumor cells and their surrounding stroma, gene expression profiles of tumors can provide "molecular portraits" of human cancers. The variations in gene expression patterns in human cancers are multidimensional and typically represent the contributions and interactions of numerous distinct cells and diverse physiological, regulatory, and genetic factors. Although gene expression patterns that correlate with different clinical outcomes can be identified from microarray data, the biological processes that the genes represent and thus the appropriate therapeutic interventions are generally not obvious.

Gene expression patterns provide a common language among biologic phenomena and allow an alternative approach to infer physiologic and molecular mechanisms from complex human disease states. Starting with the gene expression profile of cells manipulated in vitro to simulate a biologic process, the expression profile can then be used to interpret the gene expression data of human cancers and test specific hypotheses. However, as in other methodologies, reproducibility and scales for interpretation should to be evaluated before this strategy can be generally adopted for biologic discovery and clinical use.

Early disease diagnosis is of central importance to halting disease progression, and reducing morbidity. Analysis of a patient's tumor to identify gene expression patterns provides the basis for more specific, rational cancer therapy that may result in diminished adverse side effects relative to conventional therapies. Furthermore, confirmation that a tumor poses less risk to the patient (e.g., that the tumor is benign) can avoid unnecessary therapies. In short, identification of gene expression patterns in cancerous cells can provide the basis of therapeutics, diagnostics, prognostics, therametrics, and the like.

Since the classic observations of the many histologic similarities between the tumor microenvironment and normal wound healing, it has been proposed that tumor stroma is "normal wound healing gone awry. During normal wound healing, coagulation of extravasated blood initiates a complex cascade of signals that recruit inflammatory cells, stimulate fibroblast and epithelial cell proliferation, direct cell migration, and induce angiogenesis to restore tissue integrity. Many of these normally reparative processes may be constitutively active in the tumor milieu and critical for tumor engraftment, local invasion, and metastasis to distant organs. Indeed, keratinocytes from the wound edge transiently exhibit many similarities to their transformed counterparts in squamous cell carcinomas. Epidemiologically, chronic wound and inflammatory states are well-known risk factors for cancer development: the connection between cirrhosis and liver cancer, gastric ulcers and gastric carcinoma, and burn wounds and subsequent squamous cell carcinoma (so-called Majorlin's ulcer) are but a few examples. In the genetic blistering disorder recessive dystrophic epidermolysis bullosa, nearly 80% of the patients develop aggressive squamous cell carcinoma in their lifetime, attesting to the powerful inductive environment of wounds for cancer development.

In recent years, the roles of angiogenesis, extracellular matrix remodeling, and directed cell motility in cancer progression have been intensely studied. Nonetheless, a comprehensive molecular view of wound healing and its relationship to human cancer is still lacking. Thus, there is currently no established method to quantify the risk of cancer from wounds diagnostically or to intervene therapeutically.

Fibroblasts are ubiquitous mesenchymal cells in the stroma of all epithelial organs and play important roles in organ development, wound healing, inflammation, and fibrosis. Fibroblasts from each anatomic site of the body are differentiated in a site-specific fashion and thus may play a key role in establishing and maintaining positional identity in tissues and organs. Tumor-associated fibroblasts have previously been shown to promote the engraftment and metastasis of orthotopic tumor cells of many epithelial lineages. The genomic response of foreskin fibroblasts to serum, the soluble fraction of coagulated blood, represents a broadly coordinated and multifaceted wound-healing program that includes regulation of hemostasis, cell cycle progression, epithelial cell migration, inflammation, and angiogenesis.

The identification of a canonical gene expression signature of the fibroblast serum response, might provide a molecular gauge for the presence and physiologic significance of the wound-healing process in human cancers. The present invention addresses this issue.

SUMMARY OF THE INVENTION

Methods are provided for classification of cancers, particularly carcinomas. The global transcriptional response of fibroblasts to serum integrates many processes involved in wound healing, which response is characterized herein by the expression of a set of genes referred to as the core serum response (CSR), or a subset thereof. A predominantly biphasic pattern of expression for the CSR is found in diverse cancers, including breast cancers, lung cancers, gastric cancers, prostate cancers, and hepatocellular carcinoma. The expression pattern of the CSR in normal tissues correlates with that seen in quiescent fibroblasts cultured in the absence of serum, while cancer tissues can be classified as having a quiescent or induced CSR signature. Patients with the induced CSR signature have a higher probability of metastasis. Classification according to CSR signature allows optimization of treatment, and determination of whether on whether to proceed with a specific therapy, and how to optimize dose, choice of treatment, and the like.

In another embodiment of the invention, methods are provided for statistical analysis of expression profile data to determine whether a pattern of expression or response will be predictive of a phenotype of interest.

In some embodiments of the invention, hierarchical clustering can be used to assess the similarity between the CSR signature and a test gene expression, by setting an arbitrary threshold for assigning a cancer to one of two groups. Alternatively, in a preferred embodiment, the threshold for assignment is treated as a parameter, which can be used to quantify the confidence with which patients are assigned to each class. The threshold for assignment can be scaled to favor sensitivity or specificity, depending on the clinical scenario. In one such method, the CSR expression profile in a test sample is correlated to a vector representing the centroid of the differential expression of the reference CSR signature. The correlation value to the reference centroid generates a continuous score that can be scaled. In multivariate analysis, the CSR signature is an independent predictor of metastasis and death and provides a high level of prognostic information.

In an alternative embodiment, a decision tree algorithm is used to identify patients with clinically meaningful differences in outcome. At each node in the decision tree, all clinical risk factors and gene expression profiles are considered, patients with divergent outcomes using the dominant risk factor are identified, and reiterated the process on each subgroup until the patients or risk factors became exhausted.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A. The fibroblast common serum response. Genes with expression changes that demonstrate coordinate induction or repression by serum in fibroblasts from ten anatomic sites are shown. Each row represents a gene; each column represents a sample. The level of expression of each gene in each sample, relative to the mean level of expression of that gene across all the samples, is represented using a red-green color scale as shown in the key; gray indicates missing data. Representative genes with probable function in cell cycle progression (orange), matrix remodeling (blue), cytoskeletal rearrangement (red), and cell-cell signaling (black) are highlighted by colored text on the right. Three fetal lung fibroblast samples, cultured in low serum, which showed the most divergent expression patterns among these samples, are indicated by blue branches. FIG. 1B. Identification of cell cycle-regulated genes in the common serum response signature. The expression pattern of each of the genes in (A) during HeLa cell cycle over 46 h after synchronization by double thymidine block is shown. Transit of cells through S and M phases during the timecourse, verified by flow cytometry, is indicated below. Approximately one-quarter of genes demonstrate a periodic expression patterns and are therefore operationally annotated as cell cycle genes; the remainder of the genes are used in further analyses to define the CSR. FIG. 1C. Validation of annotation by temporal expression profiles. Timecourse of gene expression changes in a foreskin fibroblast culture after shifting from 0.1% to 10% FBS is shown. Global gene expression patterns were determined using cDNA microarrays containing 36,000 genes; genes whose transcript levels changed by at least 3-fold during the timecourse and those in (A) are displayed. The cell cycle genes identified in the analysis illustrated in (B) were found to have a distinct temporal expression pattern with coordinate upregulation at 12 h.

FIG. 3A. Expression patterns of CSR genes in a group of breast carcinomas and normal breast tissue. Genes and samples were organized by hierarchical clustering. The serum response of each gene is indicated on the right bar (red shows induced; green shows repressed by serum). Note the biphasic pattern of expression that allows each tumor sample to be classified as "activated" or "quiescent" based on the expression of the CSR genes. The previously identified tumor phenotype (color code) and p53 status (solid black box shows mutated; white box shows wildtype) are shown. Pairs of tumor samples from the same patient, obtained before and after surgery and chemotherapy, are connected by black lines under the dendrogram. Two primary tumor-lymph node metastasis pairs from the same patient are connected by purple lines. FIG. 3B. Kaplan-Meier survival curves for the two classes of tumors. Tumors with serum-activated CSR signature had worse disease-specific survival and relapse-free survival compared to tumors with quiescent CSR signature. Similar results were obtained whether performing classification using all breast tumors in this dataset or just the 58 tumors from the same clinical trial.

FIG. 6A. Unsupervised hierarchical clustering of 295 breast cancer samples using 442 available CSR genes. Each row represents a gene; each column represents a sample. The level of expression of each gene, in each sample, relative to the mean level of expression of that gene across all the samples, is represented using a red-green color scale as shown in the key; gray indicates missing data. The identity of each gene in the fibroblast serum response is shown on the right bar (red indicates activated; green indicates repressed by serum). The dendrogram at the top indicates the similarities among the samples in their expression of the CSR genes. Two main groups of tumors were observed: one group with similar expression to serum-activated fibroblasts, termed "Activated", and a second group with a reciprocal expression pattern of CSR genes, termed "Quiescent". Two small subsets of the quiescent group with more heterogeneous expression patterns are indicated by yellow bars. FIG. 6B, FIG. 6C. Kaplan-Meier survival curves for the two classes of tumors. Tumors with the activated wound response signature had worse overall survival (OS) and distant metastasis-free probability (DMFP) compared to tumors with a quiescent wound signature. 126 tumors were classified as Activated and 169 tumors as Quiescent. For Activated vs. Quiescent groups, 10 year OS are 50% vs. 84% ($p=5.6 \times 10^{-10}$) and 10 year DMFP are 51% vs. 75% ($p=8.6 \times 10^{-6}$), respectively.

FIG. 8A. Supervised wound signature adds prognostic information within the group of high risk patients identified by NIH consensus criteria. According to the NIH criteria, 284 patients are high risk and advised to undergo adjuvant chemotherapy; 72 patients had tumor-positive lymph nodes. Patients were classified using the serum activated fibroblast centroid (threshold=−0.15). 10 years DMFP for the Activated (N=221) vs. Quiescent (n=61) is 58% vs. 83% respectively (p=0.0002). FIG. 8B. Supervised wound signature stratifies St. Gallen criteria high risk patients. According to St. Gallen criteria, 271 patients are high risk and advised to undergo adjuvant treatment; 72 patients had tumor-positive lymph nodes. Using the supervised wound signature, the 10 years DMFP for the Activated (n=217) vs. Quiescent (n=56) group is 59% vs. 83% respectively (p=0.0005). FIG. 8C. Graphical representation of number of patients advised to undergo adjuvant systemic treatment and their eventual outcomes based on the supervised wound signature, the NIH, or St. Gallen Criteria in the 185 patients in this dataset that did not receive adjuvant chemotherapy. 40 patients had tumor-positive lymph nodes. Yellow indicates chemotherapy, blue indicates no chemotherapy. The bar at the left side shows which patients have developed distant metastasis as first event: Black indicates distant metastasis; white indicated no metastasis. Thus blue in the lower bar indicates the potentially under treated patients, yellow in the upper bar shows the potentially over treated patients.

FIG. 9A. Compendium of gene expression signatures in 295 breast tumors. Correlation value to canonical centroids of classes defined by intrinsic genes (Basal, luminal A, luminal B, ErbB2, vs. normal-like), by the 70 genes (Poor prognosis vs good), and by the wound signature (Activated vs. quiescent). Each row is a class; each column is a sample. Lower panel shows corresponding clinical outcomes; black vertical bar indicated death or metastasis as the first recurrence event. FIG. 9B. Summary of decision tree analysis. At each node, the dominant risk factor in multivariate analysis is used to segregate patients, and the process is repeated in each subgroup until patients or risk factors became exhausted. We found that the 70 gene signature was able to identify a group of patients with very good prognosis (group 0), and then the wound signature could divide the patients called "poor" by the 70 gene signature into those with moderate and significantly worse outcomes (groups 1 and 2). FIG. 9C. Distribution of 144 lymph node positive patients among the 3 groups defined in (B). Because the 70 gene signature was identified using a select subset of 60 patients with lymph node negative disease, the decision tree incorporating the 70 gene signature was performed on the independent lymph node positive subset to have an unbiased evaluation of risk prediction. Hazard ratios of metastasis risk after adjusting for all other factors listed in Table 1 are shown for the 3 subgroups stratified by the decision tree. FIG. 9D. Distant metastasis free probabilities of patients stratified by the decision tree analysis. 55, 32, and 57 patients are in group 0, 1, and 2 respectively, and 10 years DMFP for the 3 groups were 89%, 78%, and 47%, respectively ($p=6.94 \times 10^{-6}$).

FIG. 11A. Correlation of gene expression pattern in 295 breast cancer samples to the centroids of the 5 molecular subtypes. The strongest positive correlation of at least >0.10 determines the subtype (1). The individual patient braches are colored according to the subclass as defined by centroid correlation. Note that the basal subtype is most clearly defined, but >100 samples were not able to be assigned to any subtype. FIG. 11B. Tabular summary of patients in each tumor subtype with the activated wound response signature or poor prognosis 70-gene signature. Classification by the unsupervised wound response signature from FIG. 1 was applied for consistency. FIG. 11C. Improve risk stratification by integration of signatures. Patients in the ErbB2 (left) or Luminal B (right) subtypes were stratified by whether they have both the wound response and 70-gene signatures. Expression of the activated wound and poor prognosis 70-gene signatures conferred additive risk of death.

DETAILED DESCRIPTION OF THE EMBODIMENTS

Figure 1:
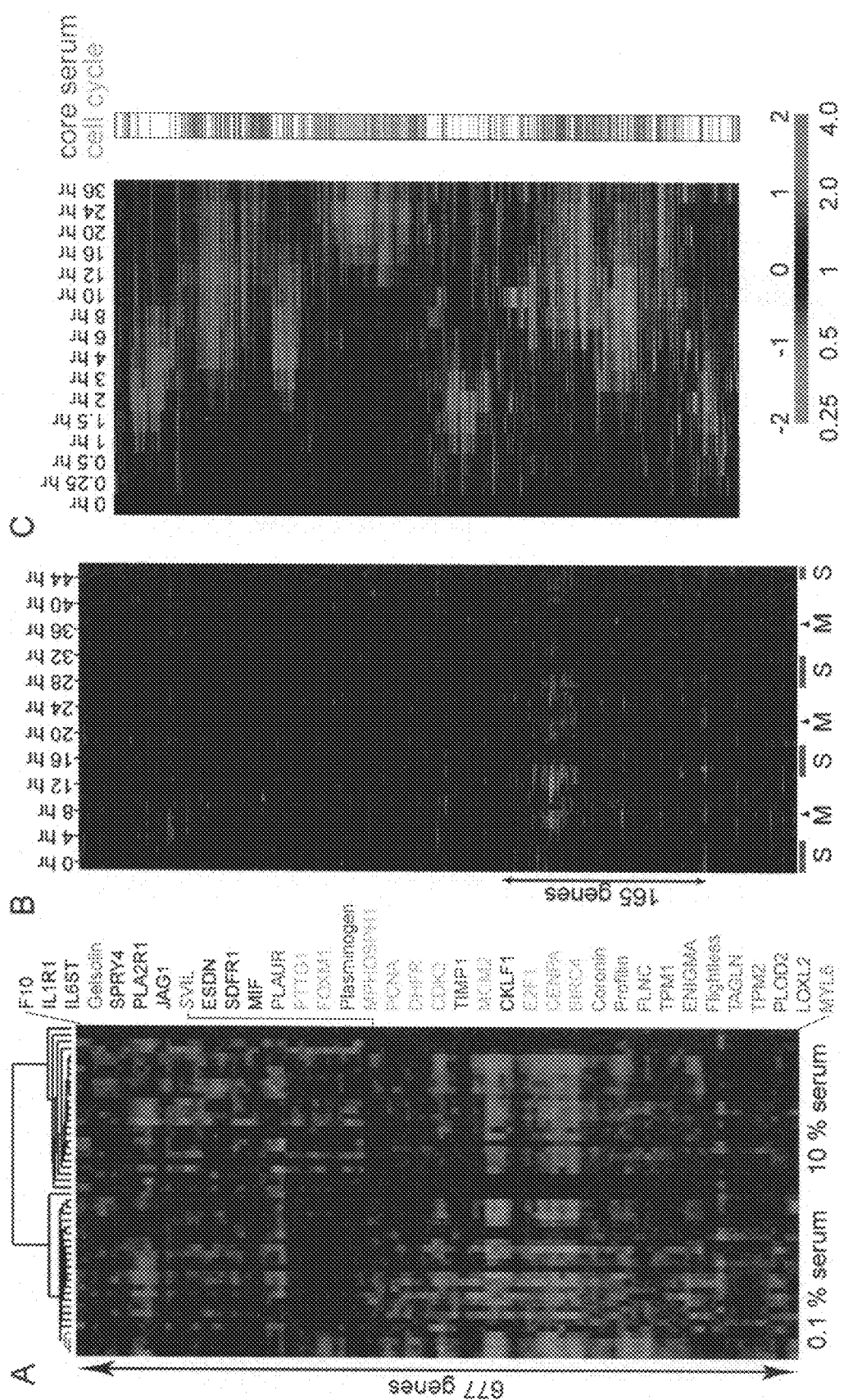
FIGS. 1A-1C. Identification and Annotation of a Common Serum Response in Fibroblasts.

Methods are provided for classification of cancers, particularly cancers derived from epithelial type cells, e.g. carcinomas. Classification according to CSR signature allows optimization of treatment, and determination of whether on whether to proceed with a specific therapy, and how to optimize dose, choice of treatment, and the like. Methods are provided for statistical analysis of expression profile data to determine whether a pattern of expression or response will be predictive of a phenotype of interest. Preferably the threshold for assignment is treated as a parameter, which can be used to quantify the confidence with which patients are assigned to each class. The threshold for assignment can be scaled to favor sensitivity or specificity, depending on the clinical scenario. In certain embodiments, the expression profile is determined using a microarray. In other embodiments the expression profile is determined by quantitative PCR or other quantitative methods for measuring mRNA.

The subject invention also provides a reference CSR expression profile for a response phenotype that is one of: (a) quiescent; or (b) induced; wherein said expression profile is recorded on a computer readable medium.

For quantitative PCR analysis, the subject invention provides a collection of gene specific primers, said collection comprising: gene specific primers specific for at least about 10, usually at least about 20 of the CSR genes, where in certain embodiments said collection comprises at least 50 gene specific primers, at least 100, or more. The subject invention also provides an array of probe nucleic acids immobilized on a solid support, said array comprising: a plurality of probe nucleic acid compositions, wherein each probe nucleic acid composition is specific for a CSR gene, where in certain embodiments said array further comprises at least one control nucleic acid composition.

The subject invention also provides a kit for use in determining the phenotype of a source of a nucleic acid sample, said kit comprising: at least one of: (a) an array as described above; or (b) a collection of gene specific primers as described above. The kit may further comprise a software package for data analysis of expression profiles.

The present application may make reference to information provided in Chang et al. (2004) PLoS Biology 2:206-214, including supplemental materials provided therein, which is herein specifically incorporated by reference in its entirety.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

As summarized above, the subject invention is directed to methods of classification of cancers, as well as reagents and kits for use in practicing the subject methods. The methods may also determine an appropriate level of treatment for a particular cancer.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

The invention finds use in the prevention, treatment, detection or research into any cancer, including prostrate, pancreas, colon, brain, lung, breast, bone, skin cancers. For example, the invention finds use in the prevention, treatment, detection of or research into gastrointestinal cancers, such as cancer of the anus, colon, esophagus, gallbladder, stomach, liver, and rectum; genitourinary cancers such as cancer of the penis, prostate and testes; gynecological cancers, such as cancer of the ovaries, cervix, endometrium, uterus, fallopian tubes, vagina, and vulva; head and neck cancers, such as hypopharyngeal, laryngeal, oropharyngeal cancers, lip, mouth and oral cancers, cancer of the salivary gland, cancer of the digestive tract and sinus cancer; metastatic cancer; sarcomas; skin cancer; urinary tract cancers including bladder, kidney and urethral cancers; endocrine system cancers, such as cancers of the thyroid, pituitary, and adrenal glands and the pancreatic islets; and pediatric cancers.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The terms "cancer", "neoplasm", "tumor", and "carcinoma", are used interchangeably herein to refer to cells that exhibit relatively autonomous growth, so that they exhibit an aberrant growth phenotype characterized by a significant loss of control of cell proliferation. In general, cells of interest for detection or treatment in the present application include pre-cancerous (e.g., benign), malignant, pre-metastatic, metastatic, and non-metastatic cells. Detection of cancerous cells is of particular interest.

The term "normal" as used in the context of "normal cell," is meant to refer to a cell of an untransformed phenotype or exhibiting a morphology of a non-transformed cell of the tissue type being examined.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" generally refers to a gene or gene product that, upon modulation of its activity (e.g., by modulation of expression, biological activity, and the like), can provide for modulation of the cancerous phenotype.

As used throughout, "modulation" is meant to refer to an increase or a decrease in the indicated phenomenon (e.g., modulation of a biological activity refers to an increase in a biological activity or a decrease in a biological activity).

A "CSR signature" is a dataset that has been obtained from multiple fibroblast cells, and provides information on the change in expression of a set of genes following fibroblast exposure to serum. A useful signature may be obtained from all or a part of the gene dataset, usually the signature will comprise information from at least about 20 genes, more usually at least about 30 genes, at least about 35 genes, at least about 45 genes, at least about 50 genes, or more, up to the complete dataset. Where a subset of the dataset is used, the subset may comprise upregulated genes, downregulated genes, or a combination thereof.

Various methods for analysis of a set of data may be utilized. In one embodiment, expression data is subjected to transformation and normalization. For example, ratios are generated by mean centering the expression data for each gene (by dividing the intensity measurement for each gene on a given array by the average intensity of the gene across all arrays), (2) then log-transformed (base 2) the resulting ratios, and (3) then median centered the expression data across arrays then across genes.

For cDNA microarray data, genes with fluorescent hybridization signals at least 1.5-fold greater than the local background fluorescent signal in the reference channel are considered adequately measured. The genes are centered by mean value within each dataset, and average linkage clustering carried out. The samples are segregated into two classes based on the first bifurcation in the hierarchical clustering "dendrogram". The clustering and reciprocal expression of serum-induced and serum repressed genes in tumor expression data allows two classes to be unambiguously assigned. Samples with generally high levels of expression of the serum-induced genes and low levels of expression of the serum-repressed genes, are classified as "activated", or "induced"; conversely, samples with generally high levels of expression of serum-repressed genes and low levels of expression of the serum-induced genes are classified as "quiescent".

In an alternative approach that quantifies the similarity of CSR gene expression in tumors vs. in cultured fibroblasts, the expression pattern of CSR genes in the fibroblast types is averaged to derive a single number for each gene. The Pearson correlation of the averaged fibroblast expression pattern with the cancer sample is then calculated. The Pearson correlation data allows the cancer sample to be assigned as having a positive correlation to the fibroblast serum-induced expression pattern, or as being anti-correlated with serum-induced expression. For example, using Pearson correlation of 0.2 as the cutoff, Cox-Mantel test confirmed that cancers with high correlation to fibroblast serum-induced expression of CSR genes demonstrate poorer disease-specific survival and relapse free survival.

To address the level of redundancy of CSR genes in achieving tumor classification, a shrunken centroid analysis has been applied, using Prediction Analysis of Microarrays (PAM). Using a 10-fold balanced leave-one-out training and testing procedure, it has been shown that approximately 5% of the CSR dataset is sufficient to recapitulate the classification A scaled approach may also be taken to the data analysis. Pearson correlation of the expression values of CSR genes of tumor samples to the serum-activated fibroblast centroid results in a quantitative score reflecting the wound response signature for each sample. The higher the correlation value, the more the sample resembles serum-activated fibroblasts ("activated" wound response signature). A negative correlation value indicates the opposite behavior and higher expression of the "quiescent" wound response signature. The threshold for the two classes can be moved up or down from zero depending on the clinical goal. For example, sensitivity and specificity for predicting metastasis as the first recurrence event has been calculated for every threshold between −1 and +1 for the correlation score in 0.05 increments. The threshold value of negative 0.15 correlation gave 90% sensitivity for metastasis prediction in the training set, and had equivalent performance in the test-set.

To provide significance ordering, the false discovery rate (FDR) may be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5116-21, herein incorporated by reference). The set of null distribution is obtained by: permuting the values of each profile for all available profiles; calculating the pairwise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data may be subjected to non-supervised hierarchical clustering to reveal relationships among profiles. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions.

The analysis may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as drug discovery, analysis of interactions between cellular components, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language may be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The CSR dataset may include expression data, for example as set forth in the attached table of sequences. Such information may include, for example:

| | |
|---|---|
| Imputation Engine | Row Average Imputer |
| Data Type | Two Class, unpaired data |
| Data in log scale? | TRUE |
| Number of Permutations | 100 |
| Blocked Permutation? | FALSE |
| RNG Seed | 1234567 |
| (Delta, Fold Change) | (0.93749,) |
| (Upper Cutoff, Lower Cutoff) | (1.10713, −2.02782) |
| Computed Quantities | |
| Computed Exchangeability Factor S0 | 0.088187083 |
| S0 percentile | 0 |
| False Significant Number (Median, 90 percentile) | (3.54839, 6.48387) |
| False Discovery Rate (Median, 90 percentile) | (3.28554, 6.00358) |
| Pi0Hat | 0.32258 |

Significant Upregulated Genes

| Gene Name | Gene ID | Score (d) | Numerator (r) | Denominator (s + s0) | Fold Change | q-value (%) |
|---|---|---|---|---|---|---|
| Hs.77152 | minichromosome maintenance deficient (*S. cerevisiae*) 7 (MCM7) | 6.24266579 | 0.88558576 | 0.14186019 | 1.87394 | 0.27199782 |
| Hs.283532 | uncharacterized bone marrow protein BM039 (BM039) | 6.17372963 | 1.36598291 | 0.22125733 | 2.72859 | 0.27199782 |
| Hs.6879 | DC13 protein (DC13) | 6.16636831 | 0.88302988 | 0.14320096 | 1.84812 | 0.27199782 |
| Hs.1600 | *Homo sapiens* mRNA for KIAA0098 protein, partial cds. (CCT5) | 5.64212527 | 0.82474861 | 0.14617694 | 1.91743 | 0.27199782 |
| Hs.179718 | v-myb avian myeloblastosis viral oncogene homolog-like 2 (MYBL2) | 5.42648948 | 0.65247642 | 0.12023914 | 1.55694 | 0.27199782 |
| Hs.99910 | phosphofructokinase, platelet (PFKP) | 5.30873252 | 1.4605137 | 0.27511533 | 3.20727 | 0.27199782 |
| Hs.80506 | small nuclear ribonucleoprotein polypeptide A' (SNRPA1) | 5.01401357 | 0.84545044 | 0.1686175 | 1.85129 | 0.27199782 |
| Hs.38178 | *Homo sapiens* cDNA: FLJ23468 fis, clone HSI11603 (FLJ23468) | 4.97750953 | 1.18388499 | 0.23784686 | 2.07999 | 0.27199782 |
| Hs.119192 | H2A histone family, member Z (H2AFZ) | 4.83660369 | 0.71736233 | 0.14831943 | 1.59929 | 0.27199782 |
| Hs.78619 | gamma-glutamyl hydrolase (conjugase, folylpolygammaglutamyl hydrolase) (GGH) | 4.65988643 | 1.25372308 | 0.26904585 | 2.27496 | 0.27199782 |
| Hs.76084 | lamin B2 (LMNB2) | 4.36081861 | 0.54756893 | 0.12556563 | 1.47445 | 0.27199782 |
| Hs.301005 | purine-rich element binding protein B (PURB) | 4.32034591 | 0.58292036 | 0.13492447 | 1.51299 | 0.27199782 |
| Hs.104650 | hypothetical protein FLJ10292 (FLJ10292) | 4.31473432 | 0.68766639 | 0.1593763 | 1.71836 | 0.27199782 |
| Hs.30738 | hypothetical protein FLJ10407 (FLJ10407) | 4.26103924 | 0.65407063 | 0.15350026 | 1.60324 | 0.27199782 |
| Hs.293943 | ESTs, Highly similar to type III adenylyl cyclase [*H. sapiens*] (MGC11266) | 4.12208931 | 0.52894843 | 0.12832047 | 1.46766 | 0.27199782 |
| Hs.172052 | serine/threonine kinase 18 (STK18) | 4.10230318 | 0.96344313 | 0.2348542 | 1.82998 | 0.27199782 |
| Hs.95734 | uridine monophosphate kinase (UMPK) | 4.09493539 | 0.63077454 | 0.15403773 | 1.61626 | 0.27199782 |
| Hs.184693 | transcription elongation factor B (SIII), polypeptide 1 (15 kD, elongin C) (TCEB1) | 4.04725975 | 0.56282743 | 0.13906383 | 1.46422 | 0.27199782 |
| Hs.109059 | mitochondrial ribosomal protein L12 (MRPL12) | 3.81864555 | 0.5775517 | 0.15124517 | 1.58426 | 0.27199782 |
| Hs.71465 | squalene epoxidase (SQLE) | 3.71603394 | 0.78959138 | 0.21248229 | 1.65688 | 0.27199782 |
| Hs.72160 | AND-1 protein (AND-1) | 3.71136957 | 0.4482071 | 0.12076596 | 1.33466 | 0.27199782 |
| Hs.74619 | proteasome (prosome, macropain) 26S subunit, non-ATPase, 2 (PSMD2) | 3.63896765 | 0.45566206 | 0.1252174 | 1.42331 | 0.27199782 |
| Hs.151734 | nuclear transport factor 2 (placental protein 15) (PP15) | 3.61590108 | 0.48679812 | 0.13462706 | 1.42652 | 0.27199782 |
| Hs.184641 | delta-6 fatty acid desaturase (FADS2) | 3.55280237 | 1.2177139 | 0.34274744 | 2.18507 | 0.27199782 |
| Hs.254105 | MYC promoter-binding protein 1 (MPB1) | 3.48008378 | 0.60549865 | 0.17398968 | 1.69499 | 0.27199782 |
| Hs.233952 | proteasome (prosome, macropain) subunit, alpha type, 7 (PSMA7) | 3.42861708 | 0.41988721 | 0.12246547 | 1.35873 | 0.27199782 |
| Hs.17377 | coronin, actin-binding protein, 1C (CORO1C) | 3.40013908 | 0.57434988 | 0.16891953 | 1.56183 | 0.27199782 |
| Hs.81412 | lipin 1 (LPIN1) | 3.38319265 | 0.54851461 | 0.16212929 | 1.55251 | 0.27199782 |
| Hs.335918 | farnesyl diphosphate synthase (farnesyl pyrophosphate synthetase, dimethylallyltranstransferase, geranyltranstransferase) (FDPS) | 3.37338054 | 0.41139393 | 0.12195302 | 1.33744 | 0.27199782 |
| Hs.41270 | procollagen-lysine, 2-oxoglutarate 5-dioxygenase (lysine hydroxylase) 2 (PLOD2) | 3.32204115 | 0.94547776 | 0.28460748 | 1.91049 | 0.27199782 |
| Hs.167246 | P450 (cytochrome) oxidoreductase (POR) | 3.28545393 | 0.40508206 | 0.12329561 | 1.34948 | 0.27199782 |
| Hs.24763 | RAN binding protein 1 (RANBP1) | 3.28285844 | 0.40644954 | 0.12380965 | 1.36186 | 0.27199782 |
| Hs.25292 | ribonuclease HI, large subunit (RNASEHI) | 3.2764898 | 0.49781887 | 0.15193665 | 1.45033 | 0.27199782 |
| Hs.21331 | hypothetical protein FLJ10036 (FLJ10036) | 3.26352442 | 0.36796159 | 0.11274976 | 1.29306 | 0.27199782 |
| Hs.118638 | non-metastatic cells 1, protein (NM23A) expressed in (NME1) | 3.20843494 | 0.7648118 | 0.23837535 | 2.25967 | 0.27199782 |
| Hs.425427 | hypothetical protein FLJ20425 (FLJ20425) | 3.19229612 | 0.38036509 | 0.11915094 | 1.33523 | 0.27199782 |
| Hs.39504 | ESTs | 3.18081739 | 0.41003025 | 0.12890719 | 1.34102 | 0.27199782 |
| Hs.76038 | isopentenyl-diphosphate delta isomerase (IDl1) | 3.17655837 | 0.56842601 | 0.17894398 | 1.44489 | 0.27199782 |
| Hs.13413 | *Homo sapiens* clone 24463 mRNA sequence | 3.14715276 | 0.4584221 | 0.14566249 | 1.44799 | 0.27199782 |
| Hs.300592 | v-myb avian myeloblastosis viral oncogene homolog-like 1 (MYBL1) | 3.13335532 | 0.99922149 | 0.31889824 | 1.87750 | 0.27199782 |
| Hs.30928 | DNA segment on chromosome 19 (unique) 1177 expressed sequence (D19S1177E) | 3.10800899 | 0.37209625 | 0.11972174 | 1.29528 | 0.27199782 |
| Hs.254105 | enolase 1, (alpha) (ENO1) | 3.10300284 | 0.76299163 | 0.24588815 | 1.74559 | 0.27199782 |
| Hs.20295 | CHK1 (checkpoint, (*S. pombe*) homolog (CHEK1) | 3.06131965 | 0.43883572 | 0.14334855 | 1.34487 | 0.27199782 |
| Hs.179657 | plasminogen activator, urokinase receptor (PLAUR) | 2.99444759 | 0.52176544 | 0.1742443 | 1.46068 | 0.27199782 |
| Hs.301613 | JTV1 gene (JTV1) | 2.90806789 | 0.33659929 | 0.1157467 | 1.28442 | 0.27199782 |
| Hs.132898 | *Homo sapiens* clone 23716 mRNA sequence (FADS1) | 2.90005517 | 0.70158255 | 0.24192041 | 1.76617 | 0.27199782 |
| Hs.90421 | PRO2463 protein (PRO2463) | 2.86786719 | 0.35798348 | 0.12482568 | 1.27507 | 0.27199782 |
| Hs.144407 | hypothetical protein FLJ10956 (FLJ10956) | 2.80960009 | 0.43376209 | 0.15438571 | 1.31539 | 0.27199782 |
| Hs.374421 | ESTs, Moderately similar to IP63 protein [*R. norvegicus*] (KIAA0203) | 2.74678832 | 0.37934929 | 0.13810649 | 1.34755 | 0.27199782 |
| Hs.1063 | small nuclear ribonucleoprotein polypeptide C (SNRPC) | 2.73871301 | 0.31259621 | 0.11413982 | 1.26394 | 0.27199782 |
| Hs.274350 | BAF53 (BAF53A) | 2.71855649 | 0.40765963 | 0.14995445 | 1.33805 | 0.27199782 |
| Hs.180403 | ESTs | 2.68910682 | 0.36600076 | 0.13610495 | 1.32377 | 0.27199782 |
| Hs.180403 | STRIN protein (STRIN) | 2.66320957 | 0.35379143 | 0.13284401 | 1.31840 | 0.27199782 |
| Hs.239189 | *Homo sapiens* glutaminase isoform M precursor, mRNA, complete cds | 2.65063913 | 0.63428913 | 0.23929667 | 4.62885 | 0.27199782 |
| Hs.274170 | Opa-interacting protein 2 (OIP2) | 2.64516217 | 0.31482978 | 0.11902097 | 1.24892 | 0.27199782 |
| Hs.433434 | proteasome (prosome, macropain) subunit, beta type, 7 (PSMB7) | 2.6052457 | 0.3165641 | 0.12151027 | 1.28888 | 0.27199782 |
| Hs.136644 | CS box-containing WD protein (LOC55884) | 2.58087422 | 0.33912871 | 0.13140071 | 1.28953 | 0.27199782 |
| Hs.709 | deoxycytidine kinase (DCK) | 2.57369859 | 0.37013597 | 0.14381481 | 1.29759 | 0.27199782 |
| Hs.29088 | ESTs, Weakly similar to ARL3 HUMAN ADP-RIBOSYLATION FACTOR-LIKE PROTEIN 3 [*H. sapiens*] | 2.52610098 | 0.48704394 | 0.19280462 | 1.43699 | 0.27199782 |
| Hs.5957 | *Homo sapiens* clone 24416 mRNA sequence | 2.52016003 | 0.39965241 | 0.15858215 | 1.38929 | 0.27199782 |

-continued

Significant Upregulated Genes

| Gene Name | Gene ID | Score (d) | Numerator (r) | Denominator (s + s0) | Fold Change | q-value (%) |
|---|---|---|---|---|---|---|
| Hs.179565 | minichromosome maintenance deficient (*S. cerevisiae*) 3 (MCM3) | 2.4894397 | 0.28549077 | 0.11468073 | 1.24454 | 0.27199782 |
| Hs.73965 | splicing factor, arginine/serine-rich 2 (SFRS2) | 2.47543942 | 0.24756852 | 0.10000993 | 1.16457 | 0.27199782 |
| Hs.388 | nudix (nucleoside diphosphate linked moiety X)-type motif 1 (NUDT1) | 2.4611642 | 0.27071923 | 0.10999641 | 1.21357 | 0.27199782 |
| Hs.79172 | solute carrier family 25 (mitochondrial carrier; adenine nucleotide translocator), member 5 (SLC25A5) | 2.4483298 | 0.4108956 | 0.1678269 | 1.30174 | 0.27199782 |
| Hs.3828 | mevalonate (diphospho) decarboxylase (MVD) | 2.42513279 | 0.23018084 | 0.09491474 | 1.17207 | 0.27199782 |
| Hs.153179 | fatty acid binding protein 5 (psoriasis-associated) (FABP5) | 2.41843302 | 0.59851464 | 0.24748035 | 2.17670 | 0.27199782 |
| Hs.334612 | small nuclear ribonucleoprotein polypeptide E (SNRPE) | 2.40951258 | 0.38600455 | 0.16020026 | 1.37147 | 0.27199782 |
| Hs.267288 | hypothetical protein (HSPC228) | 2.40575144 | 0.54178947 | 0.22520592 | 1.40436 | 0.27199782 |
| Hs.81361 | heterogeneous nuclear ribonucleoprotein A/B (HNRPAB) | 2.38340841 | 0.28992098 | 0.12164133 | 1.23242 | 0.27199782 |
| Hs.15159 | chemokine-like factor 3, alternatively spliced (LOC51192) | 2.29576393 | 0.26653362 | 0.11609801 | 1.20594 | 0.27199782 |
| Hs.170328 | moesin (MSN) | 2.27516047 | 0.36787244 | 0.16169076 | 1.39934 | 0.27199782 |
| Hs.75721 | profilin 1 (PFN1) | 2.25143981 | 0.22518119 | 0.10001653 | 1.17696 | 0.27199782 |
| Hs.159226 | hyaluronan synthase 2 (HAS2) | 2.24168105 | 0.43338901 | 0.19333215 | 1.40128 | 0.27199782 |
| Hs.115474 | replication factor C (activator 1) 3 (38 kD) (RFC3) | 2.22895495 | 0.31247982 | 0.14019118 | 1.17852 | 0.27199782 |
| Hs.173255 | small nuclear ribonucleoprotein polypeptide A (SNRPA) | 2.21153601 | 0.20861507 | 0.0943304 | 1.15803 | 0.27199782 |
| Hs.236204 | nuclear pore complex protein (NUP107) | 2.19861709 | 0.30100287 | 0.13690554 | 1.23597 | 0.27199782 |
| Hs.333212 | retinal degeneration B beta (RDGBB) | 2.17600694 | 0.31922978 | 0.14670439 | 1.25754 | 0.27199782 |
| Hs.115660 | hypothetical protein FLJ12810 (FLJ12810) | 2.17426911 | 0.29687245 | 0.13654117 | 1.23752 | 0.27199782 |
| Hs.21293 | UDP-N-acteylglucosamine pyrophosphorylase 1 (UAP1) | 2.16628553 | 0.31945677 | 0.14746753 | 1.22148 | 0.27199782 |
| Hs.232400 | heterogeneous nuclear ribonucleoprotein A2/B1 (HNRPA2B1) | 2.16025042 | 0.22190382 | 0.10272134 | 1.16264 | 0.27199782 |
| Hs.6441 | tissue inhibitor of metalloproteinase 2 (TIMP2) | 2.12233563 | 0.32258277 | 0.15199423 | 1.28837 | 0.27199782 |
| Hs.6679 | hHDC for homolog of *Drosphila* headcase (LOC51696) | 2.09642466 | 0.34282628 | 0.16352902 | 1.24711 | 0.27199782 |
| Hs.251754 | secretory leukocyte protease inhibitor (antileukoproteinase) (SLPI) | 2.07936889 | 0.33592311 | 0.16155051 | 1.34579 | 0.27199782 |
| Hs.50848 | hypothetical protein FLJ20331 (FLJ20331) | 2.07860508 | 0.46243275 | 0.22247263 | 1.26114 | 0.27199782 |
| Hs.15159 | transmembrane proteolipid (HSPC224) | 2.06713387 | 0.28015069 | 0.13552615 | 1.21214 | 0.27199782 |
| Hs.77910 | 3-hydroxy-3-methylglutaryl-Coenzyme A synthase 1 (soluble) (HMGCS1) | 2.06080302 | 0.54351413 | 0.263739 | 1.32792 | 0.27199782 |
| Hs.99185 | polymerase (DNA directed), epsilon 2 (POLE2) | 2.03931226 | 0.32387025 | 0.15881347 | 1.22127 | 0.50485927 |
| Hs.132898 | fatty acid desaturase 1 (FADS1) | 2.03113336 | 0.44728926 | 0.22021659 | 1.27983 | 0.50485927 |
| Hs.4209 | mitochondrial ribosomal protein L37 (MRPL37) | 2.01731461 | 0.29897245 | 0.14820318 | 1.25048 | 0.50485927 |
| Hs.132004 | cardiotrophin-like cytokine; neurotrophin-1/B-cell stimulating factor-3 (CLC) | 1.97290698 | 0.27794123 | 0.14087903 | 1.20693 | 0.50485927 |
| Hs.21635 | tubulin, gamma 1 (TUBG1) | 1.96841526 | 0.30936059 | 0.15716226 | 1.25460 | 0.50485927 |
| Hs.283077 | ESTs, Weakly similar to I38428 T-complex protein 10A [*H. sapiens*] (BM032) | 1.96732498 | 0.46245778 | 0.23506934 | 1.33738 | 0.50485927 |
| Hs.83753 | small nuclear ribonucleoprotein polypeptides B and B1 (SNRPB) | 1.95649714 | 0.24064175 | 0.12299622 | 1.18166 | 0.50485927 |
| Hs.37616 | Human D9 splice variant B mRNA, complete cds (D9 splice variant A) | 1.9478297 | 0.41887173 | 0.21504536 | 1.58924 | 0.69252078 |
| Hs.433410 | menage a trois 1 (CAK assembly factor) (MNAT1) | 1.93937463 | 0.30730525 | 0.15845585 | 1.25912 | 0.69252078 |
| Hs.250758 | proteasome (prosome, macropain) 26S subunit, ATPase, 3 (PSMC3) | 1.93361382 | 0.21467994 | 0.11102524 | 1.15020 | 0.69252078 |
| Hs.279918 | hypothetical protein (HSPC111) | 1.92490899 | 0.26037618 | 0.13526675 | 1.20325 | 0.69252078 |
| Hs.115823 | ribonuclease P, 40 kD subunit (RPP40) | 1.89539827 | 0.45966533 | 0.24251649 | 1.25592 | 0.69252078 |
| Hs.234279 | microtubule-associated protein, RP/EB family, member 1 (MAPRE1) | 1.88830139 | 0.21898904 | 0.11597144 | 1.17501 | 0.69252078 |
| Hs.366 | 6-pyruvoyltetrahydropterin synthase (PTS) | 1.87341499 | 0.24038499 | 0.1283138 | 1.21664 | 0.69252078 |
| Hs.433317 | eukaryotic translation initiation factor 4E binding protein 1 (EIF4EBP1) | 1.86783064 | 0.33986461 | 0.18195686 | 1.13648 | 0.69252078 |
| Hs.34045 | hypothetical protein FLJ20764 (FLJ20764) | 1.86462266 | 0.41839215 | 0.22438435 | 1.23506 | 0.69252078 |
| Hs.55097 | HSPC007 protein (MRPS28) | 1.85812075 | 0.29812259 | 0.16044307 | 1.26125 | 0.69252078 |
| Hs.283077 | centrosomal P4.1-associated protein; uncharacterized bone marrow protein BM032 (BM032) | 1.83925243 | 0.21972973 | 0.11946687 | 1.18278 | 1.28369705 |
| Hs.75231 | solute carrier family 16 (monocarboxylic acid transporters), member 1 (SLC16A1) | 1.81687376 | 0.51059437 | 0.28102908 | 1.48465 | 1.28369705 |
| Hs.3745 | milk fat globule-EGF factor 8 protein (MFGE8) | 1.80398181 | 0.35793403 | 0.19841333 | 1.73420 | 1.28369705 |
| Hs.9081 | phenylalanyl-tRNA synthetase beta-subunit (PheHB) | 1.7997857 | 0.22943372 | 0.12747836 | 1.13698 | 1.28369705 |
| Hs.5957 | ESTs | 1.79248137 | 0.30336788 | 0.16924465 | 1.26912 | 1.28369705 |
| Hs.30035 | splicing factor, arginine/serine-rich (transformer 2 *Drosophila* homolog) 10 (SFRS10) | 1.78531703 | 0.21351528 | 0.11959516 | 1.14083 | 1.28369705 |
| Hs.56205 | insulin induced gene 1 (INSIG1) | 1.7620129 | 0.42491935 | 0.24115564 | 1.25021 | 1.28369705 |
| Hs.173374 | *Homo sapiens* unknown mRNA | 1.74582269 | 0.27815506 | 0.15932607 | 1.26120 | 1.28369705 |
| Hs.389371 | stromal cell derived factor receptor 1 (SDFR1) | 1.71762102 | 0.30681408 | 0.17862734 | 1.43167 | 1.28369705 |
| Hs.82109 | syndecan 1 (SDC1) | 1.68910218 | 0.36091597 | 0.21367326 | 1.31602 | 2.08629682 |
| Hs.346868 | nucleolar protein p40; homolog of yeast EBNA1-binding protein (P40) | 1.63693648 | 0.20420155 | 0.12474617 | 1.17604 | 2.08629682 |
| Hs.1600 | ESTs | 1.62965745 | 0.32896037 | 0.2018586 | 1.46752 | 2.08629682 |
| Hs.119597 | stearoyl-CoA desaturase (delta-9-desaturase) (SCD) | 1.62297238 | 0.46874655 | 0.28881979 | 1.13094 | 2.08629682 |
| Hs.355899 | type I transmembrane protein Fn14 (FN14) | 1.62078519 | 0.24764974 | 0.15279615 | 1.18802 | 2.08629682 |
| Hs.44235 | hypothetical protein from clone 24774 (LOC57213) | 1.61654079 | 0.2384004 | 0.14747565 | 1.14323 | 2.08629682 |
| Hs.26812 | ESTs | 1.61385953 | 0.2589403 | 0.16044785 | 1.24737 | 2.08629682 |
| Hs.111632 | Lsm3 protein (LSM3) | 1.60108709 | 0.19531168 | 0.12198692 | 1.14935 | 2.08629682 |
| Hs.77254 | chromobox homolog 1 (*Drosphila* HP1 beta) (CBX1) | 1.57781631 | 0.26629665 | 0.16877545 | 1.22826 | 2.08629682 |

-continued

Significant Upregulated Genes

| Gene Name | Gene ID | Score (d) | Numerator (r) | Denominator (s + s0) | Fold Change | q-value (%) |
|---|---|---|---|---|---|---|
| Hs.94262 | p53-inducible ribonucleotide reductase small subunit 2 homolog (p53R2) | 1.57068021 | 0.25133806 | 0.16001861 | 1.24555 | 2.08629682 |
| Hs.117950 | multifunctional polypeptide similar to SAICAR synthetase and AIR carboxylase (ADE2H1) | 1.55751281 | 0.2398798 | 0.15401465 | 1.23805 | 2.08629682 |
| Hs.4295 | proteasome (prosome, macropain) 26S subunit, non-ATPase, 12 (PSMD12) | 1.55435183 | 0.26558351 | 0.17086447 | 1.14969 | 2.08629682 |
| Hs.89718 | spermine synthase (SMS) | 1.53674434 | 0.20250514 | 0.13177542 | 1.15724 | 4.44342297 |
| Hs.149155 | voltage-dependent anion channel 1 (VDAC1) | 1.51556741 | 0.19699455 | 0.12998072 | 1.15767 | 4.44342297 |
| Hs.433750 | eukaryotic translation initiation factor 4 gamma, 1 (EIF4G1) | 1.49744535 | 0.13959027 | 0.09321894 | 1.10967 | 4.44342297 |
| Hs.91579 | Homo sapiens clone 23783 mRNA sequence | 1.49466048 | 0.15552436 | 0.1040533 | 1.11050 | 4.44342297 |
| Hs.46967 | HSPCO34 protein (LOC51668) | 1.48595392 | 0.19758214 | 0.13296653 | 1.16297 | 4.44342297 |
| Hs.266940 | t-complex-associated-testis-expressed 1-like 1 (TCTEL1) | 1.43257635 | 0.23204568 | 0.16197788 | 1.21344 | 4.44342297 |
| Hs.10056 | ESTs | 1.42970833 | 0.44285313 | 0.30975068 | 3.67816 | 4.44342297 |
| Hs.172792 | ESTs | 1.41090654 | 0.37444214 | 0.26539117 | 1.27879 | 4.44342297 |
| Hs.197335 | aminopeptidase (LOC51670) | 1.41050169 | 0.2422019 | 0.1717133 | 1.25220 | 4.44342297 |
| Hs.279582 | GTP-binding protein Sara (LOC51128) | 1.40252835 | 0.19847846 | 0.14151476 | 1.13829 | 4.44342297 |
| Hs.102696 | MCT-1 protein (MCT-1) | 1.39380428 | 0.1631652 | 0.11706464 | 1.10856 | 4.44342297 |
| Hs.42484 | hypothetical protein FLJ10618 (FLJ10618) | 1.37258461 | 0.22462694 | 0.16365253 | 1.15279 | 4.44342297 |
| Hs.76244 | spermidine synthase (SRM) | 1.35853091 | 0.19973084 | 0.14701972 | 1.13148 | 4.44342297 |
| Hs.333212 | ESTs | 1.35708393 | 0.13601822 | 0.1002283 | 1.11370 | 4.44342297 |
| Hs.11170 | SYT interacting protein (RBM14) | 1.3563745 | 0.11698688 | 0.08624969 | 1.08326 | 4.44342297 |
| Hs.288348 | KIAA1305 protein (KIAA1305) | 1.33367078 | 0.30095186 | 0.22565678 | 1.14116 | 4.44342297 |
| Hs.11169 | Homo sapiens Gene 33/Mig-6 (MIG-6), mRNA. (MIG-6) | 1.32515933 | 0.15703707 | 0.11850429 | 1.14463 | 4.44342297 |
| Hs.295944 | tissue factor pathway inhibitor 2 (TFPI2) | 1.3230227 | 0.33326341 | 0.25189546 | 1.49192 | 4.44342297 |
| Hs.389371 | stromal cell derived factor receptor 1 (SDFR1) | 1.31414091 | 0.1987656 | 0.15125136 | 1.18734 | 4.44342297 |
| Hs.9075 | serine/threonine kinase 17a (apoptosis-inducing) (STK17A) | 1.28877841 | 0.14256009 | 0.11061645 | 1.13415 | 4.44342297 |
| Hs.106148 | Homo sapiens mRNA; cDNA DKFZp434G0972 (from clone DKFZp434G0972) | 1.28509439 | 0.36114986 | 0.28102983 | 1.63974 | 4.44342297 |
| Hs.227730 | integrin, alpha 6 (ITGA6) | 1.28204469 | 0.31747304 | 0.24763024 | 1.37915 | 4.44342297 |
| Hs.11169 | Gene 33/Mig-6 (MIG-6) | 1.27685277 | 0.31371838 | 0.24569659 | 1.44504 | 4.44342297 |
| Hs.24983 | hypothetical protein from EUROIMAGE 2021883 (LOC56926) | 1.26222375 | 0.30328897 | 0.24028147 | 1.12534 | 4.44342297 |
| Hs.28707 | signal sequence receptor, gamma (translocon-associated protein gamma) (SSR3) | 1.25401667 | 0.15400059 | 0.12280586 | 1.12298 | 4.44342297 |
| Hs.250655 or | prothymosin, alpha (gene sequence 28) (PTMA) | 1.25013811 | 0.15278419 | 0.12221385 | 1.14648 | 4.44342297 |
| Hs.31297 | Homo sapiens cDNA: FLJ23001 fis, clone LNG00288 (FLJ23462) | −5.87108213 | −1.17785288 | 0.20061938 | 0.40677 | 0.27199782 |
| Hs.214646 | hypothetical protein FLJ13052 (FLJ13052) | −5.45560694 | −0.79779673 | 0.14623428 | 0.60769 | 0.27199782 |
| Hs.69771 | B-factor, properdin (BF) | −5.28613088 | −1.73341725 | 0.32791796 | 0.33658 | 0.27199782 |
| Hs.17567 | ESTs | −4.84061065 | −0.59847496 | 0.12363625 | 0.66607 | 0.27199782 |
| Hs.44829 | ESTs | −4.82700577 | −1.01645627 | 0.21057697 | 0.61349 | 0.27199782 |
| Hs.87246 | Bcl-2 binding component 3 (BBC3) | −4.8121198 | −0.68938083 | 0.14325928 | 0.62209 | 0.27199782 |
| Hs.93659 | protein disulfide isomerase related protein (calcium-binding protein, intestinal-related) (ERP70) | −4.80394482 | −0.68440459 | 0.14246721 | 0.60608 | 0.27199782 |
| Hs.156667 | KIAA1536 protein (KIAA1536) | −4.6733759 | −0.41017061 | 0.08776752 | 0.74931 | 0.27199782 |
| Hs.5944 | solute carrier family 11 (proton-coupled divalent metal ion transporters), member 3 (SLC11A3) | −4.46800149 | −1.41402485 | 0.31647815 | 0.39927 | 0.27199782 |
| Hs.283749 | ribonuclease, RNase A family, 4 (RNASE4) | −4.36896299 | −0.84874774 | 0.19426755 | 0.57795 | 0.27199782 |
| Hs.11590 | cathepsin F (CTSF) | −4.19131852 | −0.70543451 | 0.16830849 | 0.62499 | 0.27199782 |
| Hs.7041 | ESTs | −4.11393854 | −0.65502996 | 0.15922211 | 0.58871 | 0.27199782 |
| Hs.28264 | Homo sapiens mRNA; cDNA DKFZp564L0822 (from clone DKFZp564L0822) | −3.91296053 | −0.67544996 | 0.17261865 | 0.58652 | 0.27199782 |
| Hs.250493 | zinc finger protein 219 (ZNF219) | −3.85823683 | −0.60453388 | 0.15668657 | 0.68066 | 0.27199782 |
| Hs.8768 | ESTs | −3.82051422 | −0.61907901 | 0.16204076 | 0.63132 | 0.27199782 |
| Hs.31297 | Homo sapiens cDNA: FLJ23462 fis, clone HSI08475 (FLJ23462) | −3.75088735 | −0.84605869 | 0.22556228 | 0.45121 | 0.27199782 |
| Hs.3631 | immunoglobulin (CD79A) binding protein 1 (IGBP1) | −3.74866875 | −0.48240754 | 0.12868769 | 0.71929 | 0.27199782 |
| Hs.356688 | ESTs, Weakly similar to developmentally regulated protein [R. norvegicus] (PNN) | −3.59357898 | −0.58418745 | 0.16256425 | 0.74044 | 0.27199782 |
| Hs.17466 | retinoic acid receptor responder (tazarotene induced) 3 (RARRES3) | −3.56638824 | −1.03024952 | 0.28887755 | 0.53964 | 0.27199782 |
| Hs.257267 | Homo sapiens cDNA FLJ13335 fis, clone OVARC1001861 (FYCO1) | −3.35767437 | −0.45015031 | 0.1340661 | 0.73535 | 0.27199782 |
| Hs.9908 | nitrogen fixation cluster-like (NIFU) | −3.30596913 | −0.35890193 | 0.10856179 | 0.77438 | 0.27199782 |
| Hs.75497 | Homo sapiens cDNA: FLJ22139 fis, clone HEP20959 | −3.29072247 | −0.67872808 | 0.20625504 | 0.74088 | 0.27199782 |
| Hs.304682 | cystatin C (amyloid angiopathy and cerebral hemorrhage) (CST3) | −3.26935192 | −0.42070782 | 0.12868233 | 0.73051 | 0.27199782 |
| Hs.82065 | interleukin 6 signal transducer (gp130, oncostatin M receptor) (IL6ST) | −3.22438897 | −0.66790917 | 0.20714287 | 0.72860 | 0.27199782 |
| Hs.111099 | ESTs, Weakly similar to alpha-1 type I collagen [H. sapiens] | −3.21947708 | −0.43288862 | 0.1344593 | 0.74536 | 0.27199782 |
| Hs.433434 | ESTs | −3.10985036 | −0.34821038 | 0.11197014 | 0.78988 | 0.27199782 |
| Hs.171825 | basic helix-loop-helix domain containing, class B, 2 (BHLHB2) | −3.07360073 | −0.53281194 | 0.17335106 | 0.68365 | 0.27199782 |
| Hs.10346 | hypothetical protein FLJ20367 (FLJ20367) | −3.06586489 | −0.41307731 | 0.13473435 | 0.73270 | 0.27199782 |
| Hs.163725 | ESTs | −2.95828293 | −0.40992684 | 0.13856918 | 0.75659 | 0.27199782 |
| Hs.34579 | hypothetical protein FLJ10948 (FLJ10948) | −2.93640298 | −0.42082436 | 0.14331288 | 0.75689 | 0.27199782 |

Significant Upregulated Genes

| Gene Name | Gene ID | Score (d) | Numerator (r) | Denominator (s + s0) | Fold Change | q-value (%) |
|---|---|---|---|---|---|---|
| Hs.26670 | Human PAC clone RP3-515N1 from 22q11.2-q22 | −2.92169169 | −0.46501073 | 0.15915804 | 0.73897 | 0.27199782 |
| Hs.6606 | KIAA1109 protein (KIAA1109) | −2.90581746 | −0.34917157 | 0.12016294 | 0.77190 | 0.27199782 |
| Hs.334841 | selenium binding protein 1 (SELENBP1) | −2.90228183 | −0.53253707 | 0.1834891 | 0.73069 | 0.27199782 |
| Hs.211614 | chloride channel 6 (CLCN6) | −2.82648927 | −0.3820022 | 0.13515077 | 0.74010 | 0.27199782 |
| Hs.14125 | p53 regulated PA26 nuclear protein (PA26) | −2.70830756 | −0.52979454 | 0.19561831 | 0.81550 | 0.27199782 |
| Hs.170261 | ESTs | −2.59660094 | −0.72017351 | 0.2773524 | 0.79916 | 0.27199782 |
| Hs.24279 | KIAA0806 gene product (KIAA0806) | −2.58670405 | −0.23150022 | 0.08949621 | 0.84811 | 0.27199782 |
| Hs.83381 | guanine nucleotide binding protein 11 (GNG11) | −2.57444749 | −0.43095711 | 0.1673979 | 0.72764 | 0.27199782 |
| Hs.80545 | mitogen-activated protein kinase 8 interacting protein 2 (MAPK8IP2) | −2.56560737 | −0.52002034 | 0.20268898 | 0.67846 | 0.27199782 |
| Hs.352413 | chaperonin containing TCP1, subunit 8 (theta) (CCT8) | −2.52837862 | −0.31985871 | 0.12650744 | 0.81426 | 0.27199782 |
| Hs.24758 | ESTs | −2.40266066 | −0.42164464 | 0.17549071 | 0.79853 | 0.27199782 |
| Hs.27973 | KIAA0874 protein (KIAA0874) | −2.37907339 | −0.41377354 | 0.17392214 | 0.73544 | 0.27199782 |
| Hs.432790 | Homo sapiens cDNA: FLJ23582 fis, clone LNG13759 | −2.37574729 | −0.36811418 | 0.15494669 | 0.81504 | 0.27199782 |
| Hs.26418 | ESTs | −2.35530275 | −0.45930149 | 0.19500741 | 0.71293 | 0.50485927 |
| Hs.15220 | ESTs, Weakly similar to zinc finger protein 106 [*M. musculus*] (ZFP106) | −2.32669624 | −0.25972128 | 0.11162664 | 0.83809 | 0.50485927 |
| Hs.208414 | Homo sapiens mRNA; cDNA DKFZp564D0472 (from clone DKFZp564D0472) | −2.3201161 | −0.32416509 | 0.13971934 | 0.77172 | 0.50485927 |
| Hs.177635 | KIAA1095 protein (KIAA1095) | −2.27996304 | −0.47000067 | 0.20614399 | 0.69676 | 0.69252078 |
| Hs.20295 | ESTs | −2.26647751 | −0.2753334 | 0.12148075 | 0.81381 | 0.69252078 |
| Hs.143601 | Homo sapiens cDNA FLJ20678 fis, clone KAIA4163 | −2.2359993 | −0.28713412 | 0.12841423 | 0.79712 | 0.69252078 |
| Hs.153179 | ribosomal protein, large P2 (RPLP2) | −2.1697615 | −0.26644626 | 0.12279979 | 0.83829 | 1.28369705 |
| Hs.29191 | epithelial membrane protein 2 (EMP2) | −2.15845615 | −0.31964271 | 0.14808858 | 0.80186 | 1.28369705 |
| Hs.154797 | KIAA0090 protein (KIAA0090) | −2.14630109 | −0.24363817 | 0.11351538 | 0.83816 | 1.28369705 |
| Hs.127337 | axin 2 (conductin, axil) (AXIN2) | −2.01849379 | −0.22433745 | 0.11114102 | 0.85001 | 2.08629682 |
| Hs.432790 | Homo sapiens cDNA: FLJ23582 fis, clone LNG13759 | −2.01727159 | −0.25574906 | 0.12677968 | 0.84215 | 2.08629682 |
| Hs.26002 | LIM domain binding 1 (LDB1) | −2.00480389 | −0.17506154 | 0.08732103 | 0.88236 | 2.08629682 |
| Hs.27973 | Homo sapiens cDNA FLJ20053 fis, clone COL00809. | −1.98830118 | −0.43983115 | 0.22120952 | 0.72974 | 2.08629682 |
| Hs.155182 | KIAA1036 protein (KIAA1036) | −1.96266233 | −0.23934489 | 0.12194909 | 0.83497 | 2.08629682 |
| Hs.258730 | heme-regulated initiation factor 2-alpha kinase (HRI) | −1.94772066 | −0.30225721 | 0.15518509 | 0.83954 | 2.08629682 |
| Hs.25951 | Rho guanine nucleotide exchange factor (GEF) 3 (ARHGEF3) | −1.94714513 | −0.41123378 | 0.21119832 | 0.65987 | 2.08629682 |
| Hs.8136 | quiescent cell proline dipeptidase (DPP7) | −1.94611299 | −0.24023027 | 0.12344107 | 0.84708 | 2.08629682 |
| Hs.356344 | zinc finger protein 36 (KOX 18) (ZNF36) | −1.93518401 | −0.28154264 | 0.14548624 | 0.85414 | 2.08629682 |
| Hs.153639 | hypothetical SBBI03 protein (SBB103) | −1.91175493 | −0.24242803 | 0.12680916 | 0.86669 | 4.44342297 |
| Hs.170056 | Homo sapiens mRNA: cDNA DKFZp586B0220 (from clone DKFZp586B0220) | −1.89784876 | −0.55061501 | 0.29012586 | 0.22072 | 4.44342297 |
| Hs.82112 | interleukin 1 receptor, type I (IL1R1) | −1.8921268 | −0.33324684 | 0.17612289 | 0.77867 | 4.44342297 |
| Hs.47913 | coagulation factor X (F10) | −1.88931086 | −0.24229629 | 0.12824586 | 0.81539 | 4.44342297 |
| Hs.58414 | filamin C, gamma (actin-binding protein-280) (FLNC) | −1.88226223 | −0.259789 | 0.13801955 | 0.78645 | 4.44342297 |
| Hs.163725 | ESTs | −1.8739173 | −0.42067057 | 0.22448726 | 0.28114 | 4.44342297 |
| Hs.350388 | ESTs | −1.85084709 | −0.46576042 | 0.25164716 | 0.27509 | 4.44342297 |
| Hs.77385 | Homo sapiens myosin, light polypeptide 6, alkali, smooth muscle and non-muscle (MYL6), mRNA. (MYL6) | −1.85028666 | −0.23423984 | 0.12659651 | 0.84663 | 4.44342297 |
| Hs.11039 | Homo sapiens cDNA FLJ12798 fis, clone NT2RP2002076, highly similar to Homo sapiens clone 24804 mRNA sequence (MGC2722) | −1.84990185 | −0.22268855 | 0.12037857 | 0.85691 | 4.44342297 |
| Hs.75335 | glycine amidinotransferase (L-arginine: glycine amidinotransferase) (GATM) | −1.84126621 | −0.35233323 | 0.19135377 | 0.74000 | 4.44342297 |
| Hs.373498 | organic cation transporter (LOC57100) | −1.79208398 | −0.44085062 | 0.24599886 | 0.82117 | 4.44342297 |
| Hs.179735 | Homo sapiens mRNA: cDNA DKFZp434P1514 (from clone DKFZp434P1514); partial cds (DKFZp434P1514) | −1.78655725 | −0.57761661 | 0.32331268 | 0.77298 | 4.44342297 |
| Hs.3407 | protein kinase (cAMP-dependent, catalytic) inhibitor gamma (PKIG) | −1.77424818 | −0.16272077 | 0.09171252 | 0.89140 | 4.44342297 |
| Hs.62192 | coagulation factor III (thromboplastin, tissue factor) (F3) | −1.76731078 | −0.54771014 | 0.30991162 | 0.52041 | 4.44342297 |
| Hs.17270 | DKFZP434C211 protein (DKFZP434C211) | −1.76107883 | −0.20459113 | 0.11617375 | 0.84740 | 4.44342297 |
| Hs.118630 | MAX-interacting protein 1 (MXI1) | −1.74086039 | −0.25335606 | 0.14553497 | 0.84390 | 4.44342297 |
| Hs.323583 | AD021 protein (LOC51313) | −1.72245235 | −0.43895237 | 0.25484151 | 0.28919 | 4.44342297 |
| Hs.8026 | Homo sapiens cDNA: FLJ21987 fis, clone HEP06306 | −1.69390783 | −0.22935042 | 0.13539723 | 0.84512 | 4.44342297 |
| Hs.34359 | ESTs | −1.65617257 | −0.22756407 | 0.1374036 | 0.87929 | 4.44342297 |
| Hs.25253 | Homo sapiens cDNA: FLJ20935 fis, clone ADSE01534 (MAN1A1) | −1.65599971 | −0.34298933 | 0.2071192 | 0.75112 | 4.44342297 |
| Hs.111903 | Fc fragment of IgG, receptor, transporter, alpha (FCGRT) | −1.62435104 | −0.24121667 | 0.14850033 | 0.83548 | 4.44342297 |
| Hs.179735 | ras homolog gene family, member C (ARHC) | −1.604214041 | −0.22927649 | 0.14292138 | 0.87841 | 4.44342297 |
| Hs.79914 | lumican (LUM) | −1.60012485 | −0.35795777 | 0.22370615 | 0.75593 | 4.44342297 |
| Hs.366 | interferon induced transmembrane protein 1 (9-27) (IFITM1) | −1.59367416 | −0.38664867 | 0.24261463 | 0.85753 | 4.44342297 |
| Hs.124696 | Homo sapiens oxidoreductase UCPA (LOC56898), mRNA. (LOC56898) | −1.58443416 | −0.18040354 | 0.11385992 | 0.87759 | 4.44342297 |
| Hs.127337 | ESTs (AXIN2) | −1.58351156 | −0.41159548 | 0.25992578 | 0.67751 | 4.44342297 |

Tumor classification and patient stratification. The invention provides for methods of classifying tumors, and thus grouping or "stratifying" patients, according to the CSR signature. As shown in the Examples, tumors classified as having an "induced" signature carry a higher risk of metastasis and death, and therefore may be treated more aggressively than tumors of a "quiescent" type.

The tumor of each patient in a pool of potential patients for a clinical trial can be classified as described above. Patients having similarly classified tumors can then be selected for participation in an investigative or clinical trial of a cancer therapeutic where a homogeneous population is desired. The tumor classification of a patient can also be used in assessing the efficacy of a cancer therapeutic in a heterogeneous patient population. Thus, comparison of an individual's expression profile to the population profile for a type of cancer, permits the selection or design of drugs or other therapeutic regimens that are expected to be safe and efficacious for a particular patient or patient population (i.e., a group of patients having the same type of cancer).

The methods of the invention can be carried out using any suitable probe for detection of a gene product that is differentially expressed in colon cancer cells. For example, mRNA (or cDNA generated from mRNA) expressed from a CSR gene can be detected using polynucleotide probes. In another example, the CSR gene product is a polypeptide, which polypeptides can be detected using, for example, antibodies that specifically bind such polypeptides or an antigenic portion thereof.

The present invention relates to methods and compositions useful in diagnosis of cancer, design of rational therapy, and the selection of patient populations for the purposes of clinical trials. The invention is based on the discovery that tumors of a patient can be classified according to CSR expression profile. Polynucleotides that correspond to the selected CSR genes can be used in diagnostic assays to provide for diagnosis of cancer at the molecular level, and to provide for the basis for rational therapy (e.g., therapy is selected according to the expression pattern of a selected set of genes in the tumor). The gene products encoded by CSR genes can also serve as therapeutic targets, and candidate agents effective against such targets screened by, for example, analyzing the ability of candidate agents to modulate activity of differentially expressed gene products.

The term expression profile is used broadly to include a genomic expression profile, e.g., an expression profile of mRNAs, or a proteomic expression profile, e.g., an expression profile of one or more different proteins. Profiles may be generated by any convenient means for determining differential gene expression between two samples, e.g. quantitative hybridization of mRNA, labeled mRNA, amplified mRNA, cRNA, etc., quantitative PCR, ELISA for protein quantitation, and the like. A subject or patient tumor sample, e.g., cells or collections thereof, e.g., tissues, is assayed. Samples are collected by any convenient method, as known in the art. Additionally, tumor cells may be collected and tested to determine the relative effectiveness of a therapy in causing differential death between normal and diseased cells. Genes/proteins of interest are genes/proteins that are found to be predictive, including the genes/proteins provided above, where the expression profile may include expression data for 5, 10, 20, 25, 50, 100 or more of, including all of the listed genes/proteins.

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic methods is one that is a nucleic acid sample. The nucleic acid sample includes a plurality or population of distinct nucleic acids that includes the expression information of the phenotype determinative genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained.

The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample is typically prepared from a tumor cell or tissue harvested from a subject to be diagnosed, using standard protocols, where cell types or tissues from which such nucleic acids may be generated include any tissue in which the expression pattern of the to be determined phenotype exists. Cells may be cultured prior to analysis.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acid provides information regarding expression for each of the genes that have been probed, where the expression information is in terms of whether or not the gene is expressed and, typically, at what level, where the expression data, i.e., expression profile, may be both qualitative and quantitative.

Alternatively, non-array based methods for quantitating the levels of one or more nucleic acids in a sample may be employed, including quantitative PCR, and the like.

Where the expression profile is a protein expression profile, any convenient protein quantitation protocol may be employed, where the levels of one or more proteins in the assayed sample are determined. Representative methods include, but are not limited to; proteomic arrays, flow cytometry, standard immunoassays, etc.

Following obtainment of the expression profile from the sample being assayed, the expression profile is compared with a reference or control profile to make a diagnosis. A reference or control profile is provided, or may be obtained by empirical methods from samples of fibroblasts exposed to serum. In certain embodiments, the obtained expression profile is compared to a single reference/control profile to obtain information regarding the phenotype of the cell/tissue being assayed. In yet other embodiments, the obtained expression profile is compared to two or more different reference/control profiles to obtain more in depth information regarding the phenotype of the assayed cell/tissue. For example, the obtained expression profile may be compared to a positive and negative reference profile to obtain confirmed information regarding whether the cell/tissue has the phenotype of interest.

The difference values, i.e. the difference in expression may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

A statistical analysis step is then performed to obtain the weighted contribution of the set of predictive genes. For example, nearest shrunken centroids analysis may be applied as described in Tibshirani et al. (2002) P.N.A.S. 99:6567-6572 to compute the centroid for each class, then compute the average squared distance between a given expression profile and each centroid, normalized by the within-class standard deviation.

The classification is probabilistically defined, where the cut-off may be empirically derived. In one embodiment of the invention, a probability of about 0.4 may be used to distinguish between quiescent and induced patients, more usually a probability of about 0.5, and may utilize a probability of about 0.6 or higher. A "high" probability may be at least about 0.75, at least about 0.7, at least about 0.6, or at least about 0.5. A "low" probability may be not more than about 0.25, not more than 0.3, or not more than 0.4. In many embodiments, the above-obtained information about the cell/tissue being assayed is employed to predict whether a host, subject or patient should be treated with a therapy of interest and to optimize the dose therein.

Databases of Expression Profiles

Also provided are databases of expression profiles of CSR genes. Such databases will typically comprise expression profiles derived from serum induced fibroblasts, typical cancer cell samples, etc. The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression profile.

Reagents and Kits

Also provided are reagents and kits thereof for practicing one or more of the above-described methods. The subject reagents and kits thereof may vary greatly. Reagents of interest include reagents specifically designed for use in production of the above described expression profiles of phenotype determinative genes.

One type of such reagent is an array of probe nucleic acids in which CSR genes of interest are represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In certain embodiments, the number of genes that are from that is represented on the array is at least 10, usually at least 25, and may be at least 50, 100, up to including all of the CSR genes, preferably utilizing the top ranked set of genes. Where the subject arrays include probes for such additional genes, in certain embodiments the number % of additional genes that are represented does not exceed about 50%, usually does not exceed about 25%.

Another type of reagent that is specifically tailored for generating expression profiles of CSR genes is a collection of gene specific primers that is designed to selectively amplify such genes, for use in quantitative PCR and other quantitation methods. Gene specific primers and methods for using the same are described in U.S. Pat. No. 5,994,076, the disclosure of which is herein incorporated by reference. Of particular interest are collections of gene specific primers that have primers for at least 10 of the CSR genes, often a plurality of these genes, e.g., at least 25, and may be 50, 100 or more to include all of the CSR genes. The subject gene specific primer collections may include only CSR genes, or they may include primers for additional genes.

The kits of the subject invention may include the above described arrays and/or gene specific primer collections. The kits may further include a software package for statistical analysis of one or more phenotypes, and may include a reference database for calculating the probability of susceptibility. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

Diagnosis, Prognosis, Assessment of Therapy (Therametrics), and Management of Cancer The classification methods described herein, as well as their gene products and corresponding genes and gene products, are of particular interest as genetic or biochemical markers (e.g., in blood or tissues) that will detect the earliest changes along the carcinogenesis pathway and/or to monitor the efficacy of various therapies and preventive interventions.

Staging. Staging is a process used by physicians to describe how advanced the cancerous state is in a patient. Staging assists the physician in determining a prognosis, planning treatment and evaluating the results of such treatment. Staging systems vary with the types of cancer, but generally involve the following "TNM" system: the type of tumor, indicated by T; whether the cancer has metastasized to nearby lymph nodes, indicated by N; and whether the cancer has metastasized to more distant parts of the body, indicated by M. Generally, if a cancer is only detectable in the area of the primary lesion without having spread to any lymph nodes it is called Stage I. If it has spread only to the closest lymph nodes, it is called Stage II. In Stage III, the cancer has generally spread to the lymph nodes in near proximity to the site of the primary lesion. Cancers that have spread to a distant part of the body, such as the liver, bone, brain or other site, are Stage IV, the most advanced stage.

The methods described herein can facilitate fine-tuning of the staging process by identifying the aggressiveness of a cancer, e.g. the metastatic potential, as well as the presence in different areas of the body. Thus, a Stage II cancer with a classification signifying a high metastatic potential cancer can be used to change a borderline Stage II tumor to a Stage III tumor, justifying more aggressive therapy. Conversely, the presence of a polynucleotide signifying a lower metastatic potential allows more conservative staging of a tumor.

The following examples are offered by way of illustration and not by way of limitation.

Example 1

Identification of a Stereotyped Genomic Response of Fibroblasts to Serum. We previously observed that the global transcriptional response of fibroblasts to serum integrates many processes involved in wound healing. Because fibroblasts from different anatomic sites are distinct differentiated cells with characteristic gene expression profiles, we investigated whether the genomic responses to serum varied significantly among fibroblasts cultured from different anatomic sites. Fifty fibroblast cultures derived from ten anatomic sites were cultured asynchronously in 10% fetal bovine serum (FBS) or in media containing only 0.1% FBS. Analysis of the global gene expression patterns, using human cDNA microarrays containing approximately 36,000 genes, revealed that although fibroblasts from different sites have distinctly different gene expression programs, they share a stereotyped gene expression program in response to serum (FIG. 1A). Selection for genes that were concordantly induced or repressed by most types of fibroblasts yielded 677 genes, represented by 772 cDNA probes, of which 611 are uniquely identified by UniGene.

This common genomic response to serum includes induction of genes that represent entry into and progression through the cell cycle (e.g., E2F1, FOXM1, PTTG1), induction of cell motility (e.g., CORO1C, FLNC), extracellular matrix remodeling (LOXL2, PLOD2, PLAUR), cell-cell signaling (SDFR1, ESDN, MIF), and acquisition of a myofibroblast phenotype (e.g., TAGLN, TPM2, MYL6). Analysis of the public Gene Ontology (GO) annotation of the fibroblast serum response genes confirmed a significant enrichment of genes involved in cell proliferation, blood coagulation, complement activation, secretory protein synthesis, angiogenesis, and proteolysis, reflecting the diverse roles that fibroblasts may play during wound healing.

One of the most consistent and important responses of human cells to serum is proliferation. Abnormal cell proliferation is also a consistent characteristic of cancer cells, irrespective of any possible involvement of a wound-healing response. We therefore sought to eliminate the contributions of genes directly related to cell proliferation, to improve the specificity of a genomic signature of the fibroblast serum response. To identify features directly related to cell cycle progression, we examined the expression pattern of these 677 genes during the cell cycle (in HeLa cells). Despite the well-known role of serum as a mitogen, only one-quarter (165 out of 677 genes) of the fibroblast serum response genes showed periodic expression during the cell cycle (FIG. 1B). The majority of the genes whose expression levels in fibroblasts showed the most consistent response to serum exposure do not appear simply to reflect cell growth or division; these 512 serum-responsive and cell cycle-independent genes are operationally defined as the fibroblast core serum response (CSR). Comparison of the common fibroblast serum response with a detailed analysis of the temporal program of gene expression following serum exposure in foreskin fibroblasts confirmed that the cell cycle genes and the CSR have distinct temporal profiles during serum stimulation and are thus distinguishable biological processes (FIG. 1C).

Expression of Fibroblast CSR in Human Cancers. Because serum (as distinct from plasma and normal extracellular fluid) is encountered in vivo only at sites of tissue injury or remodeling and induces in fibroblasts a gene expression response suggestive of wound healing, we reasoned that expression of fibroblast CSR genes in tumors would gauge the extent to which the tumor microenvironment recapitulates normal wound healing. We examined the expression of genes comprising the fibroblast CSR in publicly available microarray data from a variety of human cancers and their corresponding normal tissues. To facilitate visualization and analysis, we organized the gene expression patterns and samples by hierarchical clustering. Remarkably, we observed a predominantly biphasic pattern of expression for the fibroblast CSR in diverse cancers, including breast cancers, lung cancers, gastric cancers, prostate cancers, and hepatocellular carcinoma. Expression levels of genes that were activated by serum in fibroblasts varied coordinately in tumors, and genes that were repressed by serum in fibroblasts were mostly expressed in a reciprocal pattern (FIG. 2).

Figure 2:
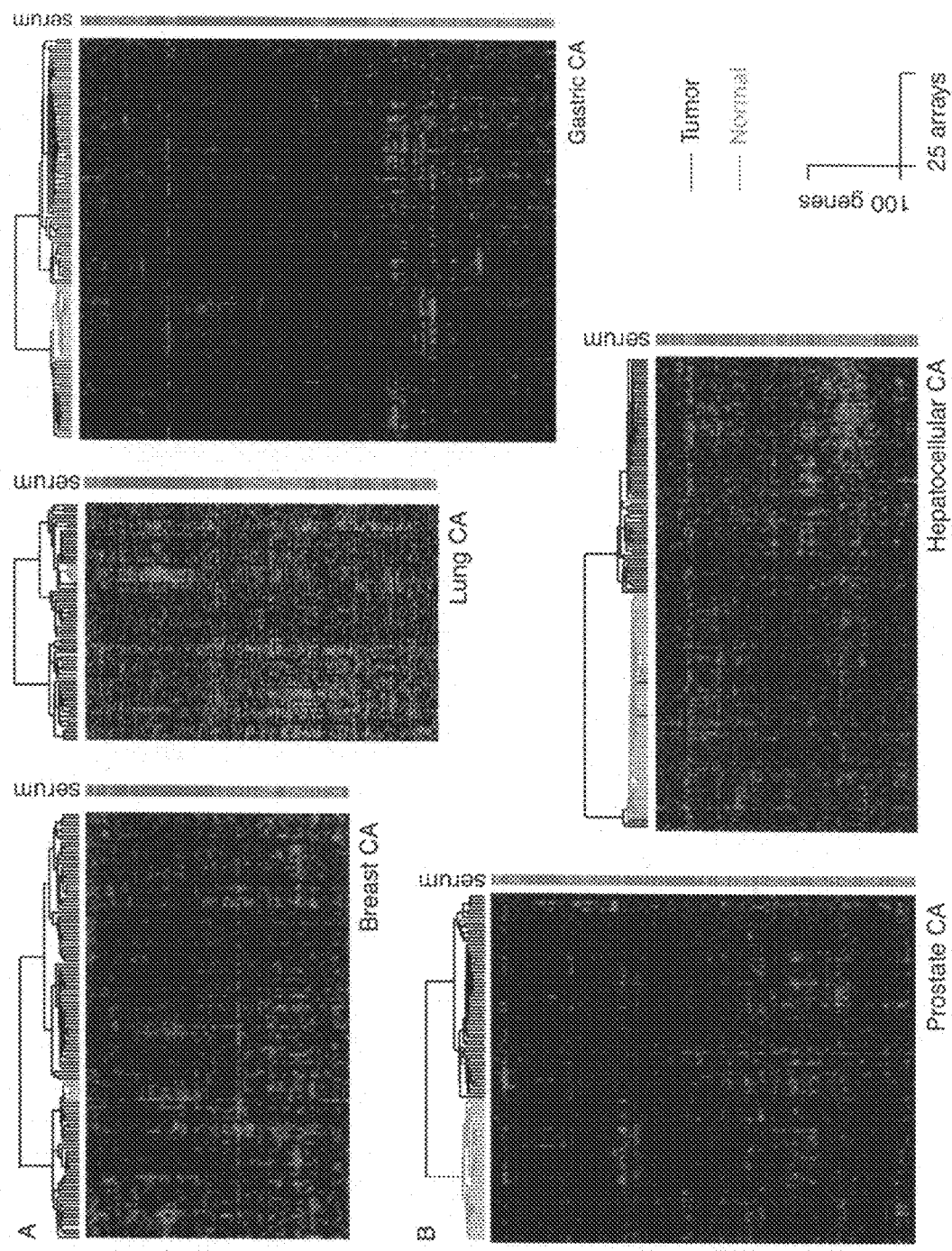
FIG. 2. Survey of Fibroblast CSR Gene Expression in Human Cancers. Expression patterns of available CSR genes in over 500 tumors and corresponding normal tissues were extracted, filtered as described in Materials and Methods, and organized by hierarchical clustering. The response of each gene in the fibroblast serum response is shown on the right bar (red shows activated; green shows repressed by serum). The strong clustering of the genes induced or repressed, respectively, in fibroblasts in response to serum exposure, based solely on their expression patterns in the tumor samples, highlights their coordinate regulation in tumors. The dendrograms at the top of each data display represent the similarities among the samples in their expression of the fibroblast CSR genes; tumors are indicated by black branches, normal tissue by green branches.

In each of the tumor types examined, the expression pattern of the fibroblast CSR genes in normal tissues closely approximated that seen in quiescent fibroblasts cultured in the absence of serum (FIG. 2). In prostate and hepatocellular carcinomas, all of the normal tissue samples had the serum-repressed signature and almost all of the tumors had the serum-induced signature, albeit with varying amplitude. In breast, lung, and gastric carcinomas, the common fibroblast serum response signature was clearly evident in some of the tumors and apparently absent in others, suggesting that a "wound-healing phenotype" was a variable feature of these cancers. We therefore classified breast, lung, and gastric cancer samples based on the pattern of expression of the genes that comprise the fibroblast CSR.

Figure 3:
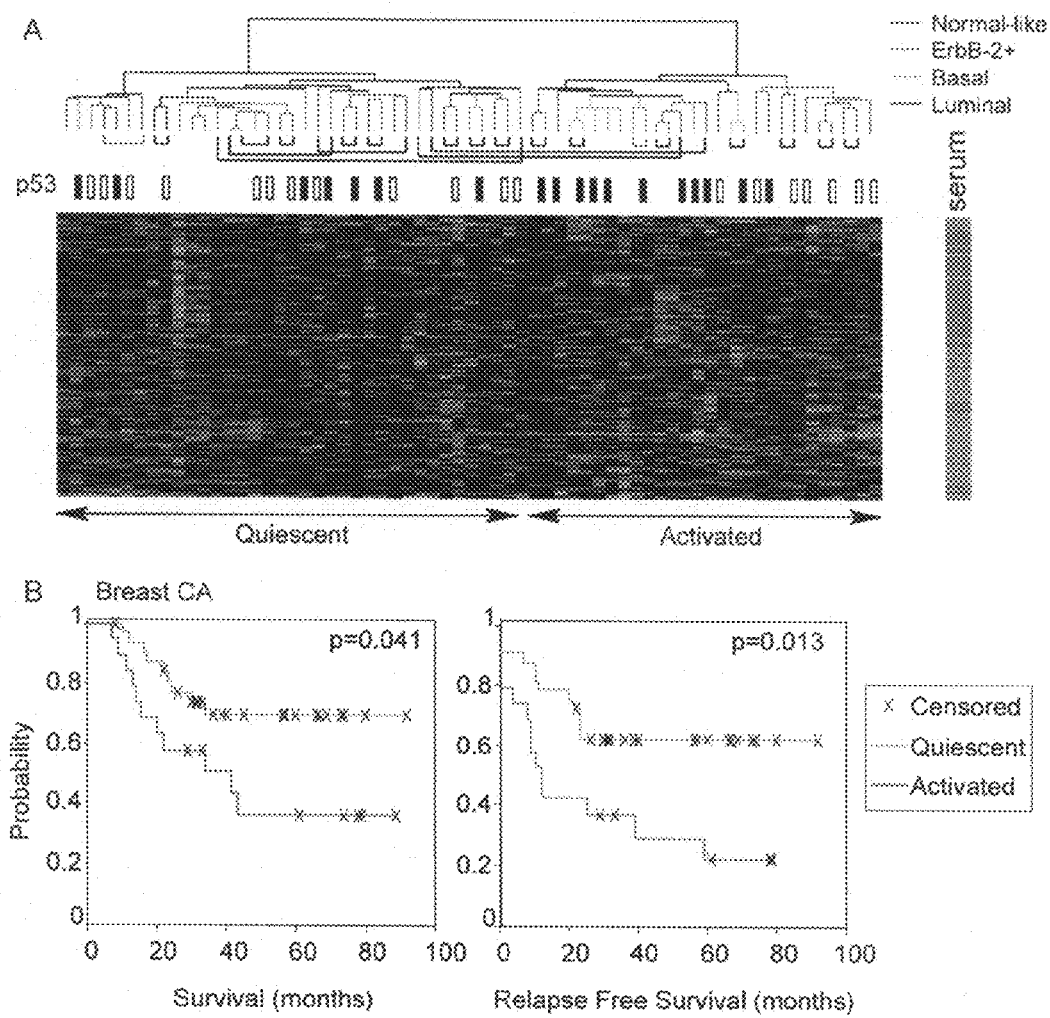
FIGS. 3A-3B. Context, Stability, and Prognostic Value of Fibroblast CSR in Breast Cancer.

Link between the Gene Expression Signature of Fibroblast Serum Response and Cancer Progression. To investigate the stability and consistency of the serum response signature in individual tumors and to explore its clinical implications, we examined CSR gene expression in a group of locally advanced breast cancers with extensive clinical and molecular data. As shown in FIG. 3A, the expression profiles of the CSR genes were biphasic, allowing a natural separation of these tumors into two classes. Interestingly, in 18 out of 20 paired tumor samples obtained from the same patients before and after excisional biopsy and chemotherapy, the CSR expression phenotypes were consistent between the two samples. Thus, the wound-related expression program appears to be an intrinsic property of each tumor and not easily extinguished. In a set of 51 patients with clinically matched disease and equivalent treatment, primary tumors with the activated CSR signature were significantly more likely to progress to metastasis and death in a 5-y follow-up period (p=0.013 and 0.041, respectively) (FIG. 3B). Using an alternative analytic approach, classifying each sample by the Pearson correlation between tumor and fibroblast expression patterns of the fibroblast CSR genes, also reproduced the identification of two classes of samples with differing clinical outcomes. A gene expression pattern similar to the serum-activated program of fibroblasts is thus a powerful predictor of prognosis.

Other significant prognostic factors in these same patients include tumor grade, estrogen receptor status, and tumor subtype based on gene expression profile. Tumor stage, lymph-node status, and p53 status were not statistically significant predictors of survival in these patients (p=0.13, 0.79, 0.05, respectively). A "basal-like" subtype of breast cancer, characterized by molecular similarities of the tumor cells to basal epithelial cells of the normal mammary duct and associated with a particularly unfavorable prognosis, was significantly associated with a gene expression pattern resembling the fibroblast CSR: six of seven basal-like breast cancers had the "serum-activated" gene expression signature (p=0.0075, Fisher's exact test). Thus, the presence or absence of the wound-like phenotype is linked to intrinsic features of the tumor cells.

We considered the possibility that the observed phenomenon may be simply a reflection of the number of fibroblasts in tumor samples. Perhaps tumors that are infiltrative or otherwise worrisome clinically would demand a wide margin of excision that would include more fibroblasts in the resultant samples. However, classification of breast cancers using the top 1% most highly expressed fibroblast genes (which include a number of extracellular matrix genes and have been previous observed as the "stroma signature") showed no relationship between the generic fibroblast signature and clinical outcome (p=0.75). Thus, the prognostic value of the fibroblast CSR reflects the physiologic state of the tumor microenvironment and not just the number of fibroblasts in tumor stroma. Similarly, although the mitotic index is an established criterion of tumor grade, classification of these tumors based on expression of cell cycle genes only had moderate prognostic value (p=0.08). This result also demonstrates that the prognostic value of the fibroblast CSR is unlikely to be accounted for by the incomplete annotation and removal of genes representing cell growth or division.

Figure 4:
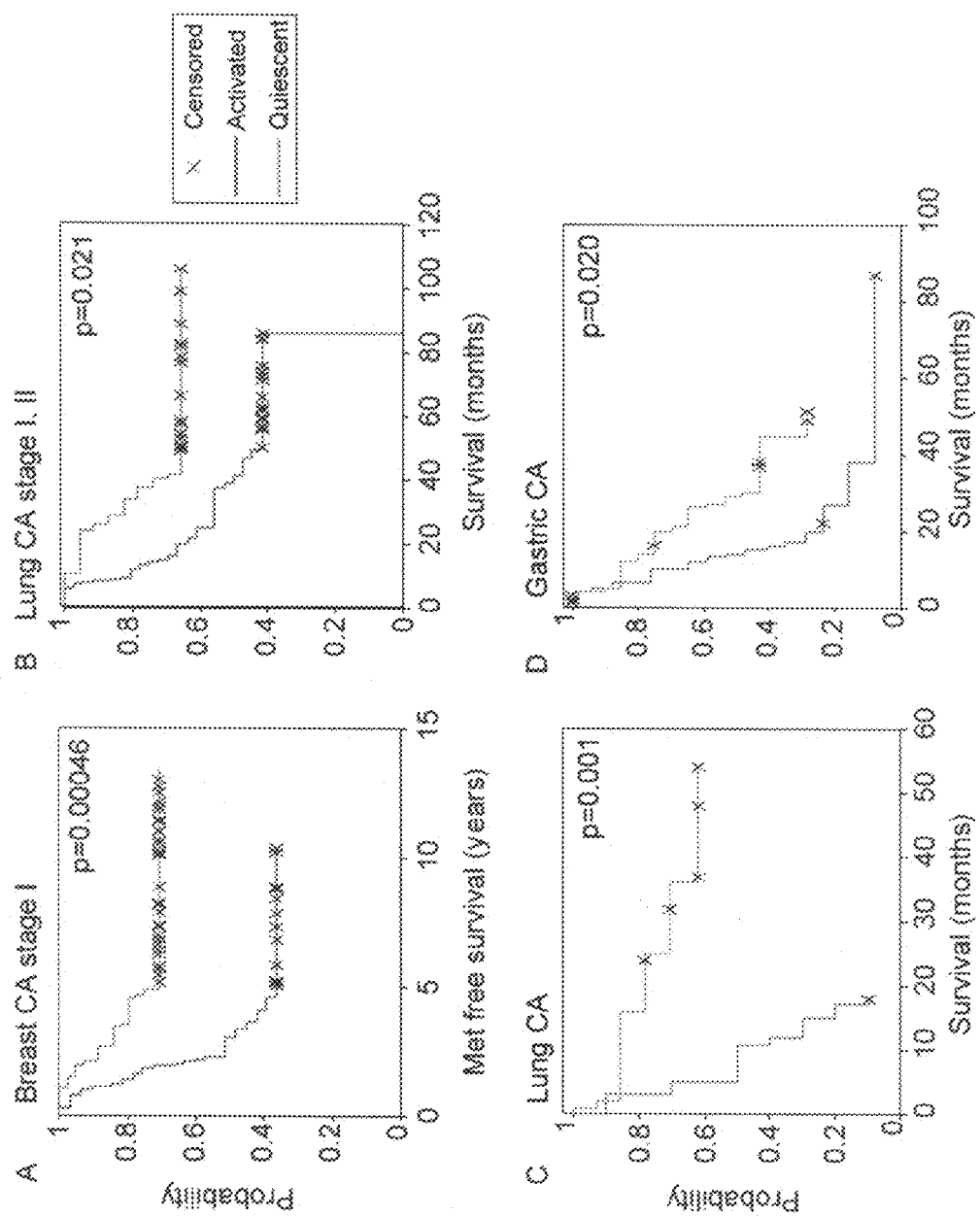
FIGS. 4A-4D. Prognostic Value of Fibroblast CSR in Epithelial Tumors. Kaplan-Meier survival curves of tumors stratified into two classes using the fibroblast CSR are shown for stage I and IIA breast cancer, FIG. 4A; stage I and II lung adenocarcinoma, FIG. 4B; lung adenocarcinoma of all stages, FIG. 4C, and stage III gastric carcinoma, FIG. 4D.

To extend and validate these results, we tested the prognostic power of the fibroblast CSR signature in independent datasets and different kinds of human cancer (FIG. 4). Using published DNA microarray data from a study of gene expression patterns in a group of 78 early (tumor smaller than 5 cm, stage I and IIA) breast cancer patients, we could segregate the patients into two groups based on expression of the fibroblast CSR genes in the biopsy samples. Tumors with the serum-induced signature had a significantly increased risk of metastasis over 5 y (p=0.00046) (FIG. 4A). Multivariate Cox proportional hazard analysis confirmed that the CSR classification is a significant independent predictor (p=0.009); the serum-induced gene expression signature was associated with a 3.3-fold relative risk of breast cancer metastasis within 5 y of diagnosis. In the two breast cancer datasets examined, approximately 50% of the CSR genes demonstrated significant differences in expression between the activated and quiescent groups of samples, but permutation and 10-fold balanced leave-one-out analyses revealed that the correct classification can be accomplished using as few as 6% of CSR genes.

Thus, the expression pattern of the CSR genes provides a robust basis for predicting tumor behavior. Similarly, in analysis of published DNA microarray data from 62 patients with stage I and II lung adenocarcinomas, tumors with the serum-induced signature were associated with significantly higher risk of death compared to tumors with the serum-repressed signature (p=0.021) (FIG. 4B). These results suggest that presence or absence of a wound-like phenotype in these cancers, with its prognostic implication for their metastatic potential, may be determined at an early stage in their development. In a second, independent group of lung adenocarcinomas of all stages, tumors with the fibroblast serum-induced signature were associated with a significantly worse prognosis (p=0.0014) (FIG. 4C). A significant correlation between advanced stage and the serum-induced signature was also apparent in this dataset. Finally, in 42 patients with stage III gastric carcinomas, all treated with gastrectomy alone, tumors with the activated CSR signature were again associated with shorter survival (p=0.02) (FIG. 4D). These results demonstrate that a wound-healing phenotype, reflected in the expression of a set of serum-inducible genes in fibroblasts, is strongly linked to progression of diverse human carcinomas and can provide valuable prognostic information even at an early stage in the natural history of a cancer.

Histological Architecture of CSR Gene Expression in Tumors. Both to validate the DNA microarray results and to investigate the histological architecture of CSR gene expression in tumors, we examined the expression patterns of five CSR genes implicated in extracellular matrix remodeling and cell-cell interaction, using tissue microarrays containing hundreds of breast carcinoma tissues. PLAUR, also known as urokinase-type plasminogen activator receptor, is a well-characterized receptor for matrix-degrading proteases that has been implicated in tumor cell invasion. LOXL2 is a member of a family of extracellular lysyl oxidases that modify and cross-link collagen and elastin fibers. PLOD2 is a member of the lysyl hydroxylase family that plays important roles in matrix cross-linking and fibrosis. SDFR1, previously named gp55 and gp65, encodes a cell surface protein of the immunglobulin superfamily that regulates cell adhesion and process outgrowth. ESDN is a neuropilin-like cell surface receptor that was also previously found to be upregulated in metastatic lung cancers. All five of these genes were included in the fibroblast CSR gene set by virtue of their induction by serum in fibroblasts (see FIG. 1).

Figure 5:
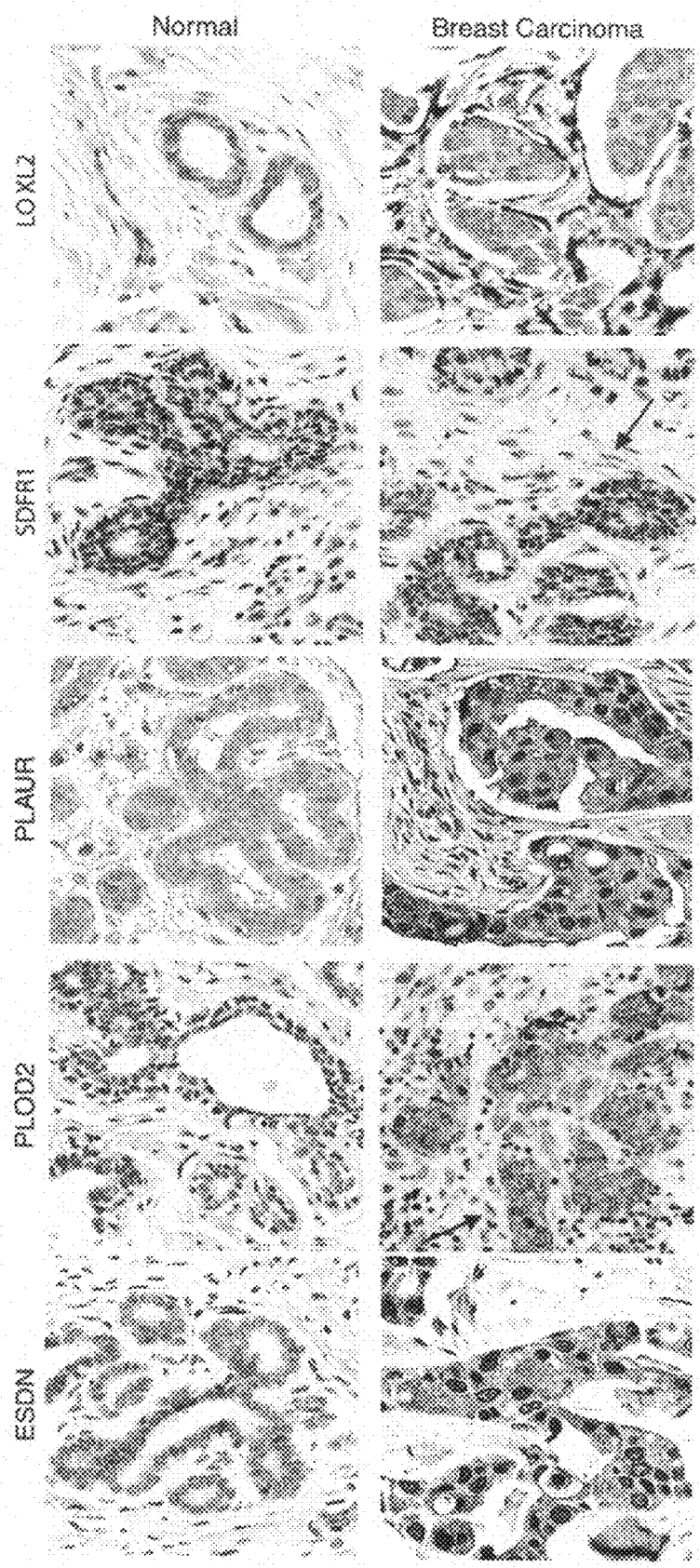
FIG. 5. Histological Architecture of CSR Gene Expression in Breast Cancer. Representative ISH of LOXL2 and SDFR1 and IHC of PLOD2, PLAUR, and ESDN are shown (magnification, 200×). Panels for LOXL2, PLAUR, PLOD2, and ESDN represent cores of normal and invasive ductal breast carcinoma from different patients on the same tissue microarray. Panels for SDFR1 demonstrate staining in adjacent normal and carcinoma cells on the same tissue section. Arrows highlight spindle-shaped stromal cells that stain positive for SDFR1 and PLOD2. No signal was detected for the sense probe for ISH or for control IHC without the primary antibody.

Anti-PLAUR antibody is commercially available and served as a positive control. We prepared specific riboprobes for LOXL2 and SDFR1 and generated affinity-purified anti-peptide antibodies to PLOD2 and ESDN to detect the predicted protein products. As shown in FIG. 5, PLAUR, LOXL2, PLOD2, and ESDN were not detectably expressed in normal breast tissue; SDFR1 was expressed at a low level in normal breast epithelial cells (n=11). In contrast, all five genes were induced in a significant fraction of invasive ductal carcinomas of the breast. As previously reported, PLAUR protein is expressed in both tumor cells and peritumoral stroma (70 out of 96, 73% positive) (FIG. 5). PLOD2 protein and SDFR1 mRNA were detected in breast carcinoma cells and in a small but consistent fraction of peritumor stroma cells (78 out of 100, 78% positive, and 55 out of 79, 70% positive, respectively). ESDN protein was detected exclusively in breast carcinoma cells (69 out of 112, 62% positive). In contrast, LOXL2 mRNA was abundant in peritumoral fibroblasts around invasive carcinomas (45 out of 106, 42% positive). LOXL2 protein has been previously reported to be expressed in normal mammary ducts and increased in invasive breast carcinoma cells. Our data suggest that LOXL2 is primarily synthesized by peritumoral fibroblasts, but may act on or in the vicinity of epithelial cells during tissue remodeling. Collectively, these results suggest that the pathophysiology represented by expression of the fibroblast CSR genes in cancers represents a multicellular program in which the tumor cells themselves, tumor-associated fibroblasts, and perhaps diverse other cells in the tumor microenvironment are active participants.

The remarkable ability of a single physiological fluid—serum—to promote the growth and survival of diverse normal and cancer cells in culture suggests that there may be a conserved, programmed response to the molecular signals that serum provides. In vivo, serum as a physiological signal has a very specific meaning: cells encounter serum—the soluble fraction of coagulated blood—only in the context of a local injury. In virtually any tissue, a rapid, concerted multicellular response, with distinct physiological exigencies that evolve over minutes, hours, and days, is required to preserve the integrity of the tissue and often the survival of the organism. In response to a wound, many of the normal differentiated characteristics of the cells in the wounded tissue are temporarily set aside in favor of an emergency response. In wound repair, as in cancer, cells that ordinarily divide infrequently are induced to proliferate rapidly, extracellular matrix and connective tissues are invaded and remodeled, epithelial cells and stromal cells migrate, and new blood vessels are recruited. In all these respects, a wound response—and the characteristic physiological response to serum—appears to provide a highly favorable milieu for cancer progression.

We defined a stereotyped genomic expression response of fibroblasts to serum, which reflects many features of the physiology of wound healing. When we examined the expression of these genes in human tumors, we found strong evidence that a wound-like phenotype was variably present in many common human cancers (including many that are not known to be preceded by chronic wounds) and was a remarkably powerful predictor of metastasis and death in several different carcinomas.

At least three genes induced in the fibroblast serum response, PLAUR, LOXL2, and MIF, have been previously shown to increase cancer invasiveness or angiogenesis in animal xenograft models; each of these three genes has also been shown to play an important role in wound healing. Thus, coordinate induction of a wound-healing program in carcinomas may contribute to tumor invasion and metastasis.

Several potential mechanisms might contribute to the wound-like gene expression pattern in cancers. In some cancers, ongoing local tissue injury, resulting from growth and dysfunctional behavior of the tumor cells, could continuously trigger a normal wound-healing response. The classic observation of deposited fibrin products in human tumors is consistent with this model. Inflammatory cells, presumably recruited by tissue disorder, may amplify the wound response and contribute to tumor invasion in part by expression of metalloproteinases. The wound response might also be initiated directly by signals from the tumor cells, whose ability to activate an inappropriate wound-healing response—favorable to cell proliferation, invasion, and angiogenesis—might be strongly selected during cancer progression. The possibility that stromal cells might play a primary role in promoting a wound-like phenotype in some cancers is raised by studies showing that tumor-associated fibroblasts can enhance tumor engraftment and metastasis in animal models and the demonstration in some cancers of genotypic abnormalities in tumor-associated fibroblasts.

Our results illustrate the power of using gene expression data from specific cells or physiological and genetic manipulations to build an interpretive framework for the complex gene expression profiles of clinical samples. Several prognostic models based on gene expression patterns have previously been identified from systematic DNA microarray profiles of gene expression in human cancers. Some of these prognostic gene expression profiles appear to reflect the developmental lineage of the cancer cells, some appear to reflect the activity of specific molecular determinants of tumor behavior (e.g., the activity of PLA2G2A in gastric cancer), while still others represent the mechanistically agnostic results of machine-assisted learning. Although they serve to identify many of the same tumors with unfavorable prognosis, the genes that define the fibroblast CSR overlap minimally with the genes previously used to predict outcome in the same cancers. For example, the fibroblast CSR involves only 20 out of 456 genes in an "intrinsic gene list" that can serve to segregate breast cancers into prognostically distinct groups and four out of 128 genes that define the general metastasis signature reported by Ramaswamy et al. (2003). Only 11 genes are in common between the 231 gene van't Veer poor prognosis signature for breast cancer and the fibroblast CSR genes. The prognostic power of these different sets of genes illustrates the multidimensional variation in the gene expression programs in cancers and the complex interplay of many distinct genetic and physiological factors in determining the distinctive biology of each individual tumor. Our success in discovering a significant new determinant of cancer progression illustrates the richness of the data as a continuing source for future discoveries and the importance of unrestricted access to published research data.

Materials and Methods

Cells and tissue culture. Human primary fibroblasts from ten anatomic sites were cultured in 0.1% versus 10% FBS, as previously described (Chang et al. 2002 Proc Natl Acad Sci 99:12877-12882). For the serum induction timecourse, foreskin fibroblasts CRL 2091 (American Type Culture Collection [ATCC], Manassas, Va., United States) were serum-starved for 48 h and harvested at the indicated timepoints after switching to media with 10% FBS, essentially as described in Iyer et al. (1999) Science 283: 83-87.

Microarray procedures. Construction of human cDNA microarrays containing approximately 43,000 elements, representing approximately 36,000 different genes, and array hybridizations were as previously described (Perou et al. 2000 Nature 406: 747-752). mRNA was purified using Fast-Track according to the manufacturer's instructions (Invitrogen, Carlsbad, Calif., United States). For the serum time course, RNA from all of the sampled timepoints were pooled as reference RNA to compare with RNA from individual timepoints as described in Iyer et al. (1999) supra.

Data analysis. For defining a common serum response program in fibroblasts, global gene expression patterns in 50 fibroblast cultures derived from ten anatomic sites, cultured in the presence of 10% or 0.1% FBS, were characterized by DNA microarray hybridization (Chang et al. 2002, supra). We selected for further analysis genes for which the corresponding array elements had fluorescent hybridization signals at least 1.5-fold greater than the local background fluorescence in the reference channel, and we further restricted our analyses to genes for which technically adequate data were obtained in at least 80% of experiments. These filtered genes were then analyzed by the multiclass Significance Analysis of Microarrays (SAM) algorithm (Tusher et al. 2001 Proc Natl Acad Sci USA 98: 5116-5121) to select a set of genes whose expression levels had a significant correlation with the presence of serum in the medium, with a false discovery rate (FDR) of less than 0.02%. The corresponding expression patterns were organized by hierarchical clustering (Eisen et al. 1998 Proc Natl Acad Sci 95:14863-14868). Genes that were coordinately induced or repressed in response to serum in most samples (Pearson correlation, greater than 90%) were identified. This set of 677 genes, represented by 772 cDNA probes, of which 611 are uniquely identified by UniGene, was termed the common fibroblast serum response gene set. To identify the subset of these 677 genes whose variation in expression was directly related to cell cycle progression, we compared this set of genes to a published set of genes periodically expressed during the HeLa cell cycle (Whitfield et al. 2002 Mol Biol Cell 13: 1977-2000). Because both datasets were generated using similar cDNA microarrays, we tracked genes by the IMAGE number of the cDNA clones on the microarrays. The majority of the genes in the fibroblast serum response gene set showed no evidence of periodic expression during the HeLa cell cycle. One hundred sixty-five genes, represented by 199 cDNA clones, overlapped with the cell cycle gene list; the remaining 512 genes, represented by 573 clones, of which 459 are uniquely identified in UniGene, was termed the CSR gene set.

The patterns of expression in human tumors of the 512 genes of the fibroblast CSR gene set were analyzed using data from published tumor expression profiles. We used the Unigene unique identifier to match genes represented in different microarray platforms. For cDNA microarrays, genes with fluorescent hybridization signals at least 1.5-fold greater than the local background fluorescent signal in the reference channel (Cy3) were considered adequately measured and were selected for further analyses. For Affymetrix data, signal intensity values were first transformed into ratios, using for each gene the mean values of the normalized fluorescence signals across all the samples analyzed as the denominators (Bhattacharjee et al. 2001 Proc Natl Acad Sci 98:13790-13795).

The genes for which technically adequate measurements were obtained from at least 80% of the samples in a given dataset were centered by mean value within each dataset, and average linkage clustering was carried out using the Cluster software (Eisen et al. 1998, supra). In each set of patient samples, the samples were segregated into two classes based on the first bifurcation in the hierarchical clustering dendrogram. For the datasets shown, the clustering and reciprocal expression of serum-induced and serum-repressed genes in the tumor expression data allowed two classes to be unambiguously assigned. Samples with generally high levels of expression of the serum-induced genes and low levels of expression of the serum-repressed genes were classified as "activated"; conversely, samples with generally high levels of expression of serum-repressed genes and low levels of expression of the serum-induced genes were classified as "quiescent." Survival analysis by a Cox-Mantel test was performed in the program Winstat (R. Fitch Software).

In situ hybridization and immunohistochemistry. Digoxigenin-labeled sense and antisense riboprobes for LOXL2 and SDFR1 were synthesized using T7 polymerase-directed in vitro transcription. Sense and antisense riboprobes for SDFR1 were made from nucleotides 51-478 of IMAGE clone 586731 (ATCC #745139), corresponding to the last 388 nucleotides of the 3' end of the coding sequence and 39 nucleotides of the 3' untranslated region. Sense and antisense riboprobes for LOXL2 were made from nucleotides 41-441 of IMAGE clone 882506 (ATCC #1139012), corresponding to the 3' end of the coding sequence. In situ hybridization (ISH) results were considered to have appropriate specificity when we observed a strong, consistent pattern of hybridization of the antisense probe and little or no hybridization of the corresponding sense probe.

Immunohistochemical (IHC) staining was performed using Dako (Glostrup, Denmark) Envision Plus following the manufacturer's instructions. Anti-PLAUR antibody against whole purified human uPA-receptor protein (AB8903; Chemicon, Temecula, Calif., United States) was used at 1:200 dilution. Affinity-purified polyclonal antibody to PLOD2 was produced by immunizing rabbits with peptides (SEQ ID NO:1) EFDTVDLSAVDVHPN, coupled to keyhole limpet hemocyanin (KLH) (Applied Genomics, Inc., Sunnyvale, Calif., United States); affinity-purified antiserum was used for IHC at 1:25,000 dilution. Similarly, affinity-purified polyclonal antibody to ESDN was produced by immunizing rabbits with peptide (SEQ ID NO:2) DHTGQENSWKPKKAR-LKK coupled to KLH (Applied Genomics, Inc.) and used for IHC at 1:12,500 dilution. High-density tissue microarrays containing tumor samples were constructed as described in Kononen et al. (1998) Nat Med 4: 844-847. ISH (Iacubuzio-Donahue et al. 2002 Cancer Res 62: 5351-5357) and IHC (Perou et al. 2000, supra) were as reported. ISH and IHC images and data were archived as described in Liu et al. (2002) Am J Pathol 161: 1557-1565.

The Locus Link accession numbers for the genes discussed in this paper are CORO1C (Locus Link ID 23603), E2F1 (Locus Link ID 1869), ESDN (Locus Link ID 131566), FLNC (Locus Link ID 2318), FOXM1 (Locus Link ID 2305), LOXL2 (Locus Link ID 4017), MIF (Locus Link ID 4282), MYL6 (Locus Link ID 4637), PLAUR (Locus Link ID 5329), PLOD2 (Locus Link ID 5352), PTTG1 (Locus Link ID 9232), SDFR1 (Locus Link ID 27020), TAGLN (Locus Link ID 6876), and TPM2 (Locus Link ID 7169). The accession numbers of the Gene Ontology (GO) terms that appear in Dataset S1 are angiogensis (GO:0001525), blood coagulation (GO:0007596), complement activation (GO:0006956), immune response (GO:0006955), N-linked glycosylation (GO:0006487), protein translation (GO:0006445), and proteolysis and peptidolysis (GO:0006508).

cDNA microarray data: Molecular portrait of breast cancer—62 sporadic breast cancers and 3 pooled normal breast tissues, including 20 pairs of tumors obtained before and after excisional biopsy and doxorubicin-based chemotherapy and 2 pairs of primary tumor and lymph node metastasis. Published by (Perou et al., 2000).

Locally advanced breast cancer—85 breast samples, consisting of 78 carcinomas, 3 fibroadenomas, and 4 normals. 40 of these tumor were previously profiled in Dataset A. A subset of 51 locally advanced primary breast cancers were all treated with excisional biopsy and doxorubicin-based chemotherapy. Clincal endpoint=relapse free survival and disease-specific survival. Published by (Sorlie et al., 2001).

Lung cancer—67 sporadic primary lung carcinomas of different histologic types and stages, including 24 primary adenocarcinomas. 6 normal lung tissues were also profiled. Clinical endpoint=overall survival. Published by (Garber et al., 2001).

Gastric cancer—104 sporadic primary gastric carcinomas with >5 year followup and 24 non-neoplastic gastric mucosa. All patients were treated with gastrectomy alone. Stage III presentation (n=42) was the most common and was analyzed for the clinical endpoint of overall survival. Published by (Leung et al., 2002).

Diffuse large B cell lymphoma—240 DLCL patients with >5 year followup. Clinical endpoint=overall survival. Published by (Rosenwald et al., 2002).

Hepatocellular carcinoma—156 HCC and non-cancerous liver tissues studied by (Chen et al., 2002).

Prostate cancer—100 prostate cancers and adjacent normal tissues profiled by Lapointe et al.

Rosetta ink jet oligonucleotide microarray data. Early breast cancer—78 stage sporadic primary breast carcinomas <5 cm diameter (stage I and IIA) with >5 year clinical followup after lumpectomy. Clinical endpoint=metastasis. Data published by (van't Veer et al., 2002).

Affymetrix Genechip data. Early lung cancer—156 lung samples, including 127 sporadic primary adenocarcinomas of the lung, (62 of which were stage I and II), 12 suspected extrapulmonary metastases, and 17 normal lung samples with >4 year clinical followup. Clinical endpoint=overall survival. Data published by (Bhattacharjee et al., 2001) and stage I and II data selected by (Ramaswamy et al., 2003). Medulloblastoma—60 medulloblastomas with >5 year clinical followup. Clinical endpoint=overall survival. Published by (Pomeroy et al., 2002).

Cross platform mapping and data normalization. Breast Cancer Data (van't Veer et al.): We downloaded and combined the raw microarray hybridization data for 78 Stage I breast tumors from the supplemental materials accompanying Van't veer et al. We then mapped each arrayed feature on the microarrays to the corresponding genes using Batch-SOURCE, where the 24,481 GenBank accessions provided by the authors were used as queries to retrieve UniGene identifiers (build #158, Jan. 15, 2003). Since not all GenBank accessions are represented within UniGene, we could not map 636 (~2.6%) of the arrayed features in this manner. 456 of the 23845 Rosetta array elements that could be mapped corresponded to the fibroblast CSR genes present on our cDNA microarrays, and were used for subsequent analyses. Because the downloadable data were presented as 2-color ratios in log base 10 space, we simply transformed the measurements to log base 2 space to allow comparison to the spotted DNA microarray data. Consistent with the scheme employed for all 2-color hybridization arrays considered in this study, we filtered out genes with fewer than 80% data present (453 genes passed the filter). These data were then processed as detailed in section III below.

Lung Adenocarcinoma (Bhattacharjee et al.): We downloaded raw microarray data (U95A series) for 156 specimens including 127 primary lung adenocarcinomas, 12 suspected extrapulmonary metastases from the lung, and 17 normal lung samples from the supplemental website accompanying Bhattacharjee et al. Because the data provided by the authors were intensity measurements processed by a rank-invariant scaling scheme, we converted these intensities to normalized log-ratios to allow comparison of the corresponding measurements from cDNA microarrays. Specifically, following the protocol employed by Ramaswamy et al, we (1) considered all measurements regardless of Present ("P") or Absent ("A") call, (2) then applied a thresholding filter which arbitrarily sets values less than 20 to 20, and those above 16000 to 16000, and (3) then applied a variation filter such that we only considered those features which exhibited variation of at least 100 in intensity and which showed at least 3-fold difference in the intensity between the highest and lowest expression levels across the 156 microarrays (6349 of 12600 passed these criteria). Following these 3 steps, we then (1) generated ratios by mean centering the expression data for each gene (by dividing the intensity measurement for each gene on a given array by the average intensity of the gene across all 156 arrays), (2) then log-transformed (base 2) the resulting ratios, and (3) then median centered the expression data across arrays then across genes (2 iterations).

UniGene mapping/CSR cross-referencing: We next mapped the 12,454 probe sets (excluding control elements) represented on these U95A Affymetrix microarrays to the corresponding GenBank accessions of the mRNA targets, using the NetAffx resource (Liu et al., 2003) as well as "Table A" from the supplement to Ramaswamy et al. These accessions were then used in BatchSOURCE and LocusLink queries or to retrieve the corresponding UniGene cluster IDs (build #158); in this manner we mapped 11,963 (~96%) probe sets to 9,311 unique UniGene clusters. Of these mapped probe sets, 246 (corresponding to 212 unique UniGene clusters) had corresponding features represented in the CSR gene list, and were used for further analyses as described below.

Medulloblastoma (Pomeroy et al.): we downloaded raw microarray data (HuGeneFL series) for 60 specimens from the supplemental website accompanying Ramaswamy et al. (their 'Dataset E'. Because the data provided by the authors were intensity measurements processed by a linear scaling scheme (Ramaswamy et al., 2003), we converted these intensities to normalized log-ratios to allow comparison of the corresponding measurements from cDNA microarrays. Specifically, following the convention employed by Ramaswamy et al, we (1) considered all measurements regardless of Present ("P") or Absent ("A") call, and (2) then applied a thresholding filter which arbitrarily sets values less than 20 to 20, and those above 16,000 to 16,000. Following these steps, we then (1) generated ratios by mean centering the expression data for each gene (by dividing the intensity measurement for each gene on a given array by the average intensity of the gene across all 60 arrays), (2) then log-transformed (base 2) the resulting ratios, and (3) then median centered the expression data across arrays then across genes (2 iterations). Following these 2 steps, we then (1) generated ratios by mean centering the expression data for each gene (by dividing the intensity measurement for each gene on a given array by the average intensity of the gene across all 60 arrays), (2) then log-transformed (base 2) the resulting ratios, and (3) then median centered the expression data across arrays then across genes (2 iterations).

UniGene mapping/CSR cross-referencing: We next mapped the 7,129 probe sets represented on these HuGeneFL Affymetrix microarrays to the corresponding GenBank accessions of the mRNA targets, using the NetAffx resource (Liu et al., 2003) as well as "Table A" from the supplement to Ramaswamy et al. We retrieved surrogate accessions for probe sets designed from TIGR consensus sequences from Wong Lab website at Harvard University. These accessions were then used in BatchSOURCE and LocusLink queries to retrieve the corresponding UniGene cluster IDs (build #158); we supplemented these mappings with an annotation file from Jean-Marie Rouillard at the University of Michigan. We in this manner mapped 7,079 (~99%). probe sets to 5,691 unique UniGene clusters (Build #158). Of these mapped probe sets, 222 (corresponding to 181 unique UniGene clusters) had corresponding features represented in the CSR gene list, and were used for further analyses as described below.

Classification of Cancers by Fibroblast CSR genes and correlated clinical outcomes. The patterns of expression in human tumors of the 512 genes of the fibroblast CSR gene set were analyzed using data from published tumor expression profiles listed above. We used IMAGE clone identifiers to follow the identity of cDNA probes of Stanford and NIH cDNA microarrays, and used Unigene unique identifier to match genes represented in different microarray platforms. Transformation and normalization of expression data from different platforms are described above.

For cDNA microarray data, genes with fluorescent hybridization signals at least 1.5-fold greater than the local background fluorescent signal in the reference channel (Cy3) were considered adequately measured and were selected for further analyses. The genes for which technically adequate measurements were obtained from at least 80% of the samples in a given dataset were centered by mean value within each dataset, and average linkage clustering was carried out using the Cluster software. In each set of patient samples, the samples were segregated into two classes based on the first bifurcation in the hierarchical clustering "dendrogram". Unless otherwise noted, the clustering and reciprocal expression of serum-induced and serum repressed genes in the tumor expression data allowed two classes to be unambiguously assigned. Samples with generally high levels of expression of the serum-induced genes and low levels of expression of the serum-repressed genes, were classified as "activated"; conversely, samples with generally high levels of expression of serum-repressed genes and low levels of expression of the serum-induced genes were classified as "quiescent". Survival analysis by Cox-Mantel test was performed in the program Winstat (R. Fitch Software).

For results shown in the paper, the expression data of CSR genes for each data set is provided in the cdt file and can be viewed using Treeview. The correlated clinical data are available in Microsoft Excel worksheets as indicated below.

Classification of tumors using fibroblast CSR genes and correlated clinical outcomes. The gene expression data of 58 samples (including 3 normal, 4 fibroadenomas, and 51 locally advanced breast cancers from the same clinical trial) were downloaded from Stanford Microarray Database. Because the data were derived from several batches of microarrays (some containing different numbers of genes), the filtering criteria was relaxed to include genes with technically adequate data in 60% of experiments in order to preserve the expression data stemming from the larger arrays. 218 cDNA probes corresponding to CSR genes (henceforth genes) were present in this dataset and pass the filtering criteria. The expression pattern of these 218 genes were used for hierarchical clustering to define 2 classes were as described above. The 3 normal breasts and 4 fibroadenomas in this dataset were all identified as "quiescent", along with 32 breast tumors. 19 tumors were classified as "activated." The "activated" tumors demonstrated worse outcome in disease-specific survival and relapse free survival (p=0.041 and 0.013, respectively). Applying CSR genes to the entire set of 85 breast carcinomas yielded similar classification result and prognostic stratification.

Classification by Pearson correlation. To evaluate the validity of splitting tumor samples into two classes, we analyzed the expression pattern of CSR genes in the locally advanced breast cancers by an alternative approach that quantifies the similarity of CSR gene expression in tumors vs. in cultured fibroblasts. The expression pattern of CSR genes in the 10 fibroblasts types cultured in 10% FBS was averaged to derive a single number for each gene. The Pearson correlation of the averaged fibroblast expression pattern with each of the breast cancer sample was then calculated. The Pearson correlation data demonstrated at least two groups of breast cancer samples: one group with expression patterns that have positive correlation to the fibroblast serum-induced expression pattern, and a second group with expression patterns that is anti-correlated with serum-induced expression. Plotting the Pearson correlations against uncensored survival time revealed that cancer samples with Pearson correlation greater than 0.2 had decreased survival and relapse-free survival. Using Pearson correlation of 0.2 as the cutoff, Cox-Mantel test confirmed that breast cancers with high correlation to fibroblast serum-induced expression of CSR genes indeed demonstrate poorer disease-specific survival and relapse free survival (p=0.023 and 0.04, respectively).

Lung cancer—all stages. Gene expression data of 67 lung carcinomas and 6 normal lung tissues were downloaded from Stanford Microarray Database. Genes with technically adequate measurement over 80% of experiments were selected; 338 cDNA probes corresponding to CSR genes (henceforth genes) were present in this dataset and pass the filtering criteria. The expression pattern of these 338 genes were used for hierarchical clustering to define 2 classes were as described above. The 6 normal lung tissues in this dataset were all identified as "quiescent". Among 24 primary lung adenocarcinomas with adequate survival information, 10 tumors were classified as "activated" and 14 tumors were classified as "quiescent." The "activated" tumors demonstrated worse overall survival (p=0.001). There was an apparent association between the activated serum phenotype and advanced stage: 7 out of 10 "activated" tumors had distant metastases at the time of presentation while only 3 of 14 patients with "quiescent" tumors had metastases at time of presentation.

Gastric cancer. Gene expression data of 104 gastric carcinomas and 24 non-neoplastic gastric tissues were downloaded from Stanford Microarray Database. Genes with technically adequate measurement over 80% of experiments were selected; 446 cDNA probes corresponding to CSR genes (henceforth genes) were present in this dataset and pass the filtering criteria. The expression pattern of these 446 genes were used for hierarchical clustering to define 2 classes were as described above. The 24 normal gastric tissues in this dataset were all identified as "quiescent". Among 42 stage III primary gastric carcinomas with adequate survival information, 18 tumors were classified as "activated" and 24 tumors were classified as "quiescent." The "activated" tumors demonstrated worse overall survival (p=0.02).

Diffuse large B cell lymphoma. Gene expression data of 240 DLCL samples were downloaded. Genes with technically adequate measurement over 80% of experiments were selected; 198 cDNA probes corresponding to CSR genes (henceforth genes) were present in this dataset and pass the filtering criteria. The expression pattern of these 198 genes were used for hierarchical clustering to define 2 classes were as described above. We did not observe clear reciprocal expression of serum-induced and serum-repressed CSR genes within the samples. Thus, we took the first bifurcation of the hierarchical clustering dendrogram and classified samples as "A" or "B", recognizing that the variation observed here may not have biological meaning. 110 samples were classified as "A" and 130 samples were classified as "B". However, these two groups do not have significant difference in their overall survival (p=0.25).

Hepatocellular carcinoma. Gene expression data of 82 HCC and 74 non-neoplastic liver tissue were downloaded from Stanford Microarray Database. Genes with technically adequate measurement over 80% of experiments were selected; 249 cDNA probes corresponding to CSR genes (henceforth genes) were present in this dataset and pass the filtering criteria. The expression pattern of these 249 genes were used for hierarchical clustering to define 2 classes were as described above. 73 out of 74 non-neoplastic liver tissues in this dataset were identified as "quiescent". 77 out of 82 HCC samples were classified as "activated." Because most tumors had the activated CSR phenotype, we did not analyze possible survival differences.

Prostate cancer. Gene expression data of 59 prostate cancers and 41 non-neoplastic prostate tissue were downloaded from Stanford Microarray Database. Genes with technically adequate measurement over 80% of experiments were selected; 431 cDNA probes corresponding to CSR genes (henceforth genes) were present in this dataset and pass the filtering criteria. The expression pattern of these 431 genes were used for hierarchical clustering to define 2 classes were as described above. 40 out of 41 non-neoplastic prostate tissues in this dataset were identified as "quiescent". 58 out of 59 HCC samples were classified as "activated." Because most tumors had the activated CSR phenotype, we did not analyze possible survival differences.

Early breast cancer. Gene expression data of 78 stage I and IIA breast cancers were downloaded and processes as described above in section II. Genes with technically adequate measurement over 80% of experiments were selected; 453 CSR genes were present in this dataset and pass the filtering criteria. The expression pattern of these 453 genes were used for hierarchical clustering to define 2 classes were as described above. 33 tumors were classified as "activated" and 45 tumors were classified as "quiescent." The "activated" tumors demonstrated worse metastasis-free survival over 10 years of followup (p=0.00046).

Early lung cancer—stage I and II. Gene expression data of 156 lung samples, including 62 stage I and II primary lung adenocarcinomas and 17 normal lung samples were downloaded and processes as described above in section II. Genes with technically adequate measurement over 80% of experiments were selected; 246 CSR genes were present in this dataset and pass the filtering criteria. The expression pattern of these 246 genes were used for hierarchical clustering to define 2 classes were as described above. 16 of 17 normal lung samples were classified as "quiescent." Among the 62 stage I and II primary lung adenocarcinomas, 36 tumors were classified as "activated" and 26 tumors were classified as "quiescent." The "activated" tumors demonstrated worse overall survival (p=0.021).

Medulloblastoma. Gene expression data of 60 medulloblastoma samples were downloaded, transformed, and processed as described in section II. Genes with technically adequate measurement over 80% of experiments were selected; 222 CSR genes present in this dataset pass the filtering criteria. The expression pattern of these 222 genes were used for hierarchical clustering to define 2 classes were as described above. We did not observe clear reciprocal expression of serum-induced and serum-repressed CSR genes within the samples. Thus, we took the first bifurcation of the hierarchical clustering dendrogram and classified samples as "A" or "B", recognizing that the variation observed here may not have biological meaning. 21 samples were classified as "A" and 39 samples were classified as "B". However, these two groups do not have significant difference in their overall survival (p=0.65).

To identify genes that are constitutively and highly expressed in fibroblasts, the global gene expression data of 50 fibroblast cultures was selected as follows. The median Cy5 fluorescence signal over background (representing expression of genes in fibroblasts) for each array element was filtered for regression >0.6 over the element, Cy3 channel (representing reference RNA) signal $\geq 1.5$ fold over background, 80% informative data and variance less than 2 fold in 5 arrays over the 50 experiments. These filtering criteria identified 12959 array elements out of 44600 on the microarray. The Cy5 fluorescence signal of each gene was then averaged for the 50 experiments and ranked from high to low. Genes already identified as the universal fibroblast serum response were removed from this list. The top 1% this ranked gene list (122 out of 12213) was termed "top 1% fibroblast genes."

To determine whether the top 1% fibroblast genes also had prognostic power in breast cancer, IMAGE clone number was used to map the genes in this list to array elements in breast cancer gene expression. 98 out of 122 genes were mapped. The extracted expression data was centered by mean, filtered for genes that were present for 80% of experiments, and the breast cancer samples were organized by the expression pattern of these genes as described above using hierarchical clustering. The top 1% fibroblast genes were up regulated in benign fibroadenomas, which is consistent with the known biology of fibroadenomas and confirms the selection of fibroblast-enriched genes. However, separation of 51 breast cancer samples into 2 groups based on this gene list did not identify a statistically significant survival difference between these two groups (p=0.75).

To compare the prognostic value of fibroblast CSR to a measure of cell proliferation, we chose to classify breast cancers based on the expression pattern of all genes designated as S or G2/M phase-specific. 535 out of 726 cDNA clones were mapped in the breast cancer data, and 224 out of 535 clones passed the filter criteria as above. The expression patterns and samples were organized by hierarchical clustering; the tumors overexpressing the S and G2/M phase signature demonstrated poorer outcome but with borderline statistical significance in relapse free survival and overall survival (p=0.06 and 0.08, respectively). Thus, although mitotic rate is one of the established criteria for tumor grade, the aggregate gene expression measurement of cell proliferation is not sufficiently robust to predict outcome. This result also indicates that the prognostic power of the fibroblast core serum response genes cannot be solely accounted for by the incomplete removal of genes representing cell cycle progression.

To confirm the interpretation that the common serum response of fibroblasts reflect their diverse roles in wound healing, we asked whether the serum response genes were enriched for biologic processes related to wound healing in the public Gene Ontology annotation database. The common fibroblast serum response were queried against the GO database using the program SOURCE, and enrichment of GO-annotated biologic processes greater than expected by chance was calculated using a hypergeometric distribution model as previously described. Specifically, we compared the number of genes with a particular GO annotation in the query set ("sample succ"/"sample num") versus that ratio calculated for all genes on the microarray ("pop succ"/"pop num"). For genes in the unfiltered, common fibroblast serum response, the predominant biologic process annotations were related to cell proliferation. Once genes that have periodic expression during the cell cycle were removed (FIG. 1B,C), the enriched biologic processes include: blood coagulation (GO: 0007596), angiogensis (GO:0001525), complement activation (GO:0006956), immune response (GO:0006955), proteolysis and peptidolysis (GO:0006508), and secretory protein synthesis such as N-linked glycosylation (GO: 0006487) and protein translation (GO:0006445). This result reinforces the idea that the common transcriptional response of fibroblasts to serum in vitro recapitulates their multifaceted roles in wound healing in vivo.

To understand how many of the CSR genes were driving the classification of tumors into two classes (Activated vs. Quiescent), we performed SAM analysis on the CSR gene expression patterns in two breast cancer datasets examined in this study (datasets B and H above). SAM is a permutation-based algorithm that calculates a false discovery rate (FDR) analogous to traditional p-values but has added advantages. Of 217 CSR genes in the Sorlie dataset, 108 (50%) of the CSR genes were significantly different (FDR<0.05) between the activated vs. the quiescent samples. Of the 456 CSR genes in the van't Veer dataset, 237 genes (52%) were significantly different (FDR<0.05) between the activated and quiescent samples. Thus, a significant subset of the CSR genes are providing discriminating power to the tumor classification, highlighting the link between wound healing and cancer progression.

To address the level of redundancy of CSR genes in achieving tumor classification, we applied a shrunken centroid analysis in the program Prediction Analysis of Microarrays (PAM). Using a 10-fold balanced leave-one-out training and testing procedure, we discovered that as few as 35 CSR genes could recapitulate the classification in the Sorlie dataset, and as few as 38 CSR genes could recapitulate the classification in the van't Veer dataset. In other words, a minimum of 6% of CSR genes may accomplish the diagnostic task. Because different published cancer gene expression datasets contain varying number of CSR genes, the robustness of the CSR gene classification underlies our success in using this one set of genes in stratifying prognosis in multiple types of human cancers. Nevertheless, we have noted that different subsets of CSR genes are more distinct in different types of cancers.

Example 2

Based on the hypothesis that normal wound healing and cancer metastasis may share many common features, we identified consistent features in the transcriptional response of normal fibroblasts to serum, and used this wound response signature to reveal links between wound healing and cancer progression in a variety of common epithelial tumors. Here we show in a consecutive series of 295 early breast cancer patient that tumors showing an activated wound response signature (N=126) had decreased distant metastasis-free probability and overall survival compared to those with a quiescent signature (10 year DMFP=51% vs. 75% and OS=51% vs. 84%, P value=$10^{-6}$ and $10^{-10}$, respectively). We establish a gene expression centroid of the wound signature that allows the signature to be applied to individual samples prospectively and quantitatively, and enables the signature to be scaled to suit different clinical purposes.

Moreover, we find that the wound response signature improves risk stratification independently of known clinical and pathologic risk factors and previously established prognostic signatures based on unsupervised hierarchical clustering ("molecular subtypes") or supervised predictors of metastasis ("70-gene prognosis signature"). These results demonstrate that hypothesis-driven gene expression signatures of biological processes can provide order and meaning to heterologous data, and is a powerful approach to decipher the complex biology of human diseases.

Materials and Methods

Tumor Gene Expression Profiles. Detailed patient information has been described previously. RNA isolation, labeling of complementary RNA, competitive hybridization of each tumor cRNA with pooled reference cRNA from all samples to 25,000 element oligonucleotide microarrays, and measurement of expression ratios were previously described (van't Veer et al. (2002) *Nature* 415, 530-6).

Data Analysis

Prognostic signatures. Genes on Stanford cDNA microarrays and Rosetta/NKI oligonucleotide microarrays were mapped across different platforms using Unigene identifiers. This older build of Unigene was used to allow comparison with 2 previously published cross-platform analyses. In the unsupervised analysis, 295 tumor samples were grouped by similarity of the expression pattern of the CSR genes (for which technically adequate data were obtained from at 80% of samples) by average linkage clustering using the software Cluster; the gene expression values were centered by mean.

The samples were segregated into two classes based on the first bifurcation of the clustering dendrogram; the two classes were identified as "Activated" vs. "Quiescent" by the predominant expression of the serum-induced and serum repressed CSR genes. Classification of the tumors as having a good prognosis signature or a poor prognosis signature based on the expression of 70 genes was as described above. The 5 class "intrinsic gene" signature was assigned by matching the expression value of the intrinsic genes in the NKI dataset to the nearest expression centroid of the 5 classes as described; samples that did not have correlation >0.1 to any centroid were termed unclassified. 509 probes representing 431 genes out of 487 intrinsic genes were successfully identified in the NKI data set.

Survival analysis. Overall survival (OS) was defined by death from any cause. Distant metastasis-free probability (DMFP) was defined by a distant metastasis as a first recurrence event; data on all patients were censored on the date of the last follow-up visit, death from causes other than breast cancer, the recurrence of local or regional disease, or the development of a second primary cancer, including contralateral breast cancer. Kaplan-Meier survival curves were compared by the Cox-Mantel log-rank test in Winstat® for Excel. Multivariate analysis by the Cox proportional hazard method was performed using the software package SPSS 11.5 (SPSS, Inc.).

Scaling the wound signature. The patient dataset was randomized into two halves, one for training and one for testing. The two half sets were matched for all known clinical parameters and risk factors (Table 2). The serum-activated fibroblast centroid was as described (Chang et al. (2004) *PLoS Biology* 2, E7). Pearson correlation of the expression values of CSR genes of tumor samples to the serum-activated fibroblast centroid results in a quantitative score reflecting the wound response signature for each sample. The higher the correlation value, the more the sample resembles serum-activated fibroblasts ("activated" wound response signature). A negative correlation value indicates the opposite behavior and higher expression of the "quiescent" wound response signature. The threshold for the two classes can be moved up or down from zero depending on the clinical goal. Sensitivity and specificity for predicting metastasis as the first recurrence event was calculated for every threshold between −1 and +1 for the correlation score in 0.05 increments. The threshold value of negative 0.15 correlation gave 90% sensitivity for metastasis prediction in the training set, and had equivalent performance in the test-set.

Decision Tree Analysis. To construct a decision tree, we considered all clinical risk factors and gene expression profiles using the Cox proportional hazard model in SPSS, identified the dominant risk factor (most significant p value) to segregate patients, and reiterated the process on each subgroup until the patients or risk factors became exhausted. For gene expression signatures, we used the correlation value to each canonical centroid as a continuous variable to capture the possibility that different thresholds may be optimal in different subgroups. Because 61 patients with lymph node negative disease in this series were used to train the 70 gene signature, performance of the decision tree incorporating the 70 gene signature was validated on the independent subset of patients with lymph node positive disease. The threshold for the 70-gene signature was previously reported; the threshold for the wound response signature was chosen based on outcome data in the training set. Performance of the decision tree analysis was validated by equal performance in the randomized training and testing sets of patients. Support of the decision tree model by non-linear multivariate analysis is described in FIG. 12.

Figure 6:
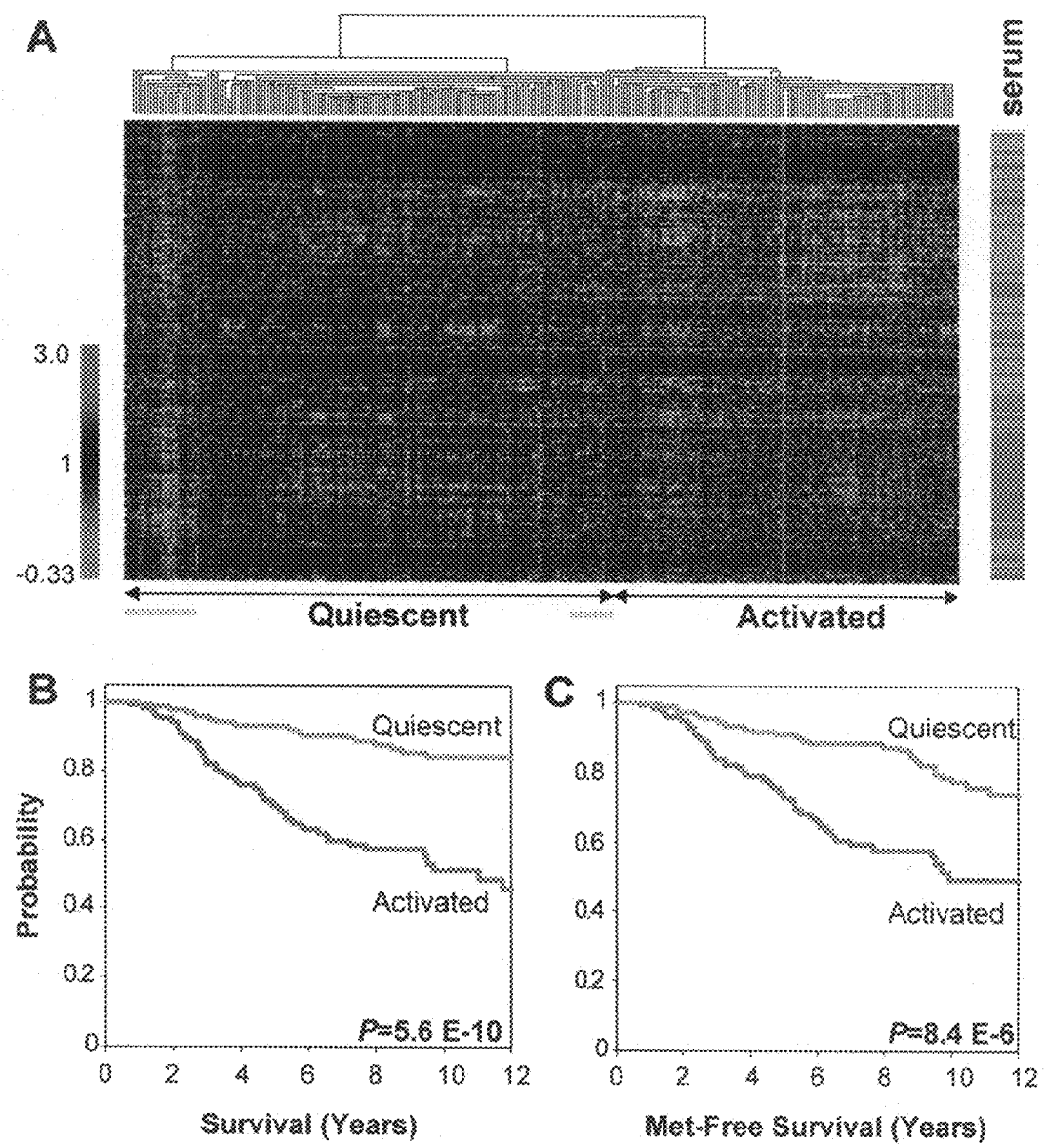
FIGS. 6A-6C. Prognostic value of fibroblast core serum response in breast cancer.

Prognostic Value of a Wound Response Gene Expression Signature in Breast Cancer. To validate the prognostic value of the wound response signature, we examined the expression of the core serum response genes in 295 consecutive patients with early breast cancer treated at the Netherlands Cancer Institute. 442 probes representing 380 out of 459 core serum response genes were successfully identified in this data set. In order to determine whether the CSR genes showed coherent expression in this new set of patients, we grouped the expression pattern of genes and patients by similarity using hierarchical clustering. As reported above in 2 smaller groups of breast cancer patients, the CSR genes showed a coordinated and biphasic pattern of expression (FIG. 6A). Breast cancer samples showed predominant expression of either serum-induced or serum-repressed genes, allowing us to assign each sample to the "activated" or "quiescent" wound response signature. We tested for association between the wound response signature and the occurrence and timing of several key clinical outcomes. Patients with the activated wound response signature (n=126, 42.7%) had a significantly decreased distant metastasis-free probability ($p=8.6 \times 10^{-6}$) and overall survival ($p=5.6 \times 10^{-10}$) in univariate analysis (FIG. 6B, C). We noted that two small subsets of patients with in the quiescent group have more heterogeneous gene expression patterns (FIG. 6A, yellow bars); these patients that were

TABLE 2

Characteristics of patients in the learning and test subsets.
No significant difference was found between the two subsets.

Figure 10:
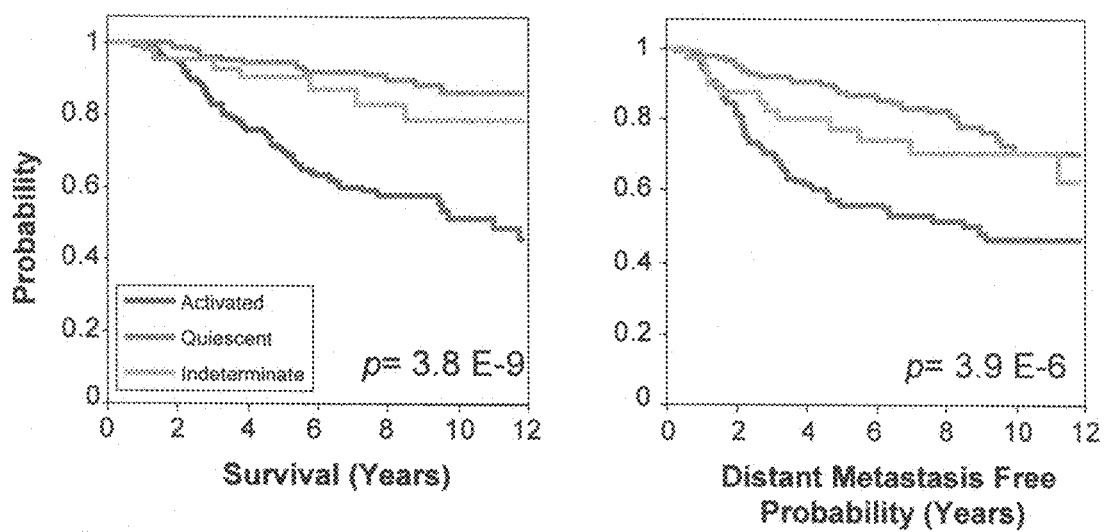
FIG. 10. Clinical outcomes of patients with indeterminate expression of the wound response signature (yellow bar in FIG. 6) are intermediate between patients with activated and quiescent wound response signatures.

|  | Training set (N = 148) | Validation set (N = 147) | All (N = 295) | P-value |
|---|---|---|---|---|
| Overall Survival (10 years) | 69.6% | 70.9% | 70.4% | 0.96 |
| Metastasis-free probability (10 years) | 66.8% | 63.3% | 65.2% | 0.89 |
| T1 vs. T2 | 53%-47% | 52%-48% | 53%-47% | 0.77 |
| pN0-pN1a-pN2a/3a | 51%-36%-13% | 51%-36%-13% | 51%-36%-13% | 1 |
| MST vs. BCT | 45%-55% | 46%-54% | 45%-55% | 0.96 |
| ER+ vs. ER− | 72%-28% | 81%-19% | 77%-23% | 0.08 |
| Grade I-II-III | 27%-30%-43% | 24%-38%-38% | 24%-35%-40% | 0.38 |
| Age 40<>40 | 19%-81% | 24%-46% | 21%-79% | 0.31 |
| CHT yes vs. no | 38%-62% | 37%-63% | 37%-63% | 0.84 |
| 70 genes poor vs. good | 62%-38% | 60%-40% | 61%-39% | 0.69 |
| WS activated vs quiescent | 43%-57% | 42%-58% | 43%-57% | 0.85 | less confidently assigned to the quiescent group had an intermediate risk of metastasis and death from their tumors (FIG. 10).

Figure 7:
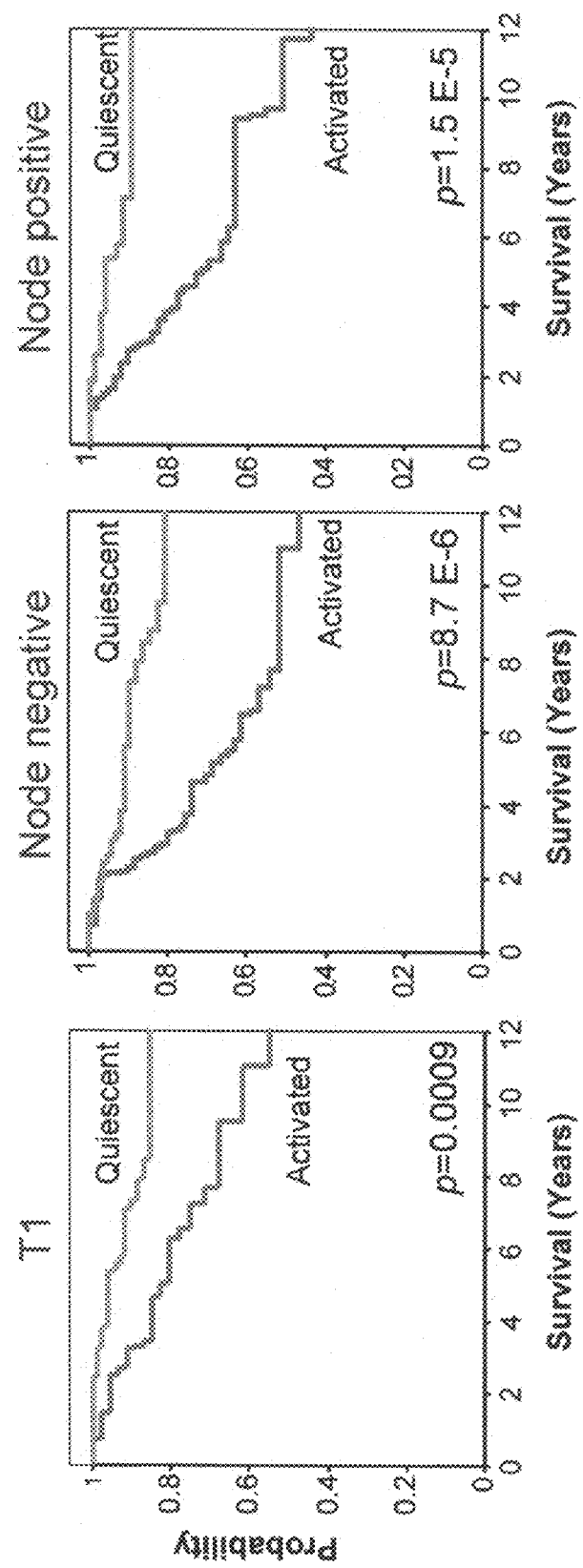
FIG. 7. Decreased survival of tumors with activated wound signature independent of tumor size or lymph node status. Left: In tumors <20 mm (pT1) (N=155, 48 Activated, 107 Quiescent), the 10 year overall survival (OS) for the Activated vs. Quiescent groups are 62% vs. 85%, respectively (p=0.0009). Middle: in lymph node negative patients (N=151, 48 Activated, 103 Quiescent), 10 year OS for the Activated vs. Quiescent group are 52% vs. 80% respectively (p<0.00001). Right: In lymph node positive patients, (N=144, 64 Activated vs. 80 Quiescent), 10 year OS for the Activated vs. Quiescent group are 51% vs. 90% respectively (p=0.00002).

We extended the analysis by separately testing the association of the activated wound response signature and clinical outcome in subsets of breast cancer patients: those with tumors <2.0 cm (T1 tumors); and separately in lymph-node negative disease, and in lymph node positive disease. In each of these subsets of breast cancer patients, patients with tumors showing an activated wound response signature had significantly worse distant metastasis-free probability and overall survival compared to those with a quiescent wound signature (FIG. 7). These results confirm that the wound response signature is a powerful prognostic indicator in breast cancer.

to each class. The threshold for calling a tumor sample wound-like could then be systematically and finely scaled to favor sensitivity or specificity, depending on the clinical scenario. For example, in a screening setting, it may be preferable to favor sensitivity, whereas a clinical test to determine therapies associated with high morbidity should have high specificity.

We first defined the expression pattern of CSR genes in serum-activated serves as the prototype of the "activated" profile of the wound response signature. Thus, we considered a strategy based on the correlation of the expression profile of CSR genes in each tumor sample to a vector representing the centroid of the differential expression in response to serum in cell culture studies of fibroblasts from 10 anatomic sites. The

TABLE 3

Multivariate analysis of prognostic gene expression signatures and clinical risk factors using a linear additive Cox proportional hazard model.

|  | Death | | Metastasis | |
| --- | --- | --- | --- | --- |
|  | Hazard Ratio (95% CI) | P value | Hazard Ratio (95% CI) | P value |
| Wound response signature* | 6.17 (1.11-34.48) | 0.034 | 3.60 (0.71-18.17) | 0.11 |
| 70-gene poor prognosis signature | 4.46 (1.71-11.63) | 0.002 | 4.53 (2.10-9.77) | <0.0001 |
| Molecular subtypes |  |  |  |  |
| Basal | 0.45 (0.047-4.20) | 0.47 | 0.244 (0.042-1.40) | 0.11 |
| Erbb2 | 0.74 (0.085-6.43) | 0.78 | 0.532 (0.11-2.69) | 0.44 |
| Luminal a | 0.79 (0.085-7.38) | 0.83 | 0.679 (0.13-3.53) | 0.64 |
| Luminal b | 0.59 (0.068-5.12) | 0.62 | 0.458 (0.092-2.29) | 0.33 |
| Indeterminate | 0.51 (0.061-4.20) | 0.52 | 0.438 (0.094-2.04) | 0.28 |
| Age (per decade) | 0.75 (0.51-1.10) | 0.13 | 0.821 (0.57-1.18) | 0.27 |
| Diameter of tumor (per cm) | 1.03 (1.00-1.05) | 0.081 | 1.046 (1.02-1.08) | 0.001 |
| Lymph node status (per positive node) | 1.10 (0.98-1.24) | 0.11 | 1.148 (1.04-1.27) | 0.007 |
| Tumor grade |  |  |  |  |
| Grade 2 vs. 1 | 1.93 (0.62-6.08) | 0.25 | 1.262 (0.54-2.91) | 0.58 |
| Grade 3 vs. 1 | 1.70 (0.51-5.69) | 0.38 | 0.972 (0.39-2.42) | 0.95 |
| Vascular invasion |  |  |  |  |
| 1-3 vessels vs. 0 vessels | 0.72 (0.26-2.00) | 0.52 | 0.623 (0.25-1.55) | 0.30 |
| >3 vessels vs. 0 vessels | 1.74 (1.01-2.98) | 0.040 | 1.539 (0.93-2.56) | 0.09 |
| Estrogen receptor status (Positive vs. negative) | 1.85 (0.83-4.12) | 0.12 | 1.400 (0.65-3.03) | 0.38 |
| Mastectomy (vs. breast conserving therapy) | 0.85 (0.51-1.41) | 0.52 | 0.836 (0.52-1.36) | 0.46 |
| No adjuvant chemotherapy | 1.86 (0.99-3.50) | 0.050 | 2.795 (1.53-5.11) | 0.001 |
| No adjuvant hormonal therapy | 1.25 (0.50-3.16) | 0.63 | 1.713 (0.73-4.03) | 0.21 |

*Per 1.0 increment in correlation value to the serum-activated fibroblast centroid. The correlation value to the serum-activated fibroblast centroid was modeled as a continuous variable; the hazard ratio per +1.0 correlation value is reported.
CI = confidence interval.
The hazard ratio per +0.1 correlation value for death and metastasis are 1.20 (95% CI = 1.01-1.42) and 1.14 (95% CI = 0.97-1.34) respectively.
Each molecular subtype was compared to all other subtypes..
Parameters found to be significant (p < 0.05) are shown in bold.
Note that the 70-gene signature was identified based on metastasis prediction of a subset of these patients, thus its performance in this data set may be optimistic.

Creation of a Scalable Prognostic Score based on the Wound Response Signature. The previous analyses depended on stratifying tumors within a pre-defined group, relative to which each tumor is evaluated. To allow practical clinical use of the wound signature, we needed to develop a method to rationally apply and scale the signature so that a newly diagnosed cancer could be scored and classified with respect to the wound response signature by itself. The classification of the new tumor should not influence the classification of previously studied tumors nor be influenced by the addition of other tumors to the data set. Classification by hierarchical clustering provided a mathematically reasonable but biologically arbitrary threshold for assigning a cancer to one of two groups; it is preferable to treat the threshold as a parameter and quantify the confidence with which patients are assigned correlation value to the "serum-activated fibroblast" centroid generates a continuous score that can be scaled. To evaluate the prognostic utility of the scalable wound signature, multivariate analysis of the wound signature with known clinical and pathologic risk factors for breast cancer outcomes showed that the wound signature is an independent predictor of metastasis and death and provides more prognostic information than any of the classical risk factors in the multivariate model (Table 1, hazard ratio of 7 and 11, respectively. P<0.01). Because the pattern of CSR genes in serum-activated fibroblasts was discovered completely independently of tumor gene expression data or clinical outcome, the prognostic power of the serum-activated fibroblast centroid in breast cancer provides strong evidence of the biologic link between wound healing and cancer progression.

TABLE 1

Multivariate analysis of risk factors for death and metastasis
as the first recurrence event in early breast cancer.

|  | Death | | Metastasis | |
|---|---|---|---|---|
|  | Hazard Ratio (95% CI) | P value | Hazard Ratio (95% CI) | P value |
| Wound response signature* | 11.18 (2.52-49.6) | 0.001 | 7.25 (1.75-30.0) | 0.006 |
| Age (per decade) | 0.66 (0.45-0.95) | 0.027 | 0.71 (0.50-1.00) | 0.052 |
| Diameter of tumor (per cm) | 1.02 (0.98-1.04) | 0.270 | 1.03 (1.01-1.06) | 0.008 |
| Lymph node status (per positive node) | 1.05 (0.94-1.16) | 0.371 | 1.10 (1.01-1.21) | 0.035 |
| Tumor grade |  |  |  |  |
| Grade 2 vs. 1 | 2.86 (0.96-8.5) | 0.059 | 1.87 (0.86-4.07) | 0.117 |
| Grade 3 vs. 1 | 3.14 (1.02-9.6) | 0.045 | 1.70 (0.74-3.90) | 0.212 |
| Vascular invasion |  |  |  |  |
| 1-3 vessels vs. 0 vessels | 0.95 (0.35-2.52) | 0.918 | 0.78 (0.32-1.87) | 0.57 |
| >3 vessels vs. 0 vessels | 1.88 (1.13-3.11) | 0.014 | 1.65 (1.02-2.68) | 0.043 |
| Estrogen receptor status (Positive vs. negative) | 0.49 (0.29-0.83) | 0.008 | 0.82 (0.47-1.41) | 0.468 |
| Mastectomy (vs. breast conserving therapy) | 1.23 (0.76-2.01) | 0.401 | 1.28 (0.80-2.04) | 0.311 |
| No adjuvant therapy (vs. chemo or hormonal therapy) | 1.42 (0.80-2.52) | 0.291 | 2.24 (1.32-3.82) | 0.003 |

*The correlation value to the serum activated fibroblast centroid was modeled as a continuous variable; the hazard ratio per +1.0 correlation value is reported and represents the different risks at two ends of the spectrum.
CI is confidence interval.
The hazard ratio per +0.1 correlation value for death and metastasis are 1.27 (95% CI = 1.10-1.48) and 1.22 (95% CI = 1.06-1.40) respectively.
Parameters found to be significant (p < 0.05) in the Cox proportional hazard model are shown in bold.

Improving the Decision whether to Treat Early Breast Cancer Patients with Chemotherapy. Because the wound signature provides improved risk prediction compared to traditional criteria, we examined the utility of a scalable wound signature in a clinical scenario—the decision to treat with adjuvant chemotherapy in early breast cancer. Approximately 30% of women with early breast cancer have clinically occult metastatic disease, and treatment with chemotherapy in addition to surgical excision and radiotherapy improves their outcomes. Uniform treatment of early breast cancer in women young than 50 years of age with chemotherapy increases the 10 year survival from 71% to 78% (absolute benefit of 7%) for lymph node negative disease and from 42% to 53% (absolute benefit of 11%) for lymph node positive disease, but at the cost of exposing a large number of women (89 to 93% of all breast cancer patients) who do not benefit to the morbidities of chemotherapy. The absolute benefit of chemotherapy for older patients is even smaller (3.3% for node negative and 2.7% for node positive patients). Clinical parameters, such as lymph node status, tumor size and histologic grade can provide prognostic information; and are summarized in commonly used clinical guides for deciding whether to treat with chemotherapy such as the National Institute of Health (NIH) or St. Gallen consensus criteria. Nonetheless, risk stratification based on clinical parameters is far from perfect and as a result many women who are unlikely to benefit are treated with chemotherapy.

Because the presence of the wound response signature in the primary tumor is associated with an increased risk of subsequent metastasis, we used a scalable wound signature to identify a subset of patients with a risk subsequent metastasis of less than 10 percent. Within this low-risk population, the expected absolute benefit from chemotherapy would be very small and the decision to forego chemotherapy may be justified. Using the serum-activated fibroblast centroid, we assigned a correlation score to each tumor in the data set. We set a threshold for the correlation score that was able to identify 90% of all patients with subsequent metastasis; this threshold was validated by first learning the threshold in half of the samples and showing an equivalent performance in the remaining half of the data set.

Figure 8:
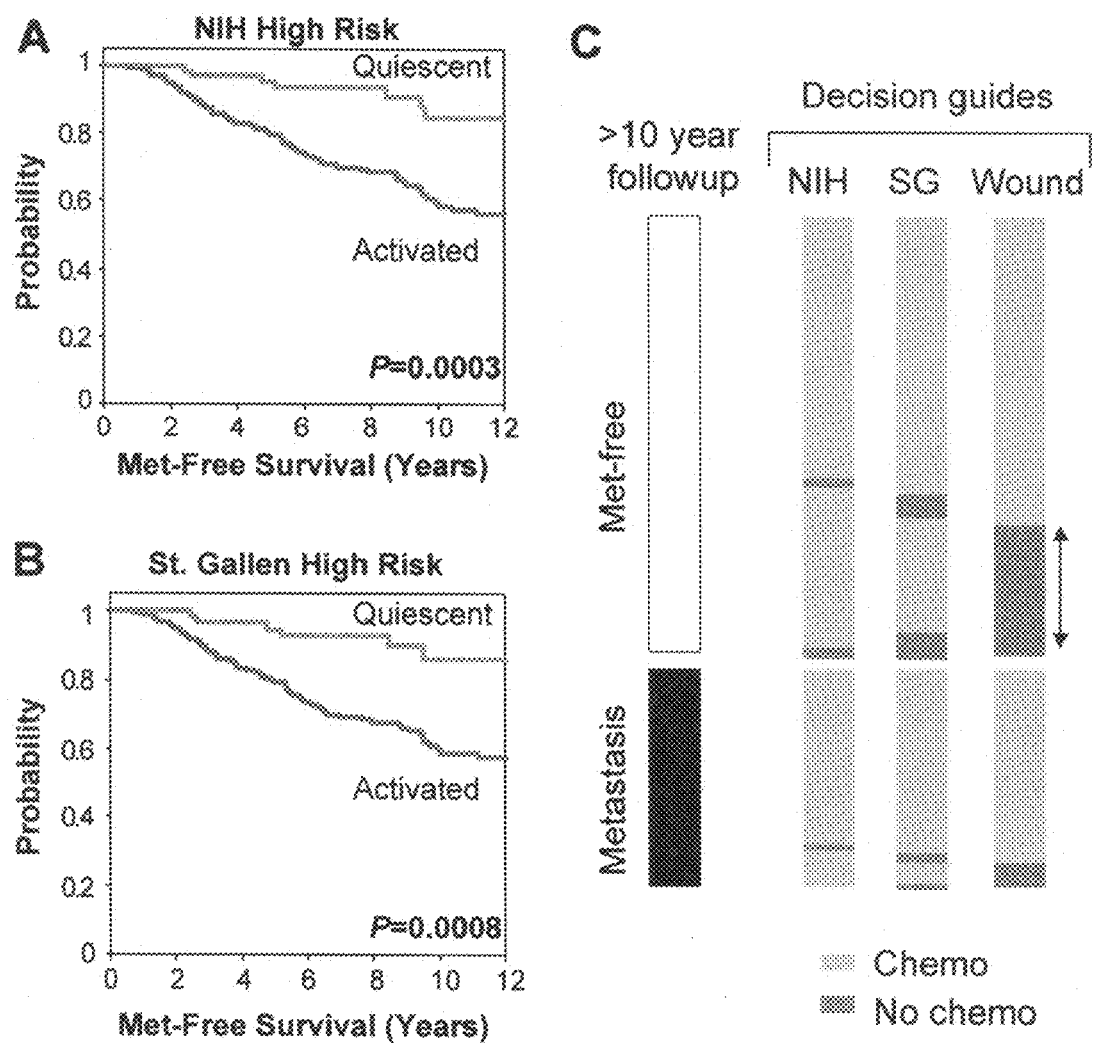
FIGS. 8A-8C. A scalable wound signature as a guide for chemotherapy.

We then tested whether this supervised wound signature provided improved risk stratification compared to traditional clinical criteria. Indeed, patients who were assigned as high risk by the NIH or St. Gallen consensus criteria had heterogeneous outcomes, and within these sets of conventional "high risk" patients, the supervised wound response criterion was able to identify a subset of patients with a low risk of subsequent metastasis (FIG. 8A, B). 185 patients within the NKI dataset were not treated with adjuvant chemotherapy; the clinical outcomes of these patients allowed us to examine the appropriateness of decision for chemotherapy provided by the clinical guidelines or wound signature. As schematized in FIG. 8C, the majority of patients who did not develop metastasis in this series were stratified as high risk by the NIH or St. Gallen criteria, and according to these criteria would have been treated with chemotherapy that would not benefit them. The wound response signature appropriately identified 90% of patients who developed metastases as the first recurrence (the end point of the supervised scaling), and at the same time would have spared 30% of women who did not develop metastasis from exposure to chemotherapy. These results illustrate the potential utility and improved risk stratification of scaling the wound response signature to fit the prognostic goals in a clinical setting.

TABLE 4

Sensitivity and specificity for predicting distant metastasis as first recurrence: comparison of gene expression profiles and clinical criteria.

|  | Sensitivity | Specificity | False Negative |
|---|---|---|---|
| NIH high risk | 96.6% | 3.9% | 3.4% |
| St. Gallen high risk | 93.2% | 7.7% | 6.8% |
| Wound response signature* | 59.1% | 64.3% | 40.1% |

TABLE 4-continued

Sensitivity and specificity for predicting distant metastasis as first recurrence: comparison of gene expression profiles and clinical criteria.

|  | Sensitivity | Specificity | False Negative |
|---|---|---|---|
| 70-gene signature** | 85.2% | 49.3% | 14.8% |
| Wound response criterion+ | 90.9% | 29.0% | 9.1% |

*Activated vs. Quiescent by hierarchical clustering.
**Good vs. Poor
+Activated vs. Quiescent; cut off by correlation level −0.15 to the serum-activated fibroblast centroid.

Integration of Diverse Gene Expression Signatures. How can we integrate the information from different prognostic signatures that have been indentified for breast cancer to optimize risk stratification? We focused on three signatures that have been validated in independent studies and represent distinct analytic strategies. Perou et al., supra. used an unsupervised clustering strategy to identify subtypes of locally advanced breast tumors with pervasive differences in global gene expression patterns; the subtypes are thought to represent distinct biologic entities and were associated to different clinical outcomes. At least 5 subtypes were characterized—termed basal-like, ErbB2, luminal A, luminal B, and normal-like—and can be identified by the pattern of expression of a set of 500 "intrinsic genes." In contrast, Van't Veer et al., supra. selected a 70 gene signature based on the association of expression each gene with the likelihood of metastasis within 5 years. The 70 gene signature was trained on a subset of the same of patients used in the present work and its performance had been previously validated on the entire group of 295 patients. Finally, the wound response signature was identified in a hypothesis-driven approach that specifically tested the relationship between genes activated in a wound-like experimental setting and tumor progression. Importantly, these prognostic signatures are defined by expression patterns of distinct sets of genes with little overlap—only 22 genes are shared by 2 signatures (18 of these genes were shared between wound response and the intrinsic gene list), and no gene is present in all 3 signatures.

Figure 9:
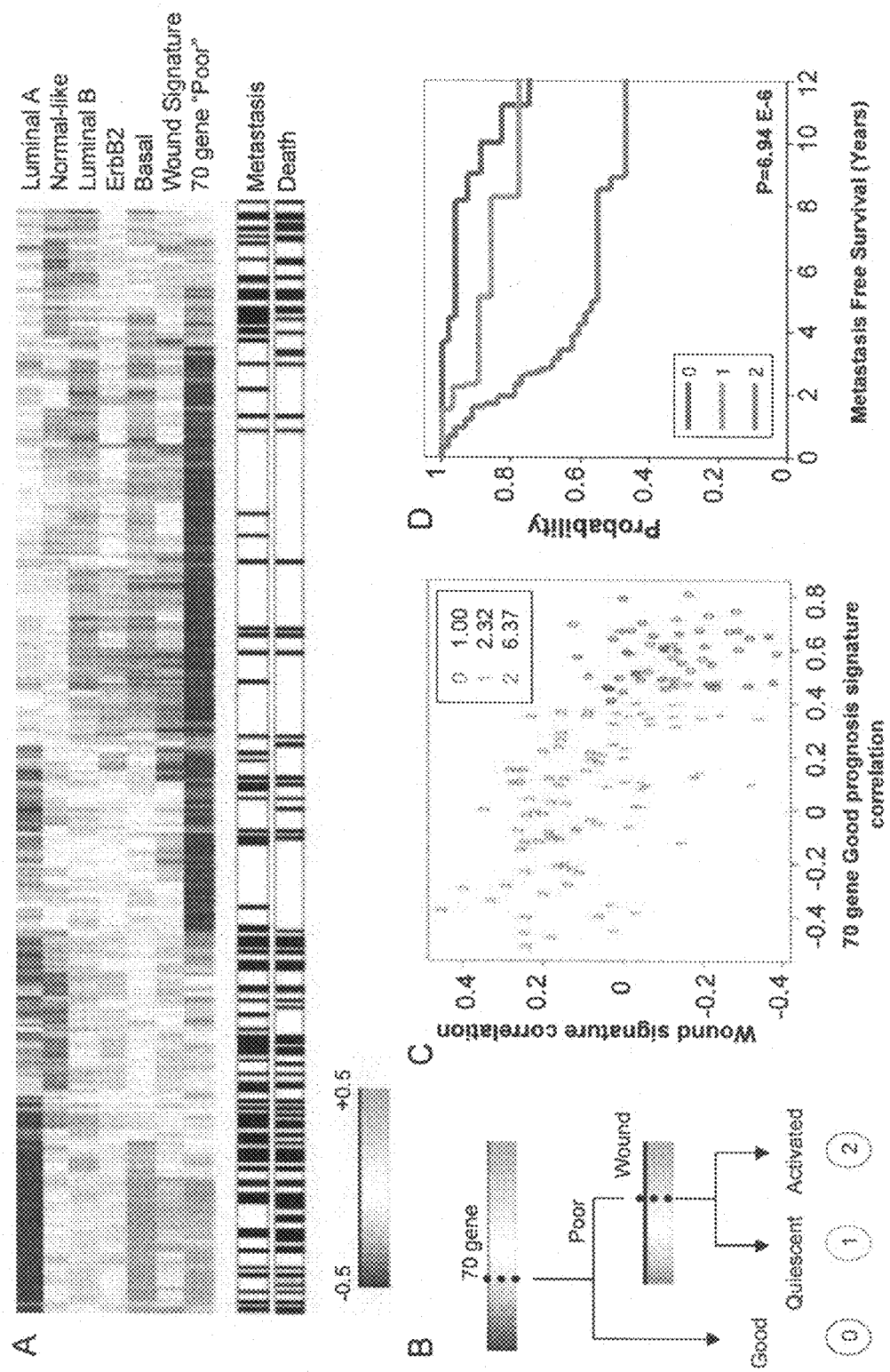
FIGS. 9A-9D. Integration of diverse gene expression signatures for risk prediction.
Figure 11:
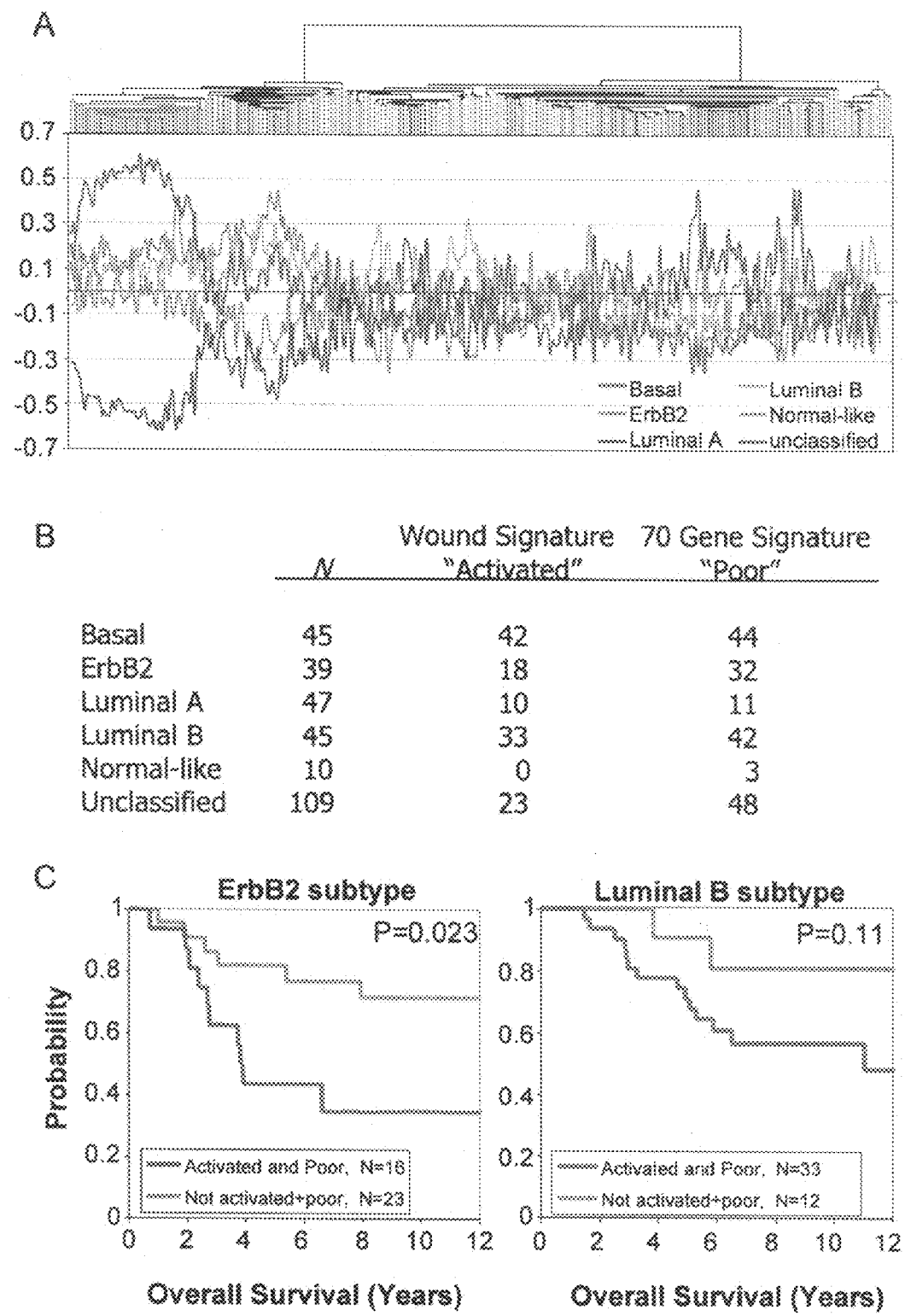
FIGS. 11A-11C. Expression of the 5 molecular subtypes in early breast cancer and improved risk stratification by addition of wound response and 70-gene signatures.

We used each of the three signatures to evaluate this series of 295 breast tumors and found that, despite their different derivations, the signatures gave overlapping and consistent predictions of outcomes (FIG. 10A). Many primary tumors from patients that developed subsequent metastasis and died expressed both the 70-gene poor prognosis signature and the wound response signature; notably a small group of tumors with poor outcome were not identified as having a poor prognosis by the 70-gene signature but were highlighted by the wound response signature (FIG. 9A, right side). Similarly, almost all of the basal-like subgroup, so termed because they express markers characteristic of the basal epithelial cells in breast ducts, expressed the 70-gene poor prognosis signature and the activated wound response signature (FIG. 10, p<0.001, chi square test). These results confirm the notion that the basal-like tumors represent a distinct disease entity with an aggressive clinical course. However, outside of the basal-like subtype, many tumors had mixed expression patterns of several subtypes as defined by the intrinsic genes, and >100 tumors out of 295 could not be confidently assigned to any of the 5 subtypes defined by Perou and Sorlie et al. (FIG. 11). The limited ability to classify these cancers may be due to the incomplete representation of genes that define the intrinsic gene list in this dataset, or due to the fact that the genes that define this classification system were identified in locally advanced breast cancer samples and may not be optimal for classifying earlier stage cancers. In multivariate analysis combining (additively) known clinical risk factors with all 3 signatures, the 70-gene signature and wound response signature provided independent and significant prognostic information while the intrinsic genes did not (Table 2).

Figure 12:
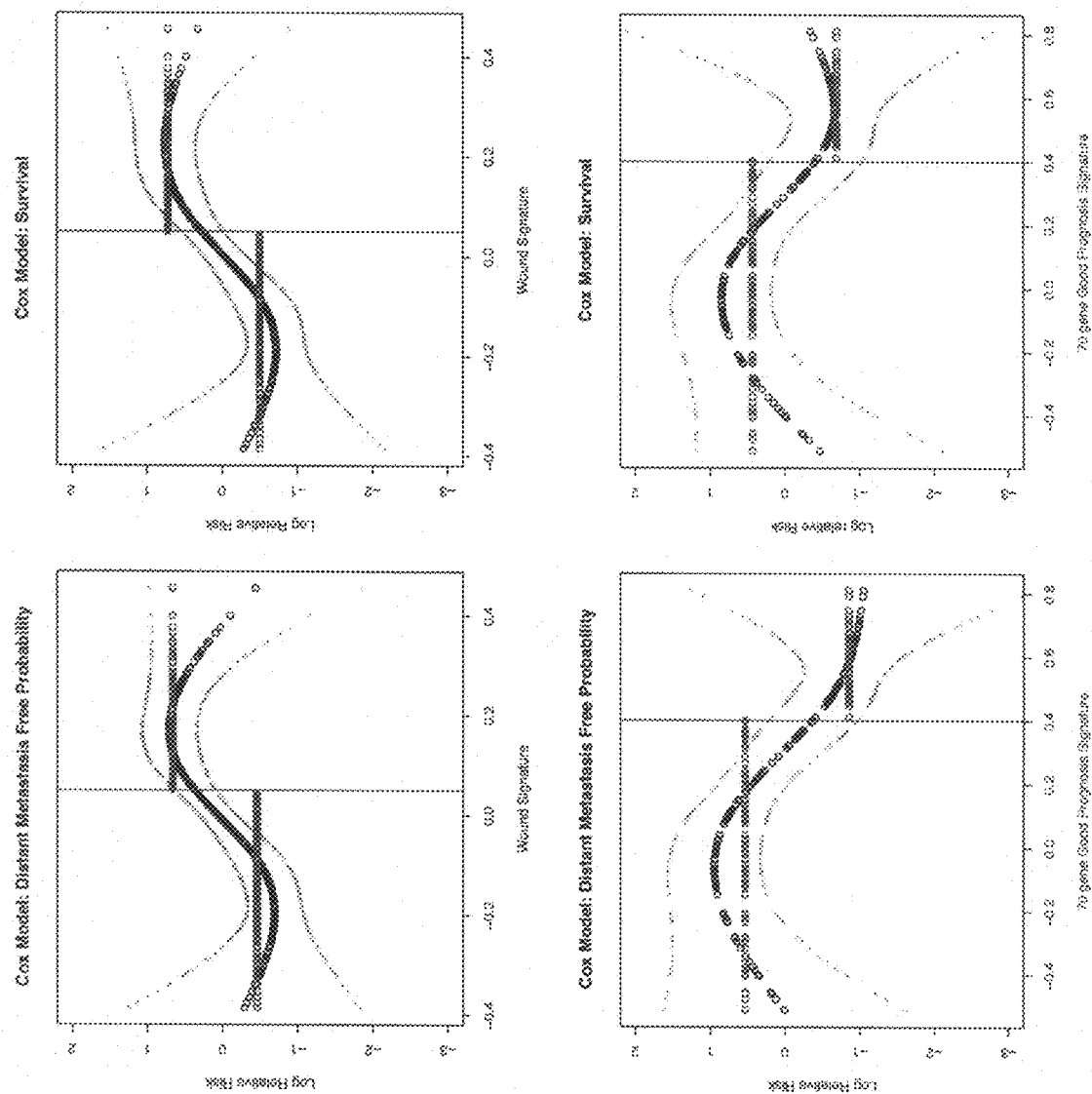
FIG. 12. Nonlinear multivariate analysis of prognostic gene expression signatures and clinical risk factors in early stage breast cancer. Shown are the additive contributions of the Wound signature (top row) and the 70 gene Good Prognosis signature (bottom row) to the log-relative-risk in Cox proportional hazard models, in the presence of all standard risk factors (Table 1). In the left column, the outcome is time to distant metastasis, while in the right it is patient survival time. The black curve in each case represents the contribution of the signature as a smooth function, using a basis of natural cubic splines with 4 interior knots. The green curves are pointwise-standard-error curves about the smooth curves. The blue lines are the result when these continuous scores are fit instead by a pair of constants, obtained by thresholding the scores at the values indicated. Because the thresholds were obtained from the decision tree analysis (FIG. 9B); their mapping to the linear part of the smoothed curves indicates the congruence between the two models. The piecewise-constant fit summarizes the contribution of each of these scores, while the curves give a more detailed contribution. We note that the bends on the extreme two ends of the curves are fitted with less confidence (thus much larger confidence intervals). Although some simple tests indicate evidence for these details, a larger dataset would be required to establish them convincingly.

As an alternative approach to considering information from multiple gene expression signatures for clinical risk stratification, we developed and evaluated a decision tree algorithm to identify patients with clinically meaningful differences in outcome. At each node in the decision tree, we considered all clinical risk factors and gene expression profiles, identified patients with divergent outcomes using the dominant risk factor, and reiterated the process on each subgroup until the patients or risk factors became exhausted. We discovered that in decision trees incorporating gene expression signatures, the 70-gene and wound response signature were sufficient to capture the prognostic information in only 2 steps (FIG. 10B-D). Modeling of nonlinear interactions between the gene expression signatures and clinical risk factors independently yielded a similar conclusion (FIG. 12).

For patients with early breast cancer and lymph node involvement, important clinical decisions are whether to treat with adjuvant chemotherapy and of what type. As previously reported, patients with the favorable 70-gene profile had approximately 90% metastasis-free probability (group 0). Patients whose cancers had a poor prognosis 70-gene profile, but lacked the activated wound response signature, have a risk profile similar to the aggregated average baseline (group 1); patients whose cancers had both the activated wound-response signature and the 70-gene poor prognosis signature had a risk of metastatic disease approximately 6.4 fold higher than did patients in group 0 (10 year DMFP of 89%, 78%, vs. 47%, respectively). Thus, the patients in group 0 might reasonably consider not undergoing adjuvant chemotherapy, whereas the patients in group 2 have a risk profile more similar to patients with locally advanced disease and might be recommended for dose-dense or taxane-based adjuvant chemotherapy. Together, these results illustrate that adding the wound response signature to existing clinical, pathologic, and gene expression prognostic factors can significantly improve risk stratification and clinical decision making.

Using an independent data set, we have confirmed that a wound response gene expression signature is a powerful predictor of clinical outcome in patients with early stage breast cancers. Together with our previous results on locally advanced breast cancer, lung cancer, and gastric cancer, these findings reinforce the concept that a gene expression program related to the physiological response to a wound is frequently activated in common human epithelial tumors, and confers increased risk of metastasis and cancer progression. By delineating the risk for metastasis based on the wound response signature, these high risk breast cancer patients may benefit from therapies that target the wound response.

We have examined approaches to parameterize the wound response signature so that it can be evaluated in tumors individually to yield a quantitative score; the interpretation of the wound signature score can then be rationally directed to suit the clinical task. As a first step toward integrating diverse prognostic signatures, we examined the interactions and information provided by 3 independent methods for using global gene expression patterns to classify breast cancers and predict their course: one that defined 5 molecular subtypes, one that was discovered by directly fitting to survival data, and one based on an in vitro model of wound response. The different signatures classified tumors into coherent and internally consistent groups, and where the signatures diverged, gave improved risk stratification compared to individual signatures. These results show that diverse analytic strategies are continuing to identify distinct molecular features that are related to poor prognosis in these tumors.

Visualizing the connections between the different signatures reveals potential biologic explanations for different clinical outcomes and sets the stage for directed experimentation. For example, the high level activation of the wound signatures in the basal-like subtype of breast cancers raises the possibility that basal epithelial cells in breast ducts have distinct roles in wound healing and may differentially regulate the CSR genes. Finally, the ability of the wound response signature, a gene expression pattern discovered in a cell culture model, to improve cancer risk stratification beyond what had been accomplished using prognostic signatures derived directly from global expression patterns in the cancers themselves highlights the importance of diverse and systematic studies of the human gene expression program in providing a framework for interpreting the complex genomic programs of human diseases.

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 809894 | Hs.14779 | acetyl-Coenzyme A synthetase 2 (ADP forming) | ACAS2 | 0 | −2 |
| IMAGE: 417404 | Hs.227133 | apoptotic chromatin condensation inducer in the nucleus | ACINUS | 0 | −2 |
| IMAGE: 144797 | Hs.8230 | a disintegrin-like and metalloprotease (reprolysin type) with thrombospondin type 1 motif, 1 | ADAMTS1 | 0 | 2 |
| IMAGE: 472185 | Hs.8230 | a disintegrin-like and metalloprotease (reprolysin type) with thrombospondin type 1 motif, 1 | ADAMTS1 | 1 | 0 |
| IMAGE: 796323 | Hs.324470 | adducin 3 (gamma) | ADD3 | 0 | −2 |
| IMAGE: 1558492 | Hs.22599 | atrophin-1 interacting protein 1 | AIP1 | 0 | −2 |
| IMAGE: 245174 | Hs.172788 | ALEX3 protein | ALEX3 | 1 | −2 |
| IMAGE: 251452 | Hs.172788 | ALEX3 protein | ALEX3 | 1 | −2 |
| IMAGE: 283233 | Hs.172788 | ALEX3 protein | ALEX3 | 1 | −2 |
| IMAGE: 785342 | Hs.172788 | ALEX3 protein | ALEX3 | 0 | −2 |
| IMAGE: 825842 | Hs.262476 | adenosylmethionine decarboxylase 1 | AMD1 | 0 | 0 |
| IMAGE: 1942271 | Hs.72160 | AND-1 protein | AND-1 | 0 | 2 |
| IMAGE: 461699 | Hs.172572 | ankyrin repeat domain 10 | ANKRD10 | 0 | 0 |
| IMAGE: 2327739 | Hs.279905 | nucleolar protein ANKT | ANKT | 0 | 0 |
| IMAGE: 461933 | Hs.279905 | nucleolar protein ANKT | ANKT | 1 | 0 |
| IMAGE: 951241 | Hs.279905 | nucleolar protein ANKT | ANKT | 1 | 0 |
| IMAGE: 128711 | Hs.62180 | anillin, actin binding protein (scraps homolog, *Drosophila*) | ANLN | 1 | 0 |
| IMAGE: 129858 | Hs.62180 | anillin, actin binding protein (scraps homolog, *Drosphila*) | ANLN | 0 | 0 |
| IMAGE: 1637791 | Hs.71331 | acidic (leucine-rich) nuclear phosphoprotein 32 family, member E | ANP32E | 0 | 0 |
| IMAGE: 159608 | Hs.75736 | apolipoprotein D | APOD | 1 | −2 |
| IMAGE: 838611 | Hs.75736 | apolipoprotein D | APOD | 0 | −2 |
| IMAGE: 323371 | Hs.177486 | amyloid beta (A4) precursor protein (protease nexin-II, Alzheimer disease) | APP | 0 | −2 |
| IMAGE: 2316441 | Hs.179735 | ras homolog gene family, member C | ARHC | 0 | 2 |
| IMAGE: 290050 | Hs.13531 | Rho GTPase activating protein 12 | ARHGAP12 | 0 | −2 |
| IMAGE: 293745 | Hs.25951 | Rho guanine nucleotide exchange factor (GEF) 3 | ARHGEF3 | 0 | −2 |
| IMAGE: 1703236 | Hs.245540 | ADP-ribosylation factor-like 4 | ARL4 | 0 | 0 |
| IMAGE: 295710 | Hs.26516 | ASF1 anti-silencing function 1 homolog B (*S. cerevisiae*) | ASF1B | 0 | 0 |
| IMAGE: 770377 | Hs.267871 | ATPase, H+ transporting, lysosomal V0 subunit a isoform 1 | ATP6V0A1 | 0 | −2 |
| IMAGE: 1585327 | Hs.127337 | axin 2 (conductin, axil) | AXIN2 | 0 | −2 |
| IMAGE: 753400 | Hs.274350 | BAF53 | BAF53A | 0 | 2 |
| IMAGE: 1015874 | Hs.54089 | BRCA1 associated RING domain 1 | BARD1 | 0 | 0 |
| IMAGE: 2326129 | Hs.87246 | BCL2 binding component 3 | BBC3 | 0 | −2 |
| IMAGE: 415437 | Hs.279862 | BRCA2 and CDKN1A interacting protein | BCCIP | 0 | 2 |
| IMAGE: 201727 | Hs.155024 | B-cell CLL/lymphoma 6 (zinc finger protein 51) | BCL6 | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 826182 | Hs.155024 | B-cell CLL/lymphoma 6 (zinc finger protein 51) | BCL6 | 1 | −2 |
| IMAGE: 230376 | Hs.69771 | B-factor, properdin | BF | 0 | −2 |
| IMAGE: 138728 | Hs.106826 | BRAF35/HDAC2 complex (80 kDa) | BHC80 | 0 | −2 |
| IMAGE: 469297 | Hs.171825 | basic helix-loop-helix domain containing, class B, 2 | BHLHB2 | 0 | −2 |
| IMAGE: 796694 | Hs.1578 | baculoviral IAP repeat-containing 5 (survivin) | BIRC5 | 0 | 0 |
| IMAGE: 448036 | Hs.283532 | uncharacterized bone marrow protein BM039 | BM039 | 1 | 2 |
| IMAGE: 970649 | Hs.283532 | uncharacterized bone marrow protein BM039 | BM039 | 0 | 2 |
| IMAGE: 1456155 | Hs.373498 | potent brain type organic ion transporter | BOCT | 0 | −2 |
| IMAGE: 711698 | Hs.34012 | breast cancer 2, early onset | BRCA2 | 0 | 2 |
| IMAGE: 1844857 | Hs.97515 | BRCA1 interacting protein C-terminal helicase 1 | BRIP1 | 0 | 2 |
| IMAGE: 244767 | Hs.1192 | barren homolog (*Drosphila*) | BRRN1 | 0 | 0 |
| IMAGE: 781047 | Hs.98658 | BUB1 budding uninhibited by benzimidazoles 1 homolog (yeast) | BUB1 | 0 | 0 |
| IMAGE: 842968 | Hs.36708 | BUB1 budding uninhibited by benzimidazoles 1 homolog beta (yeast) | BUB1B | 0 | 0 |
| IMAGE: 742952 | Hs.40323 | BUB3 budding uninhibited by benzimidazoles 3 homolog (yeast) | BUB3 | 0 | 0 |
| IMAGE: 726860 | Hs.32017 | chromosome 11 open reading frame 14 | C11orf14 | 0 | 2 |
| IMAGE: 306446 | Hs.303025 | chromosome 11 open reading frame 24 | C11orf24 | 0 | 2 |
| 1292829 | Hs.121025 | chromosome 11 open reading frame 5 | C11orf5 | 0 | 0 |
| IMAGE: 242840 | Hs.44235 | chromosome 13 open reading frame 1 | C13orf1 | 0 | 2 |
| IMAGE: 703559 | Hs.88523 | chromosome 13 open reading frame 3 | C13orf3 | 0 | 0 |
| IMAGE: 195813 | Hs.274201 | chromosome 1 open reading frame 33 | C1orf33 | 0 | 2 |
| IMAGE: 377346 | Hs.284609 | complement component 1, s subcomponent | C1S | 0 | −2 |
| IMAGE: 85634 | Hs.284609 | complement component 1, s subcomponent | C1S | 1 | −2 |
| IMAGE: 1540227 | Hs.9329 | chromosome 20 open reading frame 1 | C20orf1 | 1 | 0 |
| IMAGE: 2308994 | Hs.9329 | chromosome 20 open reading frame 1 | C20orf1 | 0 | 0 |
| IMAGE: 232837 | Hs.9329 | chromosome 20 open reading frame 1 | C20orf1 | 1 | 0 |
| IMAGE: 80692 | Hs.352413 | chromosome 20 open reading frame 108 | C20orf108 | 0 | −2 |
| IMAGE: 200402 | Hs.70704 | chromosome 20 open reading frame 129 | C20orf129 | 0 | 0 |
| IMAGE: 293727 | Hs.208912 | chromosome 22 open reading frame 18 | C22orf18 | 0 | 0 |
| IMAGE: 79412 | Hs.10235 | chromosome 5 open reading frame 4 | C5orf4 | 0 | −2 |
| IMAGE: 796623 | Hs.88663 | chromosome 6 open reading frame 139 | C6orf139 | 0 | 0 |
| IMAGE: 24208 | Hs.267288 | chromosome 6 open reading frame 55 | C6orf55 | 0 | 2 |
| IMAGE: 121136 | Hs.35453 | chromosome 8 open reading frame 13 | C8orf13 | 0 | 2 |
| IMAGE: 27516 | Hs.13572 | calcium modulating ligand | CAMLG | 0 | −2 |
| IMAGE: 30170 | Hs.74552 | caspase 3, apoptosis-related cysteine protease | CASP3 | 0 | 0 |
| IMAGE: 786084 | Hs.77254 | chromobox homolog 1 (HP1 beta homolog *Drosophila*) | CBX1 | 0 | 2 |
| IMAGE: 814270 | Hs.85137 | cyclin A2 | CCNA2 | 1 | 0 |
| IMAGE: 950690 | Hs.85137 | cyclin A2 | CCNA2 | 0 | 0 |
| IMAGE: 856289 | Hs.194698 | cyclin B2 | CCNB2 | 0 | 0 |
| IMAGE: 455128 | Hs.1973 | cyclin F | CCNF | 0 | 0 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 823691 | Hs.79069 | cyclin G2 | CCNG2 | 0 | −2 |
| IMAGE: 120362 | Hs.143601 | cyclin L2 | CCNL2 | 0 | −2 |
| IMAGE: 884425 | Hs.1600 | chaperonin containing TCP1, subunit 5 (epsilon) | CCT5 | 0 | 2 |
| IMAGE: 1031142 | Hs.22116 | CDC14 cell division cycle 14 homolog B (*S. cerevisiae*) | CDC14B | 1 | −2 |
| IMAGE: 731127 | Hs.22116 | CDC14 cell division cycle 14 homolog B (*S. cerevisiae*) | CDC14B | 1 | −2 |
| IMAGE: 781061 | Hs.22116 | CDC14 cell division cycle 14 homolog B (*S. cerevisiae*) | CDC14B | 0 | −2 |
| IMAGE: 712505 | Hs.334562 | cell division cycle 2, G1 to S and G2 to M | CDC2 | 0 | 0 |
| IMAGE: 898286 | Hs.334562 | cell division cycle 2, G1 to S and G2 to M | CDC2 | 1 | 0 |
| IMAGE: 366057 | Hs.1634 | cell division cycle 25A | CDC25A | 0 | 0 |
| IMAGE: 415102 | Hs.656 | cell division cycle 25C | CDC25C | 0 | 0 |
| IMAGE: 204214 | Hs.69563 | CDC6 cell division cycle 6 homolog (*S. cerevisiae*) | CDC6 | 0 | 0 |
| IMAGE: 731095 | Hs.234545 | cell division cycle associated 1 | CDCA1 | 0 | 0 |
| IMAGE: 814072 | Hs.34045 | cell division cycle associated 4 | CDCA4 | 0 | 2 |
| IMAGE: 753198 | Hs.333893 | cell division cycle associated 7 | CDCA7 | 0 | 0 |
| IMAGE: 2308346 | Hs.19192 | cyclin-dependent kinase 2 | CDK2 | 0 | 2 |
| IMAGE: 301018 | Hs.50905 | cyclin-dependent kinase-like 5 | CDKL5 | 0 | 0 |
| IMAGE: 268652 | Hs.179665 | cyclin-dependent kinase inhibitor 1A (p21, Cip1) | CDKN1A | 0 | −2 |
| IMAGE: 147744 | Hs.106070 | cyclin-dependent kinase inhibitor 1C (p57, Kip2) | CDKN1C | 0 | −2 |
| IMAGE: 700792 | Hs.84113 | cyclin-dependent kinase inhibitor 3 (CDK2-associated dual specificity phosphatase) | CDKN3 | 0 | 0 |
| IMAGE: 2017415 | Hs.1594 | centromere protein A, 17 kDa | CENPA | 0 | 0 |
| IMAGE: 435076 | Hs.77204 | centromere protein F, 350/400ka (mitosin) | CENPF | 0 | 0 |
| IMAGE: 431477 | Hs.283077 | centromere protein J | CENPJ | 0 | 2 |
| IMAGE: 429784 | Hs.433212 | CGI-121 protein | CGI-121 | 0 | 2 |
| IMAGE: 246524 | Hs.20295 | CHK1 checkpoint homolog (*S. pombe*) | CHEK1 | 0 | 2 |
| IMAGE: 71902 | Hs.24641 | cytoskeleton associated protein 2 | CKAP2 | 1 | 0 |
| IMAGE: 825228 | Hs.24641 | cytoskeleton associated protein 2 | CKAP2 | 0 | 0 |
| IMAGE: 812244 | Hs.15159 | chemokine-like factor | CKLF | 0 | 2 |
| IMAGE: 725454 | Hs.83758 | CDC28 protein kinase regulatory subunit 2 | CKS2 | 0 | 0 |
| IMAGE: 288888 | Hs.44563 | hypothetical protein CL640 | CL640 | 0 | 2 |
| IMAGE: 824755 | Hs.211614 | chloride channel 6 | CLCN6 | 0 | −2 |
| IMAGE: 1915913 | Hs.54570 | chloride intracellular channel 2 | CLIC2 | 0 | −2 |
| IMAGE: 470279 | Hs.31622 | contactin associated protein 1 | CNTNAP1 | 0 | −2 |
| IMAGE: 1602675 | Hs.15591 | COP9 subunit 6 (MOV34 homolog, 34 kD) | COPS6 | 0 | 2 |
| IMAGE: 511647 | Hs.17377 | coronin, actin binding protein, 1C | CORO1C | 0 | 2 |
| IMAGE: 813490 | Hs.17377 | coronin, actin binding protein, 1C | CORO1C | 1 | 2 |
| IMAGE: 144849 | Hs.289092 | coactosin-like 1 (Dictyostelium) | COTL1 | 0 | 2 |
| IMAGE: 489823 | Hs.16297 | COX17 homolog, cytochrome c oxidase assembly protein (yeast) | COX17 | 0 | 2 |
| IMAGE: 85313 | Hs.82506 | cell cycle progression 8 protein | CPR8 | 0 | −2 |
| IMAGE: 768262 | Hs.155481 | cartilage associated protein | CRTAP | 0 | −2 |
| IMAGE: 1475574 | Hs.173894 | colony stimulating factor 1 (macrophage) | CSF1 | 0 | −2 |
| IMAGE: 73527 | Hs.173894 | colony stimulating factor 1 (macrophage) | CSF1 | 1 | −2 |
| IMAGE: 949938 | Hs.304682 | cystatin C (amyloid angiopathy and cerebral hemorrhage) | CST3 | 0 | −2 |
| IMAGE: 269997 | Hs.64837 | cystinosis, nephropathic | CTNS | 0 | −2 |
| IMAGE: 1571993 | Hs.11590 | cathepsin F | CTSF | 0 | −2 |
| IMAGE: 295843 | Hs.82568 | cytochrome P450, family 27, subfamily A, polypeptide 1 | CYP27A1 | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 624390 | Hs.6879 | DC13 protein | DC13 | 0 | 2 |
| IMAGE: 43198 | Hs.709 | deoxycytidine kinase | DCK | 0 | 2 |
| IMAGE: 896978 | Hs.115660 | DNA cross-link repair 1B (PSO2 homolog, *S. cerevisiae*) | DCLRE1B | 0 | 2 |
| IMAGE: 281898 | Hs.405925 | differential display and activated by p53 | DDA3 | 0 | 0 |
| IMAGE: 703633 | Hs.405925 | differential display and activated by p53 | DDA3 | 1 | 0 |
| IMAGE: 245774 | Hs.93675 | decidual protein induced by progesterone | DEPP | 0 | −2 |
| IMAGE: 462961 | Hs.83765 | dihydrofolate reductase | DHFR | 0 | 2 |
| IMAGE: 244205 | Hs.83765 | dihydrofolate reductase | DHFR | 1 | 0 |
| IMAGE: 768172 | Hs.83765 | dihydrofolate reductase | DHFR | 1 | 0 |
| IMAGE: 199558 | Hs.124696 | dehydrogenase/reductase (SDR family) member 6 | DHRS6 | 0 | −2 |
| IMAGE: 743182 | Hs.5790 | hypothetical protein dJ37E16.5 | DJ37E16.5 | 0 | 0 |
| IMAGE: 509943 | Hs.4747 | dyskeratosis congenita 1, dyskerin | DKC1 | 0 | 0 |
| IMAGE: 1724716 | Hs.355920 | DKFZP434B103 protein | DKFZP434B103 | 0 | −2 |
| IMAGE: 462333 | Hs.59461 | DKFZP434C245 protein | DKFZP434C245 | 0 | 0 |
| IMAGE: 823655 | Hs.323583 | hypothetical protein DKFZp434L142 | DKFZp434L142 | 0 | −2 |
| IMAGE: 1636060 | Hs.267120 | dactylidin | DKFZP434O1427 | 0 | −2 |
| IMAGE: 136070 | Hs.288771 | DKFZP586A0522 protein | DKFZP586A0522 | 1 | −2 |
| IMAGE: 70152 | Hs.288771 | DKFZP586A0522 protein | DKFZP586A0522 | 0 | −2 |
| IMAGE: 2062453 | Hs.427525 | DKFZP727G051 protein | DKFZP727G051 | 0 | 2 |
| IMAGE: 359504 | Hs.270753 | hypothetical protein DKFZp761L1417 | DKFZp761L1417 | 0 | 2 |
| IMAGE: 1540236 | Hs.104859 | hypothetical protein DKFZp762E1312 | DKFZp762E1312 | 1 | 0 |
| IMAGE: 66406 | Hs.104859 | hypothetical protein DKFZp762E1312 | DKFZp762E1312 | 0 | 0 |
| IMAGE: 196148 | Hs.14478 | hypothetical protein DKFZp762H185 | DKFZp762H185 | 0 | −2 |
| IMAGE: 773383 | Hs.20149 | deleted in lymphocytic leukemia, 1 | DLEU1 | 0 | 2 |
| IMAGE: 270136 | Hs.43628 | deleted in lymphocytic leukemia, 2 | DLEU2 | 0 | 2 |
| IMAGE: 686172 | Hs.77695 | discs, large homolog 7 (*Drosphila*) | DLG7 | 0 | 0 |
| IMAGE: 755228 | Hs.166161 | dynamin 1 | DNM1 | 0 | −2 |
| IMAGE: 752770 | Hs.17834 | downstream neighbor of SON | DONSON | 0 | 0 |
| IMAGE: 767268 | Hs.458134 | dipeptidylpeptidase 7 | DPP7 | 0 | −2 |
| IMAGE: 841620 | Hs.173381 | dihydropyrimidinase-like 2 | DPYSL2 | 0 | −2 |
| IMAGE: 240748 | Hs.29106 | dual specificity phosphatase 22 | DUSP22 | 0 | −2 |
| IMAGE: 773678 | Hs.367676 | dUTP pyrophosphatase | DUT | 0 | 2 |
| IMAGE: 768260 | Hs.96055 | E2F transcription factor 1 | E2F1 | 0 | 0 |
| IMAGE: 22918 | Hs.346868 | EBNA1 binding protein 2 | EBNA1BP2 | 0 | 2 |
| IMAGE: 306921 | Hs.433779 | eukaryotic translation elongation factor 1 epsilon 1 | EEF1E1 | 0 | 2 |
| IMAGE: 795229 | Hs.121073 | EF-hand domain (C-terminal) containing 1 | EFHC1 | 0 | 0 |
| IMAGE: 2017769 | Hs.433317 | eukaryotic translation initiation factor 4E binding protein 1 | EIF4EBP1 | 0 | 2 |
| IMAGE: 25988 | Hs.433750 | eukaryotic translation initiation factor 4 gamma, 1 | EIF4G1 | 0 | 2 |
| IMAGE: 272262 | Hs.7913 | hypothetical protein Ells1 | Ells1 | 0 | 0 |
| IMAGE: 109863 | Hs.29191 | epithelial membrane protein 2 | EMP2 | 0 | 2 |
| IMAGE: 502682 | Hs.102948 | enigma (LIM domain protein) | ENIGMA | 0 | 2 |
| IMAGE: 1637756 | Hs.254105 | enolase 1, (alpha) | ENO1 | 0 | 2 |
| IMAGE: 392678 | Hs.254105 | enolase 1, (alpha) | ENO1 | 1 | 2 |
| IMAGE: 153541 | Hs.78436 | EphB1 | EPHB1 | 0 | 2 |
| IMAGE: 248454 | Hs.93659 | protein disulfide isomerase related protein (calcium-binding protein, intestinal-related) | ERP70 | 0 | 2 |
| IMAGE: 263200 | Hs.173374 | endothelial and smooth muscle cell-derived neuropilin-like protein | ESDN | 0 | 2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 265494 | Hs.173374 | endothelial and smooth muscle cell-derived neuropilin-like protein | ESDN | 1 | 2 |
| IMAGE: 782460 | Hs.173374 | endothelial and smooth muscle cell-derived neuropilin-like protein | ESDN | 1 | 2 |
| IMAGE: 447208 | Hs.47504 | exonuclease 1 | EXO1 | 0 | 0 |
| IMAGE: 770992 | Hs.77256 | enhancer of zeste homolog 2 (*Drosphila*) | EZH2 | 0 | 0 |
| IMAGE: 310519 | Hs.47913 | coagulation factor X | F10 | 0 | −2 |
| IMAGE: 1928791 | Hs.62192 | coagulation factor III (thromboplastin, tissue factor) | F3 | 0 | 2 |
| IMAGE: 298409 | Hs.49881 | fatty acid binding protein 3, muscle and heart (mammary-derived growth inhibitor) | FABP3 | 0 | −2 |
| IMAGE: 1758590 | Hs.268012 | fatty-acid-Coenzyme A ligase, long-chain 3 | FACL3 | 1 | −2 |
| IMAGE: 310493 | Hs.268012 | fatty-acid-Coenzyme A ligase, long-chain 3 | FACL3 | 1 | −2 |
| IMAGE: 49944 | Hs.268012 | fatty-acid-Coenzyme A ligase, long-chain 3 | FACL3 | 0 | −2 |
| IMAGE: 782503 | Hs.132898 | fatty acid desaturase 1 | FADS1 | 0 | −2 |
| IMAGE: 128329 | Hs.184641 | fatty acid desaturase 2 | FADS2 | 1 | −2 |
| IMAGE: 878174 | Hs.184641 | fatty acid desaturase 2 | FADS2 | 0 | −2 |
| IMAGE: 770424 | Hs.8047 | Fanconi anemia, complementation group G | FANCG | 0 | 0 |
| IMAGE: 358643 | Hs.23111 | phenylalanine-tRNA synthetase-like | FARSL | 0 | 2 |
| IMAGE: 68894 | Hs.111903 | Fc fragment of IgG, receptor, transporter, alpha | FCGRT | 0 | −2 |
| IMAGE: 770394 | Hs.111903 | Fc fragment of IgG, receptor, transporter, alpha | FCGRT | 1 | −2 |
| IMAGE: 80410 | Hs.335918 | farnesyl diphosphate synthase (farnesyl pyrophosphate synthetase, dimethylallyltranstransferase, geranyltranstransferase) | FDPS | 0 | −2 |
| IMAGE: 951142 | Hs.4756 | flap structure-specific endonuclease 1 | FEN1 | 0 | 0 |
| IMAGE: 842767 | Hs.21331 | hypothetical protein FLJ10036 | FLJ10036 | 0 | 2 |
| IMAGE: 773147 | Hs.86211 | hypothetical protein FLJ10156 | FLJ10156 | 0 | 0 |
| IMAGE: 1664710 | Hs.104650 | hypothetical protein FLJ10292 | FLJ10292 | 0 | 2 |
| IMAGE: 824126 | Hs.30738 | hypothetical protein FLJ10407 | FLJ10407 | 0 | 2 |
| IMAGE: 292936 | Hs.48855 | hypothetical protein FLJ10468 | FLJ10468 | 0 | 0 |
| IMAGE: 346834 | Hs.42484 | hypothetical protein FLJ10618 | FLJ10618 | 0 | −2 |
| IMAGE: 626206 | Hs.334828 | hypothetical protein FLJ10719 | FLJ10719 | 0 | 0 |
| IMAGE: 773605 | Hs.8768 | hypothetical protein FLJ10849 | FLJ10849 | 0 | −2 |
| IMAGE: 307328 | Hs.34579 | hypothetical protein FLJ10948 | FLJ10948 | 0 | −2 |
| IMAGE: 277808 | Hs.29716 | hypothetical protein FLJ10980 | FLJ10980 | 0 | 0 |
| IMAGE: 1572724 | Hs.23363 | hypothetical protein FLJ10983 | FLJ10983 | 0 | 2 |
| IMAGE: 462861 | Hs.274448 | hypothetical protein FLJ11029 | FLJ11029 | 0 | 0 |
| IMAGE: 809383 | Hs.12151 | hypothetical protein FLJ11286 | FLJ11286 | 0 | −2 |
| IMAGE: 435619 | Hs.374421 | hypothetical protein FLJ12643 | FLJ12643 | 0 | 2 |
| IMAGE: 1880814 | Hs.323537 | hypothetical protein FLJ12953 similar to *Mus musculus* D3Mm3e | FLJ12953 | 0 | 2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 346308 | Hs.47125 | hypothetical protein FLJ13912 | FLJ13912 | 0 | 0 |
| IMAGE: 290057 | Hs.26812 | hypothetical protein FLJ14525 | FLJ14525 | 1 | −2 |
| IMAGE: 810603 | Hs.26812 | hypothetical protein FLJ14525 | FLJ14525 | 0 | −2 |
| IMAGE: 1697632 | Hs.246875 | hypothetical protein FLJ20059 | FLJ20059 | 0 | −2 |
| IMAGE: 124242 | Hs.10346 | hypothetical protein FLJ20154 | FLJ20154 | 0 | −2 |
| IMAGE: 812137 | Hs.50848 | hypothetical protein FLJ20331 | FLJ20331 | 0 | 2 |
| IMAGE: 590253 | Hs.79828 | hypothetical protein FLJ20333 | FLJ20333 | 0 | 0 |
| IMAGE: 645565 | Hs.133260 | hypothetical protein FLJ20354 | FLJ20354 | 0 | 0 |
| IMAGE: 882355 | Hs.32471 | hypothetical protein FLJ20364 | FLJ20364 | 0 | 0 |
| IMAGE: 549572 | Hs.426696 | hypothetical protein FLJ20516 | FLJ20516 | 0 | 0 |
| IMAGE: 858915 | Hs.289069 | hypothetical protein FLJ21016 | FLJ21016 | 0 | −2 |
| IMAGE: 1696374 | Hs.255416 | hypothetical protein FLJ21986 | FLJ21986 | 0 | −2 |
| IMAGE: 838446 | Hs.31297 | duodenal cytochrome b | FLJ23462 | 0 | −2 |
| IMAGE: 782259 | Hs.38178 | hypothetical protein FLJ23468 | FLJ23468 | 1 | 2 |
| IMAGE: 814769 | Hs.38178 | hypothetical protein FLJ23468 | FLJ23468 | 0 | 0 |
| IMAGE: 1618978 | Hs.165607 | hypothetical protein FLJ25416 | FLJ25416 | 0 | 0 |
| IMAGE: 320865 | Hs.124740 | hypothetical protein FLJ30532 | FLJ30532 | 0 | 2 |
| IMAGE: 1941536 | Hs.350388 | hypothetical protein FLJ30574 | FLJ30574 | 0 | −2 |
| IMAGE: 1474390 | Hs.30818 | hypothetical protein FLJ31033 | FLJ31033 | 0 | −2 |
| IMAGE: 365177 | Hs.380474 | hypothetical protein FLJ32731 | FLJ32731 | 0 | −2 |
| IMAGE: 788596 | Hs.98133 | hypothetical protein FLJ32915 | FLJ32915 | 0 | 2 |
| IMAGE: 824913 | Hs.99807 | hypothetical protein FLJ40629 | FLJ40629 | 0 | 0 |
| IMAGE: 767172 | Hs.8963 | hypothetical protein FLJ90754 | FLJ90754 | 0 | −2 |
| IMAGE: 489509 | Hs.28264 | hypothetical protein FLJ90798 | FLJ90798 | 0 | −2 |
| IMAGE: 2321104 | Hs.58414 | filamin C, gamma (actin binding protein 280) | FLNC | 0 | 2 |
| IMAGE: 564803 | Hs.239 | forkhead box M1 | FOXM1 | 0 | 0 |
| IMAGE: 815072 | Hs.9081 | phenylalanyl-tRNA synthetase beta-subunit | FRSB | 0 | 2 |
| IMAGE: 823659 | Hs.257267 | FYVE and coiled-coil domain containing 1 | FYCO1 | 0 | −2 |
| IMAGE: 81409 | Hs.336429 | GABA(A) receptor-associated protein like 1 | GABARAPL1 | 0 | −2 |
| IMAGE: 298231 | Hs.167017 | gamma-aminobutyric acid (GABA) B receptor, 1 | GABBR1 | 0 | −2 |
| IMAGE: 1582149 | Hs.294088 | GAJ protein | GAJ | 0 | 0 |
| IMAGE: 42558 | Hs.75335 | glycine amidinotransferase (L-arginine: glycine amidinotransferase) | GATM | 0 | −2 |
| IMAGE: 627401 | Hs.17839 | TNF-induced protein | GG2-1 | 0 | −2 |
| IMAGE: 809588 | Hs.78619 | gamma-glutamyl hydrolase (conjugase, folylpolygammaglutamyl hydrolase) | GGH | 0 | 2 |
| IMAGE: 196012 | Hs.239189 | glutaminase | GLS | 0 | −2 |
| IMAGE: 193883 | Hs.234896 | geminin, DNA replication inhibitor | GMNN | 1 | 0 |
| IMAGE: 813586 | Hs.234896 | geminin, DNA replication inhibitor | GMNN | 0 | 0 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 1636447 | Hs.83381 | guanine nucleotide binding protein (G protein), gamma 11 | GNG11 | 0 | 2 |
| IMAGE: 1656488 | Hs.272529 | glycosylphosphatidylinositol specific phospholipase D1 | GPLD1 | 0 | 2 |
| IMAGE: 486493 | Hs.17270 | G protein-coupled receptor 124 | GPR124 | 0 | −2 |
| IMAGE: 214990 | Hs.290070 | gelsolin (amyloidosis, Finnish type) | GSN | 0 | −2 |
| IMAGE: 2019372 | Hs.122552 | G-2 and S-phase expressed 1 | GTSE1 | 0 | 0 |
| IMAGE: 785897 | Hs.122552 | G-2 and S-phase expressed 1 | GTSE1 | 1 | 0 |
| IMAGE: 256664 | Hs.147097 | H2A histone family, member X | H2AFX | 0 | 0 |
| IMAGE: 2315147 | Hs.119192 | H2A histone family, member Z | H2AFZ | 0 | 2 |
| IMAGE: 249949 | Hs.301005 | histone H2A.F/Z variant | H2AV | 0 | −2 |
| IMAGE: 1679531 | Hs.159226 | hyaluronan synthase 2 | HAS2 | 0 | 2 |
| IMAGE: 2116188 | Hs.9028 | histone deacetylase 5 | HDAC5 | 0 | −2 |
| IMAGE: 511388 | Hs.6679 | headcase homolog (Drosophila) | HECA | 0 | −2 |
| IMAGE: 789091 | Hs.28777 | histone 1, H2ac | HIST1H2AC | 0 | 0 |
| IMAGE: 970591 | Hs.427696 | high-mobility group box 1 | HMGB1 | 0 | 2 |
| IMAGE: 290111 | Hs.77910 | 3-hydroxy-3-methylglutaryl-Coenzyme A synthase 1 (soluble) | HMGCS1 | 1 | −2 |
| IMAGE: 704519 | Hs.77910 | 3-hydroxy-3-methylglutaryl-Coenzyme A synthase 1 (soluble) | HMGCS1 | 0 | −2 |
| IMAGE: 73252 | Hs.77910 | 3-hydroxy-3-methylglutaryl-Coenzyme A synthase 1 (soluble) | HMGCS1 | 1 | −2 |
| IMAGE: 1845630 | Hs.181163 | high-mobility group nucleosomal binding domain 2 | HMGN2 | 0 | 2 |
| IMAGE: 241826 | Hs.181163 | high-mobility group nucleosomal binding domain 2 | HMGN2 | 1 | 2 |
| IMAGE: 128947 | Hs.72550 | hyaluronan-mediated motility receptor (RHAMM) | HMMR | 0 | 0 |
| IMAGE: 471568 | Hs.109706 | hematological and neurological expressed 1 | HN1 | 0 | 0 |
| IMAGE: 795803 | Hs.109706 | hematological and neurological expressed 1 | HN1 | 1 | 0 |
| IMAGE: 489208 | Hs.172035 | HN1 like | HN1L | 0 | 2 |
| IMAGE: 855723 | Hs.172035 | HN1 like | HN1L | 1 | 2 |
| IMAGE: 327350 | Hs.232400 | heterogeneous nuclear ribonucleoprotein A2/B1 | HNRPA2B1 | 0 | 2 |
| IMAGE: 453790 | Hs.15265 | heterogeneous nuclear ribonucleoprotein R | HNRPR | 0 | 2 |
| IMAGE: 260696 | Hs.154762 | HIV-1 rev binding protein 2 | HRB2 | 0 | 2 |
| IMAGE: 755581 | Hs.258730 | heme-regulated initiation factor 2-alpha kinase | HRI | 0 | 2 |
| IMAGE: 825695 | Hs.279918 | hypothetical protein HSPC111 | HSPC111 | 0 | 2 |
| IMAGE: 796469 | Hs.5199 | HSPC150 protein similar to ubiquitin-conjugating enzyme | HSPC150 | 0 | 0 |
| IMAGE: 786690 | Hs.150555 | protein predicted by clone 23733 | HSU79274 | 0 | 2 |
| IMAGE: 221295 | Hs.180919 | inhibitor of DNA binding 2, dominant negative helix-loop-helix protein | ID2 | 0 | 2 |
| IMAGE: 756405 | Hs.76884 | inhibitor of DNA binding 3, dominant negative helix-loop-helix protein | ID3 | 0 | 2 |
| IMAGE: 44975 | Hs.76038 | isopentenyl-diphosphate delta isomerase | IDI1 | 0 | −2 |
| IMAGE: 588840 | Hs.20315 | interferon-induced protein with tetratricopeptide repeats 1 | IFIT1 | 0 | 0 |
| IMAGE: 809946 | Hs.315177 | interferon-related developmental regulator 2 | IFRD2 | 0 | 2 |
| IMAGE: 796996 | Hs.3631 | immunoglobulin (CD79A) binding protein 1 | IGBP1 | 0 | −2 |
| IMAGE: 138265 | Hs.82112 | interleukin 1 receptor, type I | IL1R1 | 1 | −2 |
| IMAGE: 146671 | Hs.82112 | interleukin 1 receptor, type I | IL1R1 | 0 | −2 |
| IMAGE: 2018581 | Hs.82065 | interleukin 6 signal transducer (gp130, oncostatin M receptor) | IL6ST | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 753743 | Hs.82065 | interleukin 6 signal transducer (gp130, oncostatin M receptor) | IL6ST | 1 | −2 |
| IMAGE: 840460 | Hs.362807 | interleukin 7 receptor | IL7R | 0 | 2 |
| IMAGE: 242952 | Hs.75117 | interleukin enhancer binding factor 2, 45 kDa | ILF2 | 0 | 0 |
| IMAGE: 814428 | Hs.91579 | U3 snoRNP protein 4 homolog | IMP4 | 0 | 2 |
| IMAGE: 207288 | Hs.56205 | insulin induced gene 1 | INSIG1 | 0 | −2 |
| IMAGE: 471835 | Hs.61790 | importin 4 | IPO4 | 0 | 2 |
| IMAGE: 73784 | Hs.227730 | integrin, alpha 6 | ITGA6 | 0 | 2 |
| IMAGE: 859478 | Hs.87149 | integrin, beta 3 (platelet glycoprotein IIIa, antigen CD61) | ITGB3 | 0 | 0 |
| IMAGE: 276091 | Hs.78877 | inositol 1,4,5-trisphosphate 3-kinase B | ITPKB | 0 | −2 |
| IMAGE: 141815 | Hs.91143 | jagged 1 (Alagille syndrome) | JAG1 | 0 | −2 |
| IMAGE: 2027560 | Hs.301613 | JTV1 gene | JTV1 | 0 | 2 |
| IMAGE: 1474284 | Hs.323949 | kangai 1 (suppression of tumorigenicity 6, prostate; CD82 antigen (R2 leukocyte antigen, antigen detected by monoclonal and antibody IA4)) | KAI1 | 0 | −2 |
| IMAGE: 298769 | Hs.285818 | similar to *Caenorhabditis elegans* protein C42C1.9 | KEO4 | 0 | 2 |
| IMAGE: 788721 | Hs.154797 | KIAA0090 protein | KIAA0090 | 0 | 2 |
| IMAGE: 51918 | Hs.155314 | KIAA0095 gene product | KIAA0095 | 0 | 2 |
| IMAGE: 342640 | Hs.81892 | KIAA0101 gene product | KIAA0101 | 0 | 0 |
| IMAGE: 41525 | Hs.7911 | KIAA0323 protein | KIAA0323 | 0 | −2 |
| IMAGE: 502067 | Hs.16950 | KIAA0342 gene product | KIAA0342 | 0 | −2 |
| IMAGE: 813828 | Hs.23311 | KIAA0367 protein | KIAA0367 | 0 | −2 |
| IMAGE: 768940 | Hs.27973 | KIAA0874 protein | KIAA0874 | 0 | −2 |
| IMAGE: 487013 | Hs.155182 | KIAA1036 protein | KIAA1036 | 0 | −2 |
| IMAGE: 305920 | Hs.6606 | hypothetical protein KIAA1109 | KIAA1109 | 0 | −2 |
| IMAGE: 502586 | Hs.306867 | KIAA1228 protein | KIAA1228 | 0 | −2 |
| IMAGE: 1581420 | Hs.152925 | KIAA1268 protein | KIAA1268 | 0 | −2 |
| IMAGE: 754581 | Hs.288348 | KIAA1305 protein | KIAA1305 | 0 | −2 |
| IMAGE: 1670954 | Hs.22941 | KIAA1363 protein | KIAA1363 | 0 | 2 |
| IMAGE: 200741 | Hs.22941 | KIAA1363 protein | KIAA1363 | 1 | 2 |
| IMAGE: 32887 | Hs.22941 | KIAA1363 protein | KIAA1363 | 1 | 2 |
| IMAGE: 1916769 | Hs.156667 | KIAA1536 protein | KIAA1536 | 0 | −2 |
| IMAGE: 462845 | Hs.156667 | KIAA1536 protein | KIAA1536 | 1 | −2 |
| IMAGE: 50276 | Hs.17767 | KIAA1554 protein | KIAA1554 | 0 | −2 |
| IMAGE: 877884 | Hs.298573 | KIAA1720 protein | KIAA1720 | 0 | 2 |
| IMAGE: 1859050 | Hs.172792 | KIAA1946 protein | KIAA1946 | 0 | −2 |
| IMAGE: 769942 | Hs.119324 | kinesin family member 22 | KIF22 | 0 | 0 |
| IMAGE: 788256 | Hs.270845 | kinesin family member 23 | KIF23 | 0 | 0 |
| IMAGE: 292933 | Hs.20830 | kinesin family member C1 | KIFC1 | 0 | 0 |
| IMAGE: 265060 | Hs.81665 | v-kit Hardy-Zuckerman 4 feline sarcoma viral oncogene homolog | KIT | 0 | −2 |
| IMAGE: 746080 | Hs.272239 | kelch-like 5 (*Drosphila*) | KLHL5 | 0 | −2 |
| IMAGE: 739230 | Hs.26002 | LIM domain binding 1 | LDB1 | 0 | −2 |
| IMAGE: 825295 | Hs.213289 | low density lipoprotein receptor (familial hypercholesterolemia) | LDLR | 0 | −2 |
| IMAGE: 854701 | Hs.85226 | lipase A, lysosomal acid, cholesterol esterase (Wolman disease) | LIPA | 0 | −2 |
| IMAGE: 1591599 | Hs.89497 | lamin B1 | LMNB1 | 0 | 0 |
| IMAGE: 815501 | Hs.76084 | lamin B2 | LMNB2 | 0 | 2 |
| IMAGE: 773308 | Hs.184164 | hypothetical protein BC014003 | LOC115106 | 0 | 2 |
| IMAGE: 429811 | Hs.60293 | similar to hypothetical protein FLJ10883 | LOC115294 | 0 | −2 |
| IMAGE: 827141 | Hs.180591 | mitotic phosphoprotein 44 | LOC129401 | 0 | 2 |
| IMAGE: 280763 | Hs.163725 | adult retina protein | LOC153222 | 0 | −2 |
| IMAGE: 757431 | Hs.163725 | adult retina protein | LOC153222 | 1 | −2 |
| IMAGE: 815297 | Hs.163725 | adult retina protein | LOC153222 | 1 | −2 |
| IMAGE: 1623191 | Hs.99480 | hypothetical protein LOC157570 | LOC157570 | 1 | 0 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 229560 | Hs.99480 | hypothetical protein LOC157570 | LOC157570 | 1 | 0 |
| IMAGE: 811069 | Hs.99480 | hypothetical protein LOC157570 | LOC157570 | 0 | 0 |
| IMAGE: 1502490 | Hs.94795 | hypothetical protein LOC169611 | LOC169611 | 0 | −2 |
| IMAGE: 196634 | Hs.5957 | hypothetical protein LOC201562 | LOC201562 | 0 | 2 |
| IMAGE: 746245 | Hs.5957 | hypothetical protein LOC201562 | LOC201562 | 1 | 2 |
| IMAGE: 295650 | Hs.342655 | hypothetical protein LOC201895 | LOC201895 | 0 | −2 |
| IMAGE: 1895046 | Hs.150011 | hypothetical protein LOC221810 | LOC221810 | 0 | −2 |
| IMAGE: 823815 | Hs.432790 | hypothetical protein LOC253263 | LOC253263 | 0 | −2 |
| IMAGE: 264502 | Hs.20575 | hypothetical protein LOC283431 | LOC283431 | 0 | 0 |
| IMAGE: 130895 | Hs.90790 | hypothetical protein LOC284018 | LOC284018 | 0 | −2 |
| IMAGE: 283124 | Hs.17567 | hypothetical protein LOC284436 | LOC284436 | 0 | −2 |
| IMAGE: 665445 | Hs.350475 | hypothetical protein LOC285362 | LOC285362 | 0 | −2 |
| IMAGE: 530237 | Hs.4094 | hypothetical protein LOC339924 | LOC339924 | 0 | −2 |
| IMAGE: 308466 | Hs.279582 | GTP-binding protein Sara | LOC51128 | 0 | 2 |
| IMAGE: 771142 | Hs.98571 | complement C1r-like proteinase | LOC51279 | 0 | −2 |
| IMAGE: 1600239 | Hs.433180 | HSPC037 protein | LOC51659 | 0 | 0 |
| IMAGE: 772925 | Hs.46967 | HSPCO34 protein | LOC51668 | 0 | 2 |
| IMAGE: 274512 | Hs.22350 | hypothetical protein LOC56757 | LOC56757 | 0 | −2 |
| IMAGE: 61626 | Hs.193384 | putatative 28 kDa protein | LOC56902 | 0 | 2 |
| IMAGE: 756554 | Hs.24983 | hypothetical protein from EUROIMAGE 2021883 | LOC56926 | 0 | 2 |
| IMAGE: 418240 | Hs.28893 | hypothetical protein LOC90110 | LOC90110 | 0 | 0 |
| IMAGE: 2316683 | Hs.13413 | hypothetical protein BC015148 | LOC93081 | 0 | 2 |
| IMAGE: 882506 | Hs.83354 | lysyl oxidase-like 2 | LOXL2 | 0 | 2 |
| IMAGE: 783698 | Hs.81412 | lipin 1 | LPIN1 | 0 | −2 |
| IMAGE: 461144 | Hs.24279 | leucine-rich repeats and immunoglobulin-like domains 2 | LRIG2 | 0 | −2 |
| IMAGE: 810551 | Hs.446467 | low density lipoprotein-related protein 1 (alpha-2-macroglobulin receptor) | LRP1 | 0 | −2 |
| IMAGE: 796176 | Hs.111632 | LSM3 homolog, U6 small nuclear RNA associated (S. cerevisiae) | LSM3 | 0 | 2 |
| IMAGE: 50175 | Hs.76719 | LSM4 homolog, U6 small nuclear RNA associated (S. cerevisiae) | LSM4 | 0 | 2 |
| IMAGE: 462806 | Hs.93199 | lanosterol synthase (2,3-oxidosqualene-lanosterol cyclase) | LSS | 1 | −2 |
| IMAGE: 770355 | Hs.93199 | lanosterol synthase (2,3-oxidosqualene-lanosterol cyclase) | LSS | 0 | −2 |
| IMAGE: 471855 | Hs.79914 | lumican | LUM | 0 | −2 |
| IMAGE: 366009 | Hs.425427 | hypothetical protein FLJ20425 | LYAR | 0 | 2 |
| IMAGE: 767163 | Hs.425427 | hypothetical protein FLJ20425 | LYAR | 1 | 0 |
| IMAGE: 814701 | Hs.79078 | MAD2 mitotic arrest deficient-like 1 (yeast) | MAD2L1 | 0 | 0 |
| IMAGE: 277414 | Hs.30250 | v-maf musculoaponeurotic fibrosarcoma oncogene homolog (avian) | MAF | 0 | −2 |
| IMAGE: 487793 | Hs.30250 | v-maf musculoaponeurotic fibrosarcoma oncogene homolog (avian) | MAF | 1 | −2 |
| IMAGE: 823688 | Hs.25253 | mannosidase, alpha, class 1A, member 1 | MAN1A1 | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 340630 | Hs.248 | mitogen-activated protein kinase kinase kinase 8 | MAP3K8 | 0 | 2 |
| IMAGE: 590774 | Hs.178695 | mitogen-activated protein kinase 13 | MAPK13 | 0 | 0 |
| IMAGE: 428223 | Hs.234279 | microtubule-associated protein, RP/EB family, member 1 | MAPRE1 | 0 | 2 |
| IMAGE: 328889 | Hs.69547 | myelin basic protein | MBP | 0 | −2 |
| IMAGE: 809557 | Hs.179565 | MCM3 minichromosome maintenance deficient 3 (*S. cerevisiae*) | MCM3 | 0 | 2 |
| IMAGE: 843049 | Hs.154443 | MCM4 minichromosome maintenance deficient 4 (*S. cerevisiae*) | MCM4 | 0 | 0 |
| IMAGE: 531402 | Hs.77171 | MCM5 minichromosome maintenance deficient 5, cell division cycle 46 (*S. cerevisiae*) | MCM5 | 0 | 0 |
| IMAGE: 700721 | Hs.77171 | MCM5 minichromosome maintenance deficient 5, cell division cycle 46 (*S. cerevisiae*) | MCM5 | 1 | 0 |
| IMAGE: 1587847 | Hs.155462 | MCM6 minichromosome maintenance deficient 6 (MIS5 homolog, (*S. pombe*) (*S. cerevisiae*) | MCM6 | 0 | 0 |
| IMAGE: 2325609 | Hs.77152 | MCM7 minichromosome maintenance deficient 7 (*S. cerevisiae*) | MCM7 | 0 | 2 |
| IMAGE: 796994 | Hs.83532 | membrane cofactor protein (CD46, trophoblast-lymphocyte cross-reactive antigen) | MCP | 0 | −2 |
| IMAGE: 142586 | Hs.102696 | MCT-1 protein | MCT-1 | 0 | 2 |
| IMAGE: 448232 | Hs.77955 | MADS box transcription enhancer factor 2, polypeptide D (myocyte enhancer factor 2D) | MEF2D | 0 | −2 |
| IMAGE: 1517595 | Hs.184339 | maternal embryonic leucine zipper kinase | MELK | 0 | 0 |
| IMAGE: 79655 | Hs.11039 | MEP50 protein | MEP50 | 0 | 2 |
| IMAGE: 626841 | Hs.316752 | met proto-oncogene (hepatocyte growth factor receptor) | MET | 0 | 2 |
| IMAGE: 754509 | Hs.316752 | met proto-oncogene (hepatocyte growth factor receptor) | MET | 1 | 0 |
| IMAGE: 488017 | Hs.3745 | milk fat globule-EGF factor 8 protein | MFGE8 | 0 | −2 |
| IMAGE: 564981 | Hs.134726 | hypothetical protein MGC: 10200 | MGC10200 | 0 | 2 |
| IMAGE: 356835 | Hs.271599 | hypothetical protein MGC10500 | MGC10500 | 0 | −2 |
| IMAGE: 743362 | Hs.111099 | hypothetical protein MGC10974 | MGC10974 | 0 | 2 |
| IMAGE: 1642496 | Hs.293943 | hypothetical protein MGC11266 | MGC11266 | 0 | 2 |
| IMAGE: 758314 | Hs.97031 | hypothetical protein MGC13047 | MGC13047 | 0 | −2 |
| IMAGE: 769945 | Hs.256301 | MGC13170 gene | MGC13170 | 0 | 2 |
| IMAGE: 813675 | Hs.37616 | hypothetical protein MGC14480 | MGC14480 | 0 | 2 |
| IMAGE: 448344 | Hs.79 | hypothetical protein MGC15429 | MGC15429 | 0 | −2 |
| IMAGE: 296155 | Hs.23044 | similar to RIKEN cDNA 2610036L13 | MGC16386 | 0 | 0 |
| IMAGE: 769796 | Hs.26670 | HGFL gene | MGC17330 | 0 | −2 |
| IMAGE: 51320 | Hs.301394 | hypothetical protein MGC3101 | MGC3101 | 0 | 2 |
| IMAGE: 502096 | Hs.21415 | hypothetical protein MGC39820 | MGC39820 | 0 | −2 |
| IMAGE: 271855 | Hs.7041 | MGC4170 protein | MGC4170 | 0 | −2 |
| IMAGE: 754588 | Hs.39504 | hypothetical protein MGC4308 | MGC4308 | 0 | 2 |
| IMAGE: 1858892 | Hs.40065 | hypothetical protein MGC4825 | MGC4825 | 0 | 2 |
| IMAGE: 742642 | Hs.11169 | Gene 33/Mig-6 | MIG-6 | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 140957 | Hs.46743 | McKusick-Kaufman syndrome | MKKS | 1 | 2 |
| IMAGE: 729957 | Hs.46743 | McKusick-Kaufman syndrome | MKKS | 0 | 2 |
| IMAGE: 461770 | Hs.349196 | myeloid/lymphoid or mixed-lineage leukemia (trithorax homolog, Drosphila); translocated to, 6 | MLLT6 | 0 | 0 |
| IMAGE: 810791 | Hs.433410 | menage a trois 1 (CAK assembly factor) | MNAT1 | 0 | 2 |
| IMAGE: 292964 | Hs.240 | M-phase phosphoprotein 1 | MPHOSPH1 | 0 | 0 |
| IMAGE: 713236 | Hs.240 | M-phase phosphoprotein 1 | MPHOSPH1 | 1 | 0 |
| IMAGE: 595637 | Hs.12702 | modulator recognition factor 2 | MRF2 | 0 | −2 |
| IMAGE: 1636069 | Hs.109059 | mitochondrial ribosomal protein L12 | MRPL12 | 0 | 2 |
| IMAGE: 843263 | Hs.4209 | mitochondrial ribosomal protein L37 | MRPL37 | 0 | 2 |
| IMAGE: 755304 | Hs.180312 | mitochondrial ribosomal protein S16 | MRPS16 | 0 | 2 |
| IMAGE: 773483 | Hs.55097 | mitochondrial ribosomal protein S28 | MRPS28 | 0 | 2 |
| IMAGE: 131362 | Hs.170328 | moesin | MSN | 1 | 2 |
| IMAGE: 81332 | Hs.170328 | moesin | MSN | 0 | 2 |
| IMAGE: 78353 | Hs.381097 | metallothionein 1F (functional) | MT1F | 0 | 2 |
| IMAGE: 2019011 | Hs.73133 | metallothionein 3 (growth inhibitory factor (neurotrophic)) | MT3 | 0 | 2 |
| IMAGE: 203008 | Hs.144407 | likely ortholog of mouse MutT homolog 2 | MTH2 | 0 | 2 |
| IMAGE: 2028294 | Hs.172665 | methylenetetrahydrofolate dehydrogenase (NADP+ dependent), methyltetrahydrofolate cyclohydrolase, formyltetrahydrofolate synthetase | MTHFD1 | 0 | 2 |
| IMAGE: 280934 | Hs.3828 | mevalonate (diphospho) decarboxylase | MVD | 0 | −2 |
| IMAGE: 1680549 | Hs.118630 | MAX interacting protein 1 | MXI1 | 1 | −2 |
| IMAGE: 271478 | Hs.118630 | MAX interacting protein 1 | MXI1 | 1 | −2 |
| IMAGE: 277611 | Hs.118630 | MAX interacting protein 1 | MXI1 | 1 | −2 |
| IMAGE: 489947 | Hs.118630 | MAX interacting protein 1 | MXI1 | 1 | −2 |
| IMAGE: 609366 | Hs.118630 | MAX interacting protein 1 | MXI1 | 0 | −2 |
| IMAGE: 1526789 | Hs.300592 | v-myb myeloblastosis viral oncogene homolog (avian)-like 1 | MYBL1 | 0 | 2 |
| IMAGE: 815526 | Hs.179718 | v-myb myeloblastosis viral oncogene homolog (avian)-like 2 | MYBL2 | 0 | 2 |
| IMAGE: 510794 | Hs.78221 | c-myc binding protein | MYCBP | 0 | 2 |
| IMAGE: 842989 | Hs.77385 | myosin, light polypeptide 6, alkali, smooth muscle and non-muscle | MYL6 | 0 | 2 |
| IMAGE: 1474424 | Hs.69476 | similar to RIKEN cDNA 1110001A07 | na | 0 | 2 |
| IMAGE: 1468466 | Hs.127797 | similar to PRO2550 | na | 0 | 0 |
| IMAGE: 1881517 | Hs.283127 | similar to Diap3 protein | na | 0 | 0 |
| IMAGE: 25058 | Hs.179397 | hypothetical gene supported by AF131741 | na | 0 | 0 |
| IMAGE: 469898 | Hs.40527 | LOC345469 | na | 0 | 0 |
| IMAGE: 1553567 | Hs.260395 | similar to hypothetical protein | na | 0 | −2 |
| IMAGE: 1758226 | Hs.144814 | similar to caspase 1 isoform alpha precursor; interleukin 1-beta convertase; interleukin 1-B converting enzyme; IL1B-convertase | na | 0 | −2 |
| IMAGE: 346860 | Hs.177781 | hypothetical gene supported by AK093984 | na | 1 | −2 |
| IMAGE: 78148 | Hs.177781 | hypothetical gene supported by AK093984 | na | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 788445 | Hs.237642 | similar to family 4 cytochrome P450; cytochrome P450, 4v3 | na | 0 | −2 |
| IMAGE: 825356 | Hs.432755 | similar to SNAG1 | na | 0 | −2 |
| IMAGE: 840708 | Hs.177781 | hypothetical gene supported by AK093984 | na | 1 | −2 |
| IMAGE: 246808 | Hs.6844 | neuronal apoptosis inhibitor protein 2 | NALP2 | 0 | 0 |
| IMAGE: 502333 | Hs.225977 | nuclear receptor coactivator 3 | NCOA3 | 0 | −2 |
| IMAGE: 73531 | Hs.9908 | nitrogen fixation cluster-like | NIFU | 0 | −2 |
| IMAGE: 812088 | Hs.22151 | neurolysin (metallopeptidase M3 family) | NLN | 0 | 2 |
| IMAGE: 845363 | Hs.118638 | non-metastatic cells 1, protein (NM23A) expressed in | NME1 | 0 | 2 |
| IMAGE: 811097 | Hs.23990 | nucleolar protein family A, member 2 (H/ACA small nucleolar RNPs) | NOLA2 | 0 | 2 |
| IMAGE: 756502 | Hs.388 | nudix (nucleoside diphosphate linked moiety X)-type motif 1 | NUDT1 | 0 | 2 |
| IMAGE: 257955 | Hs.236204 | nuclear pore complex protein | NUP107 | 1 | 2 |
| IMAGE: 827159 | Hs.236204 | nuclear pore complex protein | NUP107 | 0 | 2 |
| IMAGE: 413299 | Hs.90421 | nucleoporin like 1 | NUPL1 | 0 | 2 |
| IMAGE: 1899230 | Hs.151734 | nuclear transport factor 2 | NUTF2 | 0 | 2 |
| IMAGE: 512116 | Hs.377830 | O-acyltransferase (membrane bound) domain containing 1 | OACT1 | 0 | 0 |
| IMAGE: 282720 | Hs.274170 | Opa-interacting protein 2 | OIP2 | 0 | 2 |
| IMAGE: 191603 | Hs.179661 | beta 5-tubulin | OK/SW-cl.56 | 0 | 0 |
| IMAGE: 773479 | Hs.179661 | beta 5-tubulin | OK/SW-cl.56 | 1 | 0 |
| IMAGE: 268978 | Hs.109694 | oxysterol binding protein-like 8 | OSBPL8 | 0 | −2 |
| IMAGE: 80484 | Hs.424279 | p8 protein (candidate of metastasis 1) | P8 | 0 | −2 |
| IMAGE: 813584 | Hs.14125 | p53 regulated PA26 nuclear protein | PA26 | 0 | −2 |
| IMAGE: 842973 | Hs.343258 | proliferation-associated 2G4, 38 kDa | PA2G4 | 0 | 2 |
| IMAGE: 273546 | Hs.117950 | phosphoribosylaminoimidazole carboxylase, phosphoribosylaminoimidazole succinocarboxamide synthetase | PAICS | 0 | 2 |
| IMAGE: 366042 | Hs.8068 | pre-B-cell leukemia transcription factor interacting protein 1 | PBXIP1 | 0 | −2 |
| IMAGE: 43229 | Hs.78996 | proliferating cell nuclear antigen | PCNA | 1 | 0 |
| IMAGE: 789182 | Hs.78996 | proliferating cell nuclear antigen | PCNA | 0 | 0 |
| IMAGE: 243155 | Hs.184352 | pericentrin 1 | PCNT1 | 0 | 2 |
| IMAGE: 813460 | Hs.432969 | proprotein convertase subtilisin/kexin type 7 | PCSK7 | 0 | 2 |
| IMAGE: 824426 | Hs.278426 | PDGFA associated protein 1 | PDAP1 | 0 | 2 |
| IMAGE: 49860 | Hs.92261 | pyruvate dehydrogenase kinase, isoenzyme 2 | PDK2 | 0 | −2 |
| IMAGE: 950682 | Hs.99910 | phosphofructokinase, platelet | PFKP | 0 | 2 |
| IMAGE: 826173 | Hs.408943 | profilin 1 | PFN1 | 0 | 2 |
| IMAGE: 796263 | Hs.197335 | plasma glutamate carboxypeptidase | PGCP | 0 | −2 |
| IMAGE: 1533669 | Hs.126706 | 1-aminocyclopropane-1-carboxylate synthase | PHACS | 0 | −2 |
| IMAGE: 30114 | Hs.128653 | putative homeodomain transcription factor 2 | PHTF2 | 0 | 0 |
| IMAGE: 1839367 | Hs.24596 | RAD51-interacting protein | PIR51 | 0 | 0 |
| IMAGE: 364436 | Hs.333212 | phosphatidylinositol transfer protein, cytoplasmic 1 | PITPNC1 | 0 | 2 |
| IMAGE: 855557 | Hs.3407 | protein kinase (cAMP-dependent, catalytic) inhibitor gamma | PKIG | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 320355 | Hs.171945 | phospholipase A2 receptor 1, 180 kDa | PLA2R1 | 1 | −2 |
| IMAGE: 511303 | Hs.171945 | phospholipase A2 receptor 1, 180 kDa | PLA2R1 | 0 | −2 |
| IMAGE: 590154 | Hs.179657 | plasminogen activator, urokinase receptor | PLAUR | 0 | 2 |
| IMAGE: 810017 | Hs.179657 | plasminogen activator, urokinase receptor | PLAUR | 1 | 2 |
| IMAGE: 159455 | Hs.74573 | phospholipase D3 | PLD3 | 0 | −2 |
| IMAGE: 195040 | Hs.75576 | plasminogen | PLG | 0 | 2 |
| IMAGE: 744047 | Hs.77597 | polo-like kinase (*Drosphila*) | PLK | 0 | 0 |
| IMAGE: 263013 | Hs.41270 | procollagen-lysine, 2-oxoglutarate 5-dioxygenase (lysine hydroxylase) 2 | PLOD2 | 0 | 2 |
| IMAGE: 838829 | Hs.143323 | putative DNA/chromatin binding motif | PLU-1 | 1 | 0 |
| IMAGE: 2108411 | Hs.143323 | putative DNA/chromatin binding motif | PLU-1 | 0 | −2 |
| IMAGE: 755952 | Hs.278311 | plexin B1 | PLXNB1 | 0 | −2 |
| IMAGE: 341051 | Hs.44499 | pinin, desmosome associated protein | PNN | 0 | 2 |
| IMAGE: 786078 | Hs.99185 | polymerase (DNA directed), epsilon 2 (p59 subunit) | POLE2 | 0 | 2 |
| IMAGE: 511632 | Hs.110857 | polymerase (RNA) III (DNA directed) polypeptide K, 12.3 kDa | POLR3K | 0 | 2 |
| IMAGE: 82556 | Hs.167246 | P450 (cytochrome) oxidoreductase | POR | 0 | −2 |
| IMAGE: 767277 | Hs.9880 | peptidyl prolyl isomerase H (cyclophilin H) | PPIH | 0 | 2 |
| IMAGE: 365641 | Hs.82741 | primase, polypeptide 1, 49 kDa | PRIM1 | 0 | 0 |
| IMAGE: 42325 | Hs.74519 | primase, polypeptide 2A, 58 kDa | PRIM2A | 0 | 0 |
| IMAGE: 770880 | Hs.74519 | primase, polypeptide 2A, 58 kDa | PRIM2A | 1 | 0 |
| IMAGE: 204483 | Hs.222088 | PRO2000 protein | PRO2000 | 0 | 0 |
| IMAGE: 280375 | Hs.222088 | PRO2000 protein | PRO2000 | 1 | 0 |
| IMAGE: 857002 | Hs.75969 | proline rich 2 | PROL2 | 0 | −2 |
| IMAGE: 2054635 | Hs.233952 | proteasome (prosome, macropain) subunit, alpha type, 7 | PSMA7 | 0 | 2 |
| IMAGE: 1602493 | Hs.250758 | proteasome (prosome, macropain) 26S subunit, ATPase, 3 | PSMC3 | 1 | 2 |
| IMAGE: 712916 | Hs.250758 | proteasome (prosome, macropain) 26S subunit, ATPase, 3 | PSMC3 | 0 | 2 |
| IMAGE: 823598 | Hs.4295 | proteasome (prosome, macropain) 26S subunit, non-ATPase, 12 | PSMD12 | 0 | 2 |
| IMAGE: 285686 | Hs.178761 | proteasome (prosome, macropain) 26S subunit, non-ATPase, 14 | PSMD14 | 0 | 2 |
| IMAGE: 809992 | Hs.74619 | proteasome (prosome, macropain) 26S subunit, non-ATPase, 2 | PSMD2 | 0 | 2 |
| IMAGE: 744800 | Hs.19718 | protein tyrosine phosphatase, receptor type, U | PTPRU | 0 | −2 |
| IMAGE: 1160558 | Hs.415877 | 6-pyruvoyltetrahydropterin synthase | PTS | 0 | 2 |
| IMAGE: 2018976 | Hs.252587 | pituitary tumor-transforming 1 | PTTG1 | 0 | 0 |
| IMAGE: 781089 | Hs.252587 | pituitary tumor-transforming 1 | PTTG1 | 1 | 0 |
| IMAGE: 843069 | Hs.172589 | nuclear phosphoprotein similar to *S. cerevisiae* PWP1 | PWP1 | 0 | 0 |
| IMAGE: 40120 | Hs.173656 | KIAA0941 protein | Rab11-FIP2 | 0 | −2 |
| IMAGE: 1619759 | Hs.183800 | Ran GTPase activating protein 1 | RANGAP1 | 0 | 0 |
| IMAGE: 324225 | Hs.17466 | retinoic acid receptor responder (tazarotene induced) 3 | RARRES3 | 0 | −2 |
| IMAGE: 731136 | Hs.11170 | RNA binding motif protein 14 | RBM14 | 0 | 2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 611028 | Hs.180378 | RNA binding motif protein, X chromosome | RBMX | 0 | 2 |
| IMAGE: 951080 | Hs.31442 | RecQ protein-like 4 | RECQL4 | 0 | 0 |
| IMAGE: 1574649 | Hs.115521 | REV3-like, catalytic subunit of DNA polymerase zeta (yeast) | REV3L | 0 | −2 |
| IMAGE: 860000 | Hs.139226 | replication factor C (activator 1) 2, 40 kDa | RFC2 | 0 | 0 |
| IMAGE: 277112 | Hs.115474 | replication factor C (activator 1) 3, 38 kDa | RFC3 | 0 | 2 |
| IMAGE: 309288 | Hs.35120 | replication factor C (activator 1) 4, 37 kDa | RFC4 | 0 | 0 |
| IMAGE: 512410 | Hs.25292 | ribonuclease H2, large subunit | RNASEH2A | 0 | 2 |
| IMAGE: 855243 | Hs.115823 | ribonuclease P1 | RNASEP1 | 0 | 2 |
| IMAGE: 786625 | Hs.180403 | ring finger protein 138 | RNF138 | 0 | 2 |
| IMAGE: 1900149 | Hs.153639 | ring finger protein 41 | RNF41 | 0 | 2 |
| IMAGE: 502690 | Hs.2280 | ribophorin I | RPN1 | 0 | 2 |
| IMAGE: 856489 | Hs.2934 | ribonucleotide reductase M1 polypeptide | RRM1 | 0 | 0 |
| IMAGE: 624627 | Hs.75319 | ribonucleotide reductase M2 polypeptide | RRM2 | 0 | 0 |
| IMAGE: 768466 | Hs.94262 | ribonucleotide reductase M2 B (TP53 inducible) | RRM2B | 0 | −2 |
| IMAGE: 827011 | Hs.272822 | RuvB-like 1 (*E. coli*) | RUVBL1 | 0 | 2 |
| IMAGE: 364510 | Hs.74592 | special AT-rich sequence binding protein 1 (binds to nuclear matrix/scaffold-associating DNA's) | SATB1 | 0 | −2 |
| IMAGE: 200012 | Hs.110783 | HBV pre-s2 binding protein 1 | SBP1 | 0 | −2 |
| IMAGE: 590759 | Hs.239926 | sterol-C4-methyl oxidase-like | SC4MOL | 0 | −2 |
| IMAGE: 123474 | Hs.119597 | stearoyl-CoA desaturase (delta-9-desaturase) | SCD | 0 | −2 |
| IMAGE: 1616241 | Hs.119597 | stearoyl-CoA desaturase (delta-9-desaturase) | SCD | 1 | −2 |
| IMAGE: 810711 | Hs.119597 | stearoyl-CoA desaturase (delta-9-desaturase) | SCD | 1 | −2 |
| IMAGE: 1635538 | Hs.82109 | syndecan 1 | SDC1 | 0 | 2 |
| IMAGE: 525926 | Hs.82109 | syndecan 1 | SDC1 | 1 | 0 |
| IMAGE: 586731 | Hs.389371 | stromal cell derived factor receptor 1 | SDFR1 | 0 | 2 |
| IMAGE: 167205 | Hs.334841 | selenium binding protein 1 | SELENBP1 | 0 | −2 |
| IMAGE: 754550 | Hs.177635 | likely ortholog of mouse semaF cytoplasmic domain associated protein 3 | SEMACAP3 | 0 | −2 |
| IMAGE: 381066 | Hs.151242 | serine (or cysteine) proteinase inhibitor, clade G (C1 inhibitor), member 1, (angioedema, hereditary) | SERPING1 | 0 | −2 |
| IMAGE: 788232 | Hs.8026 | sestrin 2 | SES2 | 0 | −2 |
| IMAGE: 47681 | Hs.30035 | splicing factor, arginine/serine-rich 10 (transformer 2 homolog, *Drosphila*) | SFRS10 | 0 | 2 |
| IMAGE: 809535 | Hs.73965 | splicing factor, arginine/serine-rich 2 | SFRS2 | 0 | 2 |
| IMAGE: 1584551 | Hs.76305 | surfactant, pulmonary-associated protein B | SFTPB | 0 | −2 |
| IMAGE: 486175 | Hs.75231 | solute carrier family 16 (monocarboxylic acid transporters), member 1 | SLC16A1 | 0 | 2 |
| IMAGE: 772304 | Hs.79172 | solute carrier family 25 (mitochondrial carrier; adenine nucleotide translocator), member 5 | SLC25A5 | 0 | 2 |
| IMAGE: 461098 | Hs.214646 | solute carrier family 35, member E2 | SLC35E2 | 0 | −2 |
| IMAGE: 71863 | Hs.5944 | solute carrier family 40 (iron-regulated transporter), member 1 | SLC40A1 | 0 | −2 |
| IMAGE: 839882 | Hs.324787 | solute carrier family 5 (inositol transporters), member 3 | SLC5A3 | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 378813 | Hs.251754 | secretory leukocyte protease inhibitor (antileukoproteinase) | SLPI | 0 | −2 |
| IMAGE: 682846 | Hs.119023 | SMC2 structural maintenance of chromosomes 2-like 1 (yeast) | SMC2L1 | 0 | 2 |
| IMAGE: 786504 | Hs.50758 | SMC4 structural maintenance of chromosomes 4-like 1 (yeast) | SMC4L1 | 0 | 0 |
| IMAGE: 565235 | Hs.89718 | spermine synthase | SMS | 0 | 2 |
| IMAGE: 754026 | Hs.194477 | E3 ubiquitin ligase SMURF2 | SMURF2 | 0 | 2 |
| IMAGE: 206370 | Hs.174051 | small nuclear ribonucleoprotein 70 kDa polypeptide (RNP antigen) | SNRP70 | 0 | −2 |
| IMAGE: 2322223 | Hs.173255 | small nuclear ribonucleoprotein polypeptide A | SNRPA | 0 | 2 |
| IMAGE: 490772 | Hs.80506 | small nuclear ribonucleoprotein polypeptide A' | SNRPA1 | 0 | 2 |
| IMAGE: 950482 | Hs.83753 | small nuclear ribonucleoprotein polypeptides B and B1 | SNRPB | 0 | 2 |
| IMAGE: 724387 | Hs.1063 | small nuclear ribonucleoprotein polypeptide C | SNRPC | 0 | 2 |
| IMAGE: 47542 | Hs.86948 | small nuclear ribonucleoprotein D1 polypeptide 16 kDa | SNRPD1 | 0 | 2 |
| IMAGE: 431803 | Hs.334612 | small nuclear ribonucleoprotein polypeptide E | SNRPE | 0 | 2 |
| IMAGE: 2307015 | Hs.16244 | sperm associated antigen 5 | SPAG5 | 0 | 0 |
| IMAGE: 124781 | Hs.71465 | squalene epoxidase | SQLE | 0 | −2 |
| IMAGE: 322643 | Hs.8185 | sulfide quinone reductase-like (yeast) | SQRDL | 1 | −2 |
| IMAGE: 85060 | Hs.8185 | sulfide quinone reductase-like (yeast) | SQRDL | 0 | −2 |
| IMAGE: 856796 | Hs.76244 | spermidine synthase | SRM | 0 | 2 |
| IMAGE: 292082 | Hs.28707 | signal sequence receptor, gamma (translocon-associated protein gamma) | SSR3 | 0 | 2 |
| IMAGE: 767206 | Hs.28707 | signal sequence receptor, gamma (translocon-associated protein gamma) | SSR3 | 1 | 2 |
| IMAGE: 813499 | Hs.25723 | Sjogren's syndrome/scleroderma autoantigen 1 | SSSCA1 | 0 | 2 |
| IMAGE: 149934 | Hs.9075 | serine/threonine kinase 17a (apoptosis-inducing) | STK17A | 0 | 2 |
| IMAGE: 2106955 | Hs.172052 | serine/threonine kinase 18 | STK18 | 0 | 2 |
| IMAGE: 129865 | Hs.250822 | serine/threonine kinase 6 | STK6 | 0 | 0 |
| IMAGE: 754018 | Hs.154567 | supervillin | SVIL | 0 | −2 |
| IMAGE: 705064 | Hs.104019 | transforming, acidic coiled-coil containing protein 3 | TACC3 | 0 | 0 |
| IMAGE: 359457 | Hs.433399 | transgelin | TAGLN | 0 | 2 |
| IMAGE: 33122 | Hs.443668 | likely ortholog of mouse transforming growth factor beta regulated gene 1 | TBRG1 | 0 | −2 |
| IMAGE: 347373 | Hs.184693 | transcription elongation factor B (SIII), polypeptide 1 (15 kDa, elongin C) | TCEB1 | 0 | 2 |
| IMAGE: 1631194 | Hs.266940 | t-complex-associated-testis-expressed 1-like 1 | TCTEL1 | 0 | 2 |
| IMAGE: 266696 | Hs.266940 | t-complex-associated-testis-expressed 1-like 1 | TCTEL1 | 1 | 2 |
| IMAGE: 726086 | Hs.378774 | tissue factor pathway inhibitor 2 | TFPI2 | 0 | 2 |
| IMAGE: 502542 | Hs.355819 | homolog of yeast Tim50 | TIM50L | 0 | 2 |
| IMAGE: 240766 | Hs.5831 | tissue inhibitor of metalloproteinase 1 | TIMP1 | 0 | 0 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 1534435 | Hs.6441 | tissue inhibitor of metalloproteinase 2 (erythroid potentiating activity, collagenase inhibitor) | TIMP2 | 0 | −2 |
| IMAGE: 810444 | Hs.101382 | tumor necrosis factor, alpha-induced protein 2 | TNFAIP2 | 0 | −2 |
| IMAGE: 135791 | Hs.355899 | tumor necrosis factor receptor superfamily, member 12A | TNFRSF12A | 1 | 2 |
| IMAGE: 1759582 | Hs.355899 | tumor necrosis factor receptor superfamily, member 12A | TNFRSF12A | 0 | 2 |
| IMAGE: 271670 | Hs.26401 | tumor necrosis factor (ligand) superfamily, member 12 | TNFSF12 | 0 | −2 |
| IMAGE: 75644 | Hs.169886 | tenascin XB | TNXB | 0 | −2 |
| IMAGE: 809466 | Hs.30928 | translocase of outer mitochondrial membrane 40 homolog (yeast) | TOMM40 | 0 | 2 |
| IMAGE: 825470 | Hs.156346 | topoisomerase (DNA) II alpha 170 kDa | TOP2A | 0 | 0 |
| IMAGE: 1629113 | Hs.104741 | T-LAK cell-originated protein kinase | TOPK | 0 | 0 |
| IMAGE: 785368 | Hs.104741 | T-LAK cell-originated protein kinase | TOPK | 1 | 0 |
| IMAGE: 814528 | Hs.75497 | tumor protein p53 inducible nuclear protein 1 | TP53INP1 | 0 | −2 |
| IMAGE: 855749 | Hs.83848 | triosephosphate isomerase 1 | TPI1 | 0 | 2 |
| IMAGE: 488479 | Hs.77899 | tropomyosin 1 (alpha) | TPM1 | 0 | 2 |
| IMAGE: 740620 | Hs.300772 | tropomyosin 2 (beta) | TPM2 | 0 | 2 |
| IMAGE: 549146 | Hs.318501 | tripartite motif-containing 22 | TRIM22 | 0 | −2 |
| IMAGE: 856427 | Hs.6566 | thyroid hormone receptor interactor 13 | TRIP13 | 0 | 0 |
| IMAGE: 1897944 | Hs.114360 | transforming growth factor beta-stimulated protein TSC-22 | TSC22 | 0 | −2 |
| IMAGE: 795936 | Hs.75066 | translin | TSN | 0 | 0 |
| IMAGE: 612274 | Hs.75318 | tubulin, alpha 1 (testis specific) | TUBA1 | 0 | 2 |
| IMAGE: 38816 | Hs.75318 | tubulin, alpha 1 (testis specific) | TUBA1 | 1 | 0 |
| IMAGE: 2307420 | Hs.458114 | tubulin, beta polypeptide | TUBB | 0 | 0 |
| IMAGE: 1636876 | Hs.251653 | tubulin, beta, 2 | TUBB2 | 0 | 0 |
| IMAGE: 108377 | Hs.21635 | tubulin, gamma 1 | TUBG1 | 0 | 2 |
| IMAGE: 50743 | Hs.42644 | thioredoxin-like 2 | TXNL2 | 0 | 2 |
| IMAGE: 853368 | Hs.29475 | thymidylate synthetase | TYMS | 0 | 0 |
| IMAGE: 292515 | Hs.21293 | UDP-N-acetylglucosamine pyrophosphorylase 1 | UAP1 | 1 | 2 |
| IMAGE: 486035 | Hs.21293 | UDP-N-acetylglucosamine pyrophosphorylase 1 | UAP1 | 0 | 2 |
| IMAGE: 146882 | Hs.93002 | ubiquitin-conjugating enzyme E2C | UBE2C | 0 | 0 |
| IMAGE: 769921 | Hs.93002 | ubiquitin-conjugating enzyme E2C | UBE2C | 1 | 0 |
| IMAGE: 279972 | Hs.184325 | ubiquitin-conjugating enzyme E2, J1 (UBC6 homolog, yeast) | UBE2J1 | 0 | 2 |
| 1292535 | Hs.288549 | ubiquitin UBF-fl | UBF-fl | 0 | 0 |
| IMAGE: 1550739 | Hs.108106 | ubiquitin-like, containing PHD and RING finger domains, 1 | UHRF1 | 0 | 0 |
| IMAGE: 344243 | Hs.454562 | uridine monophosphate kinase | UMPK | 0 | 2 |
| IMAGE: 760344 | Hs.2057 | uridine monophosphate synthetase (orotate phosphoribosyl transferase and orotidine-5'-decarboxylase) | UMPS | 0 | 2 |
| IMAGE: 489595 | Hs.35086 | ubiquitin specific protease 1 | USP1 | 0 | 0 |
| IMAGE: 73596 | Hs.35086 | ubiquitin specific protease 1 | USP1 | 1 | 0 |
| IMAGE: 813261 | Hs.6651 | vesicle-associated membrane protein 4 | VAMP4 | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 486221 | Hs.149155 | voltage-dependent anion channel 1 | VDAC1 | 0 | 2 |
| IMAGE: 755145 | Hs.155191 | villin 2 (ezrin) | VIL2 | 0 | 2 |
| IMAGE: 85403 | Hs.231840 | WW domain binding protein 2 | WBP2 | 0 | −2 |
| IMAGE: 234004 | Hs.187991 | SOCS box-containing WD protein SWiP-1 | WSB1 | 0 | 0 |
| IMAGE: 271699 | Hs.187991 | SOCS box-containing WD protein SWiP-1 | WSB1 | 1 | −2 |
| IMAGE: 1605407 | Hs.136644 | WD repeat and SOCS box containing protein 2 | WSB2 | 0 | 2 |
| IMAGE: 898095 | Hs.119 | Wilms tumor 1 associated protein | WTAP | 0 | −2 |
| IMAGE: 258761 | Hs.23495 | HBxAg transactivated protein 1 | XTP1 | 0 | 0 |
| IMAGE: 292996 | Hs.349530 | tyrosine 3-monooxygenase/tryptophan 5-monooxygenase activation protein, eta polypeptide | YWHAH | 0 | 0 |
| IMAGE: 1933716 | Hs.15220 | zinc finger protein 106 | ZFP106 | 0 | −2 |
| IMAGE: 824875 | Hs.15220 | zinc finger protein 106 | ZFP106 | 1 | −2 |
| IMAGE: 845419 | Hs.351605 | zinc finger protein 276 | ZFP276 | 0 | 0 |
| IMAGE: 755373 | Hs.33532 | zinc finger protein 151 (pHZ-67) | ZNF151 | 0 | −2 |
| IMAGE: 461613 | Hs.250493 | zinc finger protein 219 | ZNF219 | 0 | −2 |
| IMAGE: 562115 | Hs.356344 | zinc finger protein 36 (KOX 18) | ZNF36 | 0 | −2 |
| IMAGE: 486356 | Hs.305953 | zinc finger protein 83 (HPF1) | ZNF83 | 0 | −2 |
| IMAGE: 1034491 | | Data not found | | 0 | 2 |
| IMAGE: 1664309 | | Data not found | | 0 | 2 |
| IMAGE: 1680098 | Hs.455887 | *Homo sapiens* transcribed sequences | | 0 | 2 |
| IMAGE: 1881224 | Hs.158501 | *Homo sapiens* transcribed sequences | | 0 | 2 |
| IMAGE: 1926715 | | Data not found | | 0 | 2 |
| IMAGE: 195419 | | In multiple clusters | | 0 | 2 |
| IMAGE: 2012523 | Hs.458417 | *Homo sapiens* transcribed sequence with strong similarity to protein pir: I56326 (*H. sapiens*) 156326 fatty acid binding protein homolog - human | | 0 | 2 |
| IMAGE: 207029 | | Data not found | | 0 | 2 |
| IMAGE: 232586 | Hs.102219 | *Homo sapiens* transcribed sequences | | 0 | 2 |
| IMAGE: 246684 | Hs.48058 | *Homo sapiens* transcribed sequences | | 0 | 2 |
| IMAGE: 260187 | Hs.44307 | *Homo sapiens* transcribed sequence with weak similarity to protein ref: NP_060265.1 (*H. sapiens*) hypothetical protein FLJ20378 [*Homo sapiens*] | | 0 | 2 |
| IMAGE: 278687 | | In multiple clusters | | 0 | 2 |
| IMAGE: 279616 | Hs.46852 | *Homo sapiens* transcribed sequences | | 0 | 2 |
| IMAGE: 281039 | | In multiple clusters | | 0 | 2 |
| IMAGE: 283751 | Hs.44205 | *Sapiens*, clone MGC: 32686 IMAGE: 4051739, mRNA, complete cds | | 0 | 2 |
| IMAGE: 290162 | | In multiple clusters | | 0 | 2 |
| IMAGE: 295473 | | In multiple clusters | | 0 | 2 |
| IMAGE: 30093 | | Data not found | | 0 | 2 |
| IMAGE: 302933 | | In multiple clusters | | 0 | 2 |
| IMAGE: 32134 | | In multiple clusters | | 0 | 2 |
| IMAGE: 321354 | | In multiple clusters | | 0 | 2 |
| IMAGE: 321905 | Hs.55080 | *Homo sapiens* transcribed sequences | | 0 | 2 |
| IMAGE: 32641 | | In multiple clusters | | 0 | 2 |
| IMAGE: 345833 | | In multiple clusters | | 0 | 2 |
| IMAGE: 40017 | | In multiple clusters | | 0 | 2 |
| IMAGE: 418279 | Hs.35962 | *Sapiens*, clone IMAGE: 4448513, mRNA | | 0 | 2 |
| IMAGE: 454219 | Hs.117035 | *Homo sapiens* transcribed sequences | | 0 | 2 |
| IMAGE: 470930 | | In multiple clusters | | 0 | 2 |
| IMAGE: 645702 | Hs.169514 | *Homo sapiens* transcribed sequence with weak similarity to protein ref: NP_060265.1 (*H. sapiens*) hypothetical protein FLJ20378 [*Homo sapiens*] | | 0 | 2 |
| IMAGE: 665508 | | In multiple clusters | | 0 | 2 |
| IMAGE: 66852 | | Data not found | | 0 | 2 |
| IMAGE: 687297 | Hs.20843 | *Sapiens* cDNA FLJ11245 fis, clone PLACE1008629. | | 0 | 2 |
| IMAGE: 713031 | | In multiple clusters | | 0 | 2 |
| IMAGE: 731290 | Hs.456464 | *Homo sapiens* transcribed sequences | | 0 | 2 |
| IMAGE: 745476 | Hs.208414 | *Sapiens* mRNA; cDNA DKFZp564D0472 (from clone DKFZp564D0472) | | 0 | 2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 757144 | | In multiple clusters | | 0 | 2 |
| IMAGE: 810156 | | In multiple clusters | | 0 | 2 |
| IMAGE: 811999 | | In multiple clusters | | 0 | 2 |
| IMAGE: 813636 | Hs.452394 | *Sapiens* HSPC151 mRNA, complete cds | | 0 | 2 |
| IMAGE: 824132 | | In multiple clusters | | 0 | 2 |
| IMAGE: 824756 | | Data not found | | 0 | 2 |
| IMAGE: 824917 | | In multiple clusters | | 0 | 2 |
| IMAGE: 825659 | | In multiple clusters | | 0 | 2 |
| IMAGE: 841238 | Hs.237868 | *Sapiens* esophageal carcinoma-related mRNA, complete sequence | | 0 | 2 |
| IMAGE: 853968 | Hs.116680 | *Homo sapiens* transcribed sequences | | 0 | 2 |
| IMAGE: 858375 | Hs.116808 | *Sapiens* mRNA; cDNA DKFZp566J1846 (from clone DKFZp566J1846) | | 0 | 2 |
| IMAGE: 897680 | | Data not found | | 0 | 2 |
| IMAGE: 1035796 | Hs.339665 | *Sapiens*, Similar to RIKEN cDNA 2700049P18 gene, clone MGC: 57827 IMAGE: 6064384, mRNA, complete cds | | 0 | 0 |
| IMAGE: 130204 | | In multiple clusters | | 0 | 0 |
| IMAGE: 131316 | Hs.339665 | *Sapiens*, Similar to RIKEN cDNA 2700049P18 gene, clone MGC: 57827 IMAGE: 6064384, mRNA, complete cds | | 1 | 0 |
| IMAGE: 139705 | Hs.28465 | *Sapiens*, clone IMAGE: 5263527, mRNA | | 0 | 0 |
| IMAGE: 1536451 | Hs.126714 | *Homo sapiens* transcribed sequence with weak similarity to protein ref: NP_062553.1 (*H. sapiens*) hypothetical protein FLJ11267 [*Homo sapiens*] | | 0 | 0 |
| IMAGE: 1564601 | Hs.186579 | *Sapiens*, clone IMAGE: 4081483, mRNA | | 0 | 0 |
| IMAGE: 1677546 | Hs.135448 | *Homo sapiens* transcribed sequence | | 0 | 0 |
| IMAGE: 1837950 | Hs.120605 | *Homo sapiens* transcribed sequences | | 0 | 0 |
| IMAGE: 1911913 | Hs.370736 | *Homo sapiens* transcribed sequences | | 0 | 0 |
| IMAGE: 196475 | Hs.418535 | *Homo sapiens* transcribed sequences | | 0 | 0 |
| IMAGE: 202704 | Hs.268919 | *Sapiens* cDNA FLJ37623 fis, clone BRCOC2014013. | | 0 | 0 |
| IMAGE: 203275 | | In multiple clusters | | 0 | 0 |
| IMAGE: 220376 | Hs.432827 | *Homo sapiens* transcribed sequence with weak similarity to protein pir: S21348 (*R. norvegicus*) S21348 probable pol polyprotein-related protein 4 - rat | | 0 | 0 |
| IMAGE: 236142 | | Data not found | | 0 | 0 |
| IMAGE: 241282 | Hs.299797 | *Sapiens* cDNA FLJ34225 fis, clone FCBBF3023372. | | 0 | 0 |
| IMAGE: 308633 | | In multiple clusters | | 0 | 0 |
| IMAGE: 346257 | Hs.319215 | *Sapiens*, clone IMAGE: 5270727, mRNA | | 0 | 0 |
| IMAGE: 358052 | Hs.348874 | *Sapiens* full length insert cDNA clone ZE04G11 | | 0 | 0 |
| IMAGE: 366414 | | In multiple clusters | | 0 | 0 |
| IMAGE: 366558 | | In multiple clusters | | 0 | 0 |
| IMAGE: 510273 | | In multiple clusters | | 0 | 0 |
| IMAGE: 610362 | | In multiple clusters | | 0 | 0 |
| IMAGE: 625616 | | In multiple clusters | | 0 | 0 |
| IMAGE: 627688 | Hs.104123 | *Homo sapiens* transcribed sequence | | 0 | 0 |
| IMAGE: 739511 | | In multiple clusters | | 0 | 0 |
| IMAGE: 745138 | Hs.457442 | *Sapiens* cDNA FLJ35797 fis, clone TESTI2005892, highly similar to TUBULIN ALPHA-3/ALPHA-7 CHAIN. | | 0 | 0 |
| IMAGE: 770066 | | In multiple clusters | | 0 | 0 |
| IMAGE: 809530 | | Data not found | | 0 | 0 |
| IMAGE: 809731 | Hs.375205 | *Sapiens*, clone IMAGE: 4589300, mRNA, partial cds | | 0 | 0 |
| IMAGE: 810600 | Hs.430976 | *Homo sapiens* transcribed sequence with strong similarity to protein pir: B42856 (*H. sapiens*) B42856 ubiquitin carrier protein E2 - human | | 0 | 0 |
| IMAGE: 810899 | | In multiple clusters | | 0 | 0 |
| IMAGE: 853066 | Hs.446510 | *Homo sapiens* transcribed sequence with weak similarity to protein ref: NP_060265.1 (*H. sapiens*) hypothetical protein FLJ20378 [*Homo sapiens*] | | 0 | 0 |
| IMAGE: 108422 | | In multiple clusters | | 0 | −2 |
| IMAGE: 121512 | | In multiple clusters | | 0 | −2 |
| IMAGE: 128054 | Hs.356538 | *Homo sapiens* transcribed sequence with moderate similarity to protein pdb: 1BGM (*E. coli*) | | 0 | |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| | | O Chain O, Beta-Galactosidase (Chains I-P) | | | |
| IMAGE: 129883 | | In multiple clusters | | 0 | −2 |
| IMAGE: 137602 | Hs.106148 | Sapiens mRNA; cDNA DKFZp434G0972 (from clone DKFZp434G0972) | | 0 | −2 |
| IMAGE: 141854 | | In multiple clusters | | 0 | −2 |
| IMAGE: 1558625 | Hs.25144 | Sapiens cDNA FLJ31683 fis, clone NT2RI2005353. | | 0 | −2 |
| IMAGE: 1564426 | Hs.446437 | Homo sapiens transcribed sequence with weak similarity to protein ref: NP_060312.1 (H. sapiens) hypothetical protein FLJ20489 [Homo sapiens] | | 0 | −2 |
| IMAGE: 1569077 | | Data not found | | 0 | −2 |
| IMAGE: 1601926 | Hs.457626 | Homo sapiens transcribed sequences | | 0 | −2 |
| IMAGE: 1649341 | | Data not found | | 0 | −2 |
| IMAGE: 1686600 | Hs.170261 | Sapiens cDNA FLJ38461 fis, clone FEBRA2020977. | | 0 | −2 |
| IMAGE: 1892599 | Hs.409561 | Homo sapiens transcribed sequence | | 0 | −2 |
| IMAGE: 1898442 | Hs.34068 | Sapiens, clone IMAGE: 5296353, mRNA | | 0 | −2 |
| IMAGE: 1898826 | | Data not found | | 0 | −2 |
| IMAGE: 2013496 | Hs.268016 | Sapiens cDNA: FLJ21243 fis, clone COLO1164. | | 1 | −2 |
| IMAGE: 210486 | | In multiple clusters | | 0 | −2 |
| IMAGE: 240480 | | In multiple clusters | | 0 | −2 |
| IMAGE: 249486 | | Data not found | | 0 | −2 |
| IMAGE: 256619 | | In multiple clusters | | 0 | −2 |
| IMAGE: 262313 | Hs.108873 | Homo sapiens transcribed sequences | | 1 | −2 |
| IMAGE: 266263 | Hs.26418 | Sapiens, clone IMAGE: 5261213, mRNA | | 0 | −2 |
| IMAGE: 278729 | Hs.29088 | Homo sapiens transcribed sequence with weak similarity to protein sp: P11369 (M. musculus) POL2_MOUSE Retrovirus-related POL polyprotein [Contains: Reverse transcriptase; Endonuclease] | | 0 | −2 |
| IMAGE: 28927 | Hs.388212 | Homo sapiens transcribed sequence | | 0 | −2 |
| IMAGE: 289505 | Hs.44829 | Homo sapiens transcribed sequence with moderate similarity to protein ref: NP_060265.1 (H. sapiens) hypothetical protein FLJ20378 [Homo sapiens] | | 0 | −2 |
| IMAGE: 291394 | Hs.108873 | Homo sapiens transcribed sequences | | 0 | −2 |
| IMAGE: 340745 | Hs.25144 | Sapiens cDNA FLJ31683 fis, clone NT2RI2005353. | | 1 | −2 |
| IMAGE: 346643 | Hs.23575 | Homo sapiens transcribed sequences | | 0 | −2 |
| IMAGE: 358647 | Hs.26418 | Sapiens, clone IMAGE: 5261213, mRNA | | 1 | −2 |
| IMAGE: 361456 | | In multiple clusters | | 0 | −2 |
| IMAGE: 38009 | Hs.170056 | Sapiens mRNA; cDNA DKFZp586B0220 (from clone DKFZp586B0220) | | 0 | −2 |
| IMAGE: 38072 | Hs.293782 | Sapiens, clone MGC: 27375 IMAGE: 4688423, mRNA, complete cds | | 1 | −2 |
| IMAGE: 42935 | Hs.445537 | Homo sapiens transcribed sequence with weak similarity to protein pir: T12486 (H. sapiens) T12486 hypothetical protein DKFZp566H033.1 - human | | 0 | −2 |
| IMAGE: 431805 | | Data not found | | 0 | −2 |
| IMAGE: 487499 | Hs.24758 | Sapiens cDNA FLJ32068 fis, clone OCBBF1000114. | | 0 | −2 |
| IMAGE: 491415 | | In multiple clusters | | 0 | −2 |
| IMAGE: 503839 | | In multiple clusters | | 0 | −2 |
| IMAGE: 664233 | | In multiple clusters | | 0 | −2 |
| IMAGE: 69309 | Hs.452719 | Homo sapiens transcribed sequence with weak similarity to protein sp: P29974 (M. musculus) CNG1_MOUSE cGMP-gated cation channel alpha 1 (CNG channel alpha 1) (CNG-1) (CNG1) (Cyclic nucleotide gated channel alpha 1) (Cyclic nucleotide gated channel, photoreceptor) (Cyclic-nucleotide-gated cation channel 1) (Rod photoreceptor cGMP-gated channel alpha subunit) | | 0 | −2 |
| IMAGE: 69378 | Hs.279898 | Sapiens cDNA: FLJ23165 fis, clone LNG09846. | | 0 | −2 |
| IMAGE: 741954 | | In multiple clusters | | 0 | −2 |
| IMAGE: 742685 | Hs.291804 | Sapiens cDNA FLJ35517 fis, clone SPLEN2000698. | | 0 | −2 |

-continued

Sequences

| CloneID | UGCluster | Name | Symbol | Redundant (Y = 1, N = 0) | CSR. Activated = 2, Quiescent = −2, cell cycle = 0 |
|---|---|---|---|---|---|
| IMAGE: 742806 | Hs.398090 | *Sapiens* cDNA FLJ39131 fis, clone NTONG2008143. | | 0 | −2 |
| IMAGE: 767289 | | In multiple clusters | | 0 | −2 |
| IMAGE: 782737 | | In multiple clusters | | 0 | −2 |
| IMAGE: 785819 | Hs.268016 | *Sapiens* cDNA: FLJ21243 fis, clone COL01164. | | 0 | −2 |
| IMAGE: 786573 | | In multiple clusters | | 0 | −2 |
| IMAGE: 788217 | Hs.34359 | *Homo sapiens* transcribed sequences | | 0 | −2 |
| IMAGE: 795427 | Hs.356688 | *Sapiens* cDNA FLJ37527 fis, clone BRCAN2011946. | | 0 | −2 |
| IMAGE: 810133 | Hs.10362 | *Sapiens* cDNA: FLJ20944 fis, clone ADSE01780. | | 0 | −2 |
| IMAGE: 810326 | | In multiple clusters | | 0 | −2 |
| IMAGE: 810486 | Hs.356618 | *Sapiens* cDNA clone IMAGE: 4822701, partial cds | | 0 | −2 |
| IMAGE: 810859 | | In multiple clusters | | 0 | −2 |
| IMAGE: 811751 | Hs.293782 | *Sapiens*, clone MGC: 27375 IMAGE: 4688423, mRNA, complete cds | | 0 | −2 |
| IMAGE: 811837 | | In multiple clusters | | 0 | −2 |
| IMAGE: 81417 | | In multiple clusters | | 0 | −2 |
| IMAGE: 824111 | Hs.420569 | *Homo sapiens* transcribed sequence with moderate similarity to protein sp: Q99576 (*H. sapiens*) GILZ__HUMAN Glucocorticoid-induced leucine zipper protein (Delta sleep-inducing peptide immunoreactor) (DSIP-immunoreactive peptide) (DIP protein) (hDIP) (TSC-22-like protein) (TSC-22R) | | 0 | −2 |
| IMAGE: 824150 | Hs.439107 | *Sapiens*, clone IMAGE: 5288451, mRNA | | 0 | −2 |
| IMAGE: 82434 | | In multiple clusters | | 0 | −2 |
| IMAGE: 854122 | Hs.349326 | *Sapiens* cDNA FLJ30677 fis, clone FCBBF2000087. | | 0 | −2 |
| IMAGE: 855808 | Hs.443798 | *Homo sapiens* transcribed sequences | | 0 | −2 |
| IMAGE: 866276 | Hs.442762 | *Homo sapiens* transcribed sequences | | 0 | −2 |
| IMAGE: 898133 | Hs.351108 | *Homo sapiens* transcribed sequences | | 0 | −2 |
| IMAGE: 951007 | Hs.112862 | *Homo sapiens* transcribed sequences | | 0 | −2 |

What is claimed is:

1. A method of classifying a human carcinoma, said method comprising:

(a) obtaining a Core Serum Response (CSR) transcriptional expression profile from a carcinoma sample from a human subject, wherein said CSR expression profile comprises a dataset of expression information for at least 35 genes selected from ACAS2; ACINUS; ADD3; AIP1; ALEX3; APOD; APP; ARHGAP12; ARHGEF3; ATP6V0A1; AXIN2; BBC3; BCL6; BF; BHC80; BHLHB2; BOCT; C1S; C20orf108; C5orf4; CAMLG; CCNG2; CCNL2; CDC14B; CDKN1A; CDKN1C; CLCN6; CLIC2; CNTNAP1; CPR8; CRTAP; CSF1; CST3; CTNS; CTSF; CYP27A1; DEPP; DHRS6; DKFZP434B103; DKFZp434L142; DKFZP434O1427; DKFZP586A0522; DKFZp762H185; DNM1; DPP7; DPYSL2; DUSP22; F10; FABP3; FACL3; FADS1; FADS2; FCGRT; FDPS; FLJ10618; FLJ10849; FLJ10948; FLJ11286; HFLJ14525; FLJ20059; FLJ20154; FLJ21016; FLJ21986; FLJ23462; FLJ30574; FLJ31033; FLJ32731; FLJ90754; FLJ90798; FYCO1; GABARAPL1; GABBR1; GATM; GG2-1; GLS; GPR124; GSN; H2AV; HDAC5; HECA; HMGCS1; IDI1; IGBP1; IL1R1; IL6ST; INSIG1; ITPKB; JAG1; KAI1; KIAA0323; KIAA0342; KIAA0367; KIAA0874; KIAA1036; KIAA1109; KIAA1228; KIAA1268; KIAA1305; KIAA1536; KIAA1554; KIAA1946; KIT; KLHL5; LDB1; LDLR; LIPA; LOC115294; LOC153222; LOC169611; LOC201895; LOC221810; LOC253263; LOC284018; LOC284436; LOC285362; LOC339924; LOC51279; LOC56757; LPIN1; LRIG2; LRP1; LSS; LUM; MAF; MAN1A1; MBP; MCP; MEF2D; MFGE8; MGC10500; MGC13047; MGC15429; MGC17330; MGC39820; MGC4170; MIG-6; MRF2; MVD; MXI1; NCOA3; NIFU; OSBPL8; P8; PA26; PBXIP1; PDK2; PGCP; PHACS; PKIG; PLA2R1; PLD3; PLU-1; PLXNB1; POR; PROL2; PTPRU; Rab11-FIP2; RARRES3; REV3L; RRM2B; SATB1; SBP1; SC4MOL; SCD; SELENBP1; SEMACAP3; SERPING1; SES2; SFTPB; SLC35E2; SLC40A1; SLC5A3; SLPI; SNRP70; SQLE; SQRDL; SVIL; TBRG1; TIMP2; TNFAIP2; TNFSF12; TNXB; TP53INP1; TRIM22; TSC22; VAMP4; WBP2; WTAP; ZFP106; ZNF151; ZNF219; ZNF36; ZNF83; DKFZp434G0972; FLJ31683; FLJ20489; FLJ38461; IMAGE:5296353; FLJ21243; IMAGE:5261213; FLJ20378; FLJ31683; IMAGE:5261213; DKFZp586B0220; IMAGE:4688423; DKFZp566H033.1; FLJ32068; FLJ23165; FLJ35517; FLJ39131; FLJ21243; FLJ37527; FLJ20944; IMAGE: 4822701; IMAGE:4688423; IMAGE:5288451; FLJ30677; ADAMTS1; AND-1; ARHC; BAF53A; BCCIP; BM039; BRCA2; BRIP1; C11orf14; C11orf24; C13orf1; C1orf33; C6orf55; C8orf13; CBX1; CCT5; CDCA4; CDK2; CENPJ; CGI-121; CHEK1; CKLF; CL640; COPS6; CORO1C; COTL1; COX17; DC13; DCK; DCLRE1B; DHFR; DKFZP727G051;

DKFZp761L1417; DLEU1; DLEU2; DUT; EBNA1BP2; EEF1E1; EIF4EBP1; EIF4G1; EMP2; ENIGMA; ENO1; EPHB1; ERP70; ESDN; F3; FARSL; FLJ10036; FLJ10292; FLJ10407; FLJ10983; FLJ12643; FLJ12953; FLJ20331; FLJ30532; FLJ32915; FLNC; FRSB; GGH; GNG11; GPLD1; H2AFZ; HAS2; HMGB1; HMGN2; HN1L; HNRPA2B1; HNRPR; HRB2; HRI; HSPC111; HSU79274; ID2; ID3 IFRD2; IL7R; IMP4; IPO4; ITGA6; JTV1; KEO4; KIAA0090; KIAA0095; KIAA1363; KIAA1720; LMNB2; LOC115106; LOC129401; LOC201562; LOC51128; LOC51668; LOC56902; LOC56926; LOC93081; LOXL2; LSM3; LSM4; LYAR; MAP3K8; MAPRE1; MCM3; MCM7; MCT-1; MEP50; MET; MGC10200; MGC10974; MGC11266; MGC13170; MGC14480; MGC3101; MGC4308; MGC4825; MKKS; MNAT1; MRPL12; MRPL37; MRPS16; MRPS28; MSN; MT1F; MT3; MTH2; MTHFD1; MYBL1; MYBL2; MYCBP; MYL6; RIKEN cDNA 1110001A07; NLN; NME1; NOLA2; NUDT1; NUP107; NUPL1; NUTF2; OIP2; PA2G4; PAICS; PCNT1; PCSK7; PDAP1; PFKP; PFN1; PITPNC1; PLAUR; PLG; PLOD2; PNN; POLE2; POLR3K; PPIH; PSMA7; PSMC3; PSMD12; PSMD14; PSMD2; PTS; RBM14; RBMX; RFC3; RNASEH2A; RNASEP1; RNF138; RNF41; RPN1; RUVBL1; SDC1; SDFR1; SFRS10; SFRS2; SLC16A1; SLC25A5; SMC2L1; SMS; SMURF2; SNRPA; SNRPA1; SNRPB; SNRPC; SNRPD1; SNRPE; SRM; SSR3; SSSCA1; STK17A; STK18; TAGLN; TCEB1; TCTEL1; TFPI2; TIM50L; TNFRSF12A; TOMM40; TPI1; TPM1; TPM2; TUBA1; TUBG1; TXNL2; UAP1; UBE2J1; UMPK; UMPS; VDAC1; VIL2; WSB2; FLJ20378; IMAGE:4051739; IMAGE:4448513; FLJ20378; FLJ11245; DKFZp564D0472; HSPC151; DKFZp566J1846: CLC; RPLP2; RANBP1; PTMA; TFPI2; IFITM1; PSMB7; PFN1; HNRPAB; UMPK; FABP5; RNASE4; IFITM1; and MAPK8IP2 by extracting mRNA from said carcinoma; quantitating the level of mRNA corresponding to said at least 35 genes; and comparing said level of mRNA to the level of said mRNA in a reference sample, wherein genes having hybridization signals at least 1.5-fold greater than the local background are considered expressed; and (b) comparing said obtained expression profile to a reference CSR expression profile comprising a dataset of expression information for at least 35 genes obtained from multiple human primary fibroblasts following exposure to serum, wherein ACAS2; ACINUS; ADD3; AIP1; ALEX3; APOD; APP; ARHGAP12; ARHGEF3; ATP6V0A1; AXIN2; BBC3; BCL6; BF; BHC80; BHLHB2; BOCT; C1S; C20orf108; C5orf4; CAMLG; CCNG2; CCNL2; CDC14B; CDKN1A; CDKN1C; CLCN6; CLIC2; CNTNAP1; CPR8; CRTAP; CSF1; CST3; CTNS; CTSF; CYP27A1; DEPP; DHRS6; DKFZP434B103; DKFZp434L142; DKFZP434O1427; DKFZP586A0522; DKFZp762H185; DNM1; DPP7; DPYSL2; DUSP22; F10; FABP3; FACL3; FADS1; FADS2; FCGRT; FDPS; FLJ10618; FLJ10849; FLJ10948; FLJ11286; FLJ14525; FLJ20059; FLJ20154; FLJ21016; FLJ21986; FLJ23462; FLJ30574; FLJ31033; FLJ32731; FLJ90754; FLJ90798; FYCO1; GABARAPL1; GABBR1; GATM; GG2 1; GLS; GPR124; GSN; H2AV; HDAC5; HECA; HMGCS1; IDI1; IGBP1; IL1R1; IL6ST; INSIG1; ITPKB; JAG1; KAI1; KIAA0323; KIAA0342; KIAA0367; KIAA0874; KIAA1036; KIAA1109; KIAA1228; KIAA1268; KIAA1305; KIAA1536; KIAA1554; KIAA1946; KIT; KLHL5; LDB1; LDLR; LIPA; LOC115294; LOC153222; LOC169611; LOC201895; LOC221810; LOC253263; LOC284018; LOC284436; LOC285362; LOC339924; LOC51279; LOC56757; LPIN1; LRIG2; LRP1; LSS; LUM; MAF; MAN1A1; MBP; MCP; MEF2D; MFGE8; MGC10500; MGC13047; MGC15429; MGC17330; MGC39820; MGC4170; MIG-6; MRF2; MVD; MXI1; NCOA3; NIFU; OSBPL8; P8; PA26; PBXIP1; PDK2; PGCP; PHACS; PKIG; PLA2R1; PLD3; PLU-1; PLXNB1; POR; PROL2; PTPRU; Rab11-FIP2; RARRES3; REV3L; RRM2B; SATB1; SBP1; SC4MOL; SCD; SELENBP1; SEMACAP3; SERPING1; SES2; SFTPB; SLC35E2; SLC40A1; SLC5A3; SLPI; SNRP70; SQLE; SQRDL; SVIL; TBRG1; TIMP2; TNFAIP2; TNFSF12; TNXB; TP53INP1; TRIM22; TSC22; VAMP4; WBP2; WTAP; ZFP106; ZNF151; ZNF219; ZNF36; ZNF83; DKFZp434G0972; FLJ31683; FLJ20489; FLJ38461; IMAGE:5296353; FLJ21243; IMAGE:5261213; FLJ20378; FLJ31683; IMAGE: 5261213; DKFZp586B0220; IMAGE:4688423; DKFZp566H033.1; FLJ32068; FLJ23165; FLJ35517; FLJ39131; FLJ21243; FLJ37527; FLJ20944; IMAGE: 4822701; IMAGE:4688423; IMAGE:5288451; and FLJ30677; are serum-repressed genes;

and ADAMTS1; AND-1; ARHC; BAF53A; BCCIP; BM039; BRCA2; BRIP1; C11orf14; C11orf24; C13orf1; C1orf33; C6orf55; C8orf13; CBX1; CCT5; CDCA4; CDK2; CENPJ; CGI-121; CHEK1; CKLF; CL640; COPS6; CORO1C; COTL1; COX17; DC13; DCK; DCLRE1B; DHFR; DKFZP727G051; DKFZp761L1417; DLEU1; DLEU2; DUT; EBNA1BP2; EEF1E1; EIF4EBP1; EIF4G1; EMP2; ENIGMA; ENO1; EPHB1; ERP70; ESDN; F3; FARSL; FLJ10036; FLJ10292; FLJ10407; FLJ10983; FLJ12643; FLJ12953; FLJ20331; FLJ30532; FLJ32915; FLNC; FRSB; GGH; GNG11; GPLD1; H2AFZ; HAS2; HMGB1; HMGN2; HN1L; HNRPA2B1; HNRPR; HRB2; HRI; HSPC111; HSU79274; ID2; ID3 IFRD2; IL7R; IMP4; IPO4; ITGA6; JTV1; KEO4; KIAA0090; KIAA0095; KIAA1363; KIAA1720; LMNB2; LOC115106; LOC129401; LOC201562; LOC51128; LOC51668; LOC56902; LOC56926; LOC93081; LOXL2; LSM3; LSM4; LYAR; MAP3K8; MAPRE1; MCM3; MCM7; MCT-1; MEP50; MET; MGC10200; MGC10974; MGC11266; MGC13170; MGC14480; MGC3101; MGC4308; MGC4825; MKKS; MNAT1; MRPL12; MRPL37; MRPS16; MRPS28; MSN; MT1F; MT3; MTH2; MTHFD1; MYBL1; MYBL2; MYCBP; MYL6; RIKEN cDNA 1110001A07; NLN; NME1; NOLA2; NUDT1; NUP107; NUPL1; NUTF2; OIP2; PA2G4; PAICS; PCNT1; PCSK7; PDAP1; PFKP; PFN1; PITPNC1; PLAUR; PLG; PLOD2; PNN; POLE2; POLR3K; PPIH; PSMA7; PSMC3; PSMD12; PSMD14; PSMD2; PTS; RBM14; RBMX; RFC3; RNASEH2A; RNASEP1; RNF138; RNF41; RPN1; RUVBL1; SDC1; SDFR1; SFRS10; SFRS2; SLC16A1; SLC25A5; SMC2L1; SMS; SMURF2; SNRPA; SNRPA1; SNRPB; SNRPC; SNRPD1; SNRPE; SRM; SSR3; SSSCA1; STK17A; STK18; TAGLN; TCEB1; TCTEL1; TFPI2; TIM50L; TNFRSF12A; TOMM40; TPI1; TPM1; TPM2; TUBA1; TUBG1; TXNL2; UAP1; UBE2J1; UMPK; UMPS; VDAC1; VIL2; WSB2; FLJ20378; IMAGE:4051739; IMAGE:4448513;

FLJ20378; FLJ11245; DKFZp564D0472; HSPC151; DKFZp566J1846: CLC; RPLP2; RANBP1; PTMA; TFPI2; IFITM1; PSMB7; PFN1; HNRPAB; UMPK; FABP5; RNASE4; IFITM1; and MAPK8IP2 are serum-activated genes;

wherein a carcinoma sample having high expression of serum-induced genes and low expression of serum-repressed genes is classified as activated and has decreased distant metastasis-free probability and overall survival compared to a carcinoma sample having low expression of serum-induced genes and high expression of serum-repressed genes, which is classified as quiescent.

2. The method according to claim 1, wherein said CSR expression profile comprises transcriptional information from a dataset comprising MCT-1; FLJ10292; DKFZp434G0972; SNRPC; MRPL12; LSM3; MIG-6; RBM14; RFC3; DCLRE1B; RNASEP1; PAICS; NME1; H2AFZ; SCD; CLC; FADS1; LOC93081; WSB2; MTH2; VDAC1; CKLF; NUTF2; RPLP2; HAS2; LOC51659; POR; MSN; STK18; KIAA1946; SNRPA; ESDN; CORO1C; MCM3; PLAUR; MYBL2; RNF138; FADS2; TCEB1; PGCP; CHEK1; UAP1; FLJ10036; TUBG1; ITGA6; HNRPA2B1; PSMA7; MAPRE1; NUP107; GLS; RANBP1; LOC56926; PTMA; PSMC3; SLPI; RNASEH2A; ENO1; TCTEL1; C6orf55; FLJ14525; OIP2; BAF53A; LOC51128; HSPC111; CENPJ; BM039; SSR3; KIAA1305; MGC11266; TFPI2; SFRS10; MYBL1; H2AV; JTV1; FLJ10407; RFC4; PITPNC1; SNRPE; FDPS; CDCA4; EBNA1BP2; TNFRSF12A; IFITM1; FLJ12643; MFGE8; MGC14480; FLJ23468; KIAA0367; NUDT1; SDFR1; MGC4308; PLOD2; MRPL37; FLJ10618; LYAR; PSMD12; EIF4EBP1; MNAT1; PSMB7; EIF4G1; C13orf1; LOC51668; FLJ20331; MRPS28; INSIG1; LOC201562; TIMP2; HECA; DC13; DCK; SQLE; AND-1; SFRS2; PSMD2; SLC16A1; PFN1; IDI1; LMNB2; SRM; MCM7; CBX1; HMGCS1; GGH; SLC25A5; SNRPA1; HNRPAB; LPIN1; SDC1; SNRPB; SMS; NUPL1; STK17A; FRSB; IMP4; RRM2B; UMPK; POLE2; PFKP; FLJ20154; MEP50; MGC10974; FCGRT; CTSF; MXI1; DHRS6; AXIN2; PA26; CCNL2; ZFP106; FABP5; RNF41; KIAA0090; KIAA1036; KIAA1536; LOC153222; DKFZp586B0220; FLJ38461; BHLHB2; GPR124; RARRES3; SEMACAP3; ARHC; CHEK1; DKFZp564D0472; CLCN6; SLC35E2; LRIG2; FLJ32068; ZNF219; MAN1A1; FYCO1; HRI; ARHGEF3; LDB1; IMAGE:5261213; MGC17330; KIAA0874; FLJ90798; RNASE4; EMP2; CST3; FLJ23462; DKFZp434L142; SELENBP1; PKIG; FLJ10948; FLJ30574; C20orf108; ZNF36; FLJ37527; IGBP1; IFITM1; BOCT; LOC253263; FLJ20378; F10; FLNC; SLC40A1; F3; KIAA1109; BF; MGC4170; GATM; TP53INP1; MYL6; LUM; SES2; MAPK8IP2; HSPC151; IL6ST; IL1R1; GNG11; BBC3; FLJ10849; ERP70; and NIFU;

and wherein said reference CSR expression profile comprises expression information from a a dataset comprising MCT-1; FLJ10292; DKFZp434G0972; SNRPC; MRPL12; LSM3; MIG-6; RBM14; RFC3; DCLRE1B; RNASEP1; PAICS; NME1; H2AFZ; SCD; CLC; FADS1; LOC93081; WSB2; MTH2; VDAC1; CKLF; NUTF2; RPLP2; HAS2; LOC51659; POR; MSN; STK18; KIAA1946; SNRPA; ESDN; CORO1C; MCM3; PLAUR; MYBL2; RNF138; FADS2; TCEB1; PGCP; CHEK1; UAP1; FLJ10036; TUBG1; ITGA6; HNRPA2B1; PSMA7; MAPRE1; NUP107; GLS; RANBP1; LOC56926; PTMA; PSMC3; SLPI; RNASEH2A; ENO1; TCTEL1; C6orf55; FLJ14525; OIP2; BAF53A; LOC51128; HSPC111; CENPJ; BM039; SSR3; KIAA1305; MGC11266; TFPI2; SFRS10; MYBL1; H2AV; JTV1; FLJ10407; RFC4; PITPNC1; SNRPE; FDPS; CDCA4; EBNA1BP2; TNFRSF12A; IFITM1; FLJ12643; MFGE8; MGC14480; FLJ23468; KIAA0367; NUDT1; SDFR1; MGC4308; PLOD2; MRPL37; FLJ10618; LYAR; PSMD12; EIF4EBP1; MNAT1; PSMB7; EIF4G1; C13orf1; LOC51668; FIJ20331; MRPS28; INSIG1; LOC201562; TIMP2; HECA; DC13; DCK; SQLE; AND-1; SFRS2; PSMD2; SLC16A1; PFN1; IDI1; LMNB2; SRM; MCM7; CBX1; HMGCS1; GGH; SLC25A5; SNRPA1; HNRPAB; LPIN1; SDC1; SNRPB; SMS; NUPL1; STK17A; FRSB; IMP4; RRM2B; UMPK; POLE2; PFKP; FLJ20154; MEP50; MGC10974; FCGRT; CTSF; MXI1; DHRS6; AXIN2; PA26; CCNL2; ZFP106; FABP5; RNF41; KIAA0090; KIAA1036; KIAA1536; LOC153222; DKFZp586B0220; FLJ38461; BHLHB2; GPR124; RARRES3; SEMACAP3; ARHC; CHEK1; DKFZp564D0472; CLCN6; SLC35E2; LRIG2; FLJ32068; ZNF219; MAN1A1; FYCO1; HRI; ARHGEF3; LDB1; IMAGE:5261213; MGC17330; KIAA0874; FLJ90798; RNASE4; EMP2; CST3; FLJ23462; DKFZp434L142; SELENBP1; PKIG; FLJ10948; FLJ30574; C20orf108; ZNF36; FLJ37527; IGBP1; IFITM1; BOCT; LOC253263; FLJ20378; F10; FLNC; SLC40A1; F3; KIAA1109; BF; MGC4170; GATM; TP53INP1; MYL6; LUM; SES2; MAPK8IP2; HSPC151; IL6ST; IL1R1; GNG11; BBC3; FLJ10849; ERP70; and NIFU.

3. The method according to claim 1, wherein said carcinoma is a breast carcinoma, lung adenocarcinoma, prostate carcinoma, hepatocellular carcinoma or gastric carcinoma.

4. A kit for carcinoma classification, the kit comprising:
a set of primers specific for at least 35 Core Serum Response (CSR) genes selected from MCT-1; FLJ10292; DKFZp434G0972; SNRPC; MRPL12; LSM3; MIG-6; RBM14; RFC3; DCLRE1B; RNASEP1; PAICS; NME1; H2AFZ; SCD; CLC; FADS1; LOC93081; WSB2; MTH2; VDAC1; CKLF; NUTF2; RPLP2; HAS2; LOC51659; POR; MSN; STK18; KIAA1946; SNRPA; ESDN; CORO1C; MCM3; PLAUR; MYBL2; RNF138; FADS2; TCEB1; PGCP; CHEK1; UAP1; FLJ10036; TUBG1; ITGA6; HNRPA2B1; PSMA7; MAPRE1; NUP107; GLS; RANBP1; LOC56926; PTMA; PSMC3; SLPI; RNASEH2A; ENO1; TCTEL1; C6orf55; FLJ14525; OIP2; BAF53A; LOC51128; HSPC111; CENPJ; BM039; SSR3; KIAA1305; MGC11266; TFPI2; SFRS10; MYBL1; H2AV; JTV1; FLJ10407; RFC4; PITPNC1; SNRPE; FDPS; CDCA4; EBNA1BP2; TNFRSF12A; IFITM1; FLJ12643; MFGE8; MGC14480; FLJ23468; KIAA0367; NUDT1; SDFR1; MGC4308; PLOD2; MRPL37; FLJ10618; LYAR; PSMD12; EIF4EBP1; MNAT1; PSMB7; EIF4G1; C13orf1; LOC51668; FLJ20331; MRPS28; INSIG1; LOC201562; TIMP2; HECA; DC13; DCK; SQLE; AND-1; SFRS2; PSMD2; SLC16A1; PFN1; IDI1; LMNB2; SRM; MCM7; CBX1; HMGCS1; GGH; SLC25A5; SNRPA1; HNRPAB; LPIN1; SDC1; SNRPB; SMS; NUPL1; STK17A; FRSB; IMP4; RRM2B; UMPK; POLE2; PFKP; FLJ20154; MEP50; MGC10974; FCGRT; CTSF; MXI1; DHRS6; AXIN2; PA26; CCNL2; ZFP106; FABP5; RNF41; KIAA0090; KIAA1036; KIAA1536; LOC153222; DKFZp586B0220; FLJ38461; BHLHB2; GPR124; RARRES3; SEMACAP3; ARHC; CHEK1; DKFZp564D0472; CLCN6; SLC35E2; LRIG2;

FLJ32068; ZNF219; MAN1A1; FYCO1; HRI; ARHGEF3; LDB1; IMAGE:5261213; MGC17330; KIAA0874; FLJ90798; RNASE4; EMP2; CST3; FLJ23462; DKFZp434L142; SELENBP1; PKIG; FLJ10948; FLJ30574; C20orf108; ZNF36; FLJ37527; IGBP1; IFITM1; BOCT; LOC253263; FLJ20378; F10; FLNC; SLC40A1; F3; KIAA1109; BF; MGC4170; GATM; TP53I1NP1; MYL6; LUM; SES2; MAPK8IP2; HSPC151; IL6ST; IL1R1; GNG11; BBC3; FLJ10849; ERP70; and NIFU; and instructions for use.

5. The kit according to claim 4, further comprising a software package for statistical analysis of expression profiles, and a reference dataset for a CSR signature.

6. The method of claim 1, wherein said Core Serum Response (CSR) transcriptional expression profile from a carcinoma sample from a human subject comprises expression patterns centered by mean value within each dataset, and average linkage clustering carried out, wherein carcinoma sample is unambiguously assigned based on the first bifurcation in the hierarchical clustering dendrogram.

7. The method of claim 1, comprising:
averaging expression of said at least 35 genes in human fibroblasts from 10 fibroblast types to derive a single number for each gene;
calculating a Pearson correlation of averaged fibroblast expression with expression in said carcinoma sample;
wherein a carcinoma sample with a Pearson correlation greater than 0.2 with a serum-induced expression of CSR genes has decreased survival and relapse-free survival.

8. The method of claim 1, comprising:
correlating said Core Serum Response (CSR) transcriptional expression profile from a carcinoma sample to a vector representing the centroid of said reference CSR expression profile to obtain a correlation value;
wherein the correlation value generates a continuous score that can be scaled.

9. The method of claim 8, wherein the said at least 35 genes comprises:
MCM7; BM039; DC13; CCT5; MYBL2; PFKP; SNRPA1; FLJ23468; H2AFZ; GGH; LMNB2; FLJ10292; FLJ10407; MGC11266; STK18; TCEB1; MRPL12; AND-1; SQLE; H2AV; FLJ23462; SLC35E2; BF; LOC284436; BBC3; KIAA1536; SLC40A1; CTSF; MGC4170; FLJ90798; ZNF219; FLJ10849; IGBP1; FLJ37527.

10. The method of claim 9, further comprising setting a threshold limit for said correlation value, and validating said threshold by determining the threshold for metastasis in a known sample population.

11. The kit according to claim 4, wherein the said at least 35 genes comprises the following:
MCM7; BM039; DC13; CCT5; MYBL2; PFKP; SNRPA1; FLJ23468; H2AFZ; GGH; LMNB2; FLJ10292; FLJ10407; MGC11266; STK18; TCEB1; MRPL12; AND-1; SQLE; H2AV; FLJ23462; SLC35E2; BF; LOC284436; BBC3; KIAA1536; SLC40A1; CTSF; MGC4170; FLJ90798; ZNF219; FLJ10849; IGBP1; FLJ37527.

* * * * *